(12) United States Patent
Bowers et al.

(10) Patent No.: US 12,115,154 B2
(45) Date of Patent: Oct. 15, 2024

(54) COMPOUNDS FOR THE MODULATION OF PROPROTEIN CONVERTASE SUBTILISIN/KEXIN TYPE 9 (PCSK9)

(71) Applicant: SRX Cardio, LLC, Pittsford, NY (US)

(72) Inventors: Simeon Bowers, Oakland, CA (US); Mark Karbarz, Burlingame, CA (US); Jiang Zhu, Palo Alto, CA (US); Thomas E. Barta, Carrboro, NC (US); Jonathan William Bourne, Fairport, NY (US); Anjali Pandey, Fremont, CA (US)

(73) Assignee: SRX Cardio, LLC, Pittsford, NY (US)

( * ) Notice: Subject to any disclaimer, the term of this patent is extended or adjusted under 35 U.S.C. 154(b) by 272 days.

(21) Appl. No.: 17/124,357

(22) Filed: Dec. 16, 2020

(65) Prior Publication Data

US 2022/0193058 A1 Jun. 23, 2022

(51) Int. Cl.
| | | |
|---|---|---|
| *C07D 211/14* | (2006.01) | |
| *A61K 31/451* | (2006.01) | |
| *A61K 31/4545* | (2006.01) | |
| *A61P 3/06* | (2006.01) | |
| *C07D 401/04* | (2006.01) | |

(52) U.S. Cl.
CPC ........ *A61K 31/451* (2013.01); *A61K 31/4545* (2013.01); *A61P 3/06* (2018.01); *C07D 211/14* (2013.01); *C07D 401/04* (2013.01)

(58) Field of Classification Search
CPC ..... A61K 31/451; A61K 31/4545; A61P 3/06; C07D 211/14; C07D 401/04
See application file for complete search history.

(56) References Cited

U.S. PATENT DOCUMENTS

| | | |
|---|---|---|
| 4,064,245 A | 12/1977 | Beregi et al. |
| 5,236,934 A | 8/1993 | Vanatten |
| 5,441,946 A | 8/1995 | Pauls et al. |
| 5,462,947 A | 10/1995 | Svensson et al. |
| 5,556,990 A * | 9/1996 | Pauls ............... C07D 241/04 546/261 |
| 5,863,903 A | 1/1999 | Lundgren et al. |
| 5,866,513 A | 2/1999 | Michelotti et al. |
| 6,235,750 B1 * | 5/2001 | Lowe, III ............ A61P 27/06 546/264 |
| 6,503,905 B1 | 1/2003 | Liras et al. |
| 6,642,226 B2 | 11/2003 | Kolczewski et al. |
| 7,732,603 B2 | 6/2010 | McKenna |
| 7,750,012 B2 | 7/2010 | Sandanayaka et al. |
| 7,855,298 B2 | 12/2010 | Arista et al. |
| 8,088,760 B2 | 1/2012 | Chu et al. |
| 8,362,030 B2 | 1/2013 | Ingenito et al. |
| 8,470,816 B2 | 6/2013 | Ikeura et al. |
| 8,623,859 B2 | 1/2014 | Madden et al. |
| 8,673,850 B2 | 3/2014 | Seidah et al. |
| 8,697,736 B2 | 4/2014 | Penning et al. |
| 8,906,913 B2 | 12/2014 | Jain et al. |
| 9,126,976 B2 | 9/2015 | Anand et al. |
| 9,562,035 B2 | 2/2017 | Connolly et al. |
| 10,034,892 B2 | 7/2018 | Barta et al. |
| 10,233,186 B2 | 3/2019 | Brooijmans et al. |
| 10,287,317 B2 | 5/2019 | Muehlemann et al. |
| 10,307,433 B2 | 6/2019 | Barta et al. |
| 10,544,106 B2 | 1/2020 | Qian et al. |
| 10,568,882 B2 | 2/2020 | Barta et al. |
| 10,688,114 B2 | 6/2020 | Barta et al. |
| 10,710,980 B2 | 7/2020 | Li et al. |
| 10,821,106 B2 | 11/2020 | Barta et al. |
| 10,865,185 B2 | 12/2020 | Barta et al. |
| 10,980,801 B2 | 4/2021 | Barta et al. |
| 11,236,086 B2 | 2/2022 | Brubaker et al. |
| 11,345,679 B2 | 5/2022 | Yu et al. |
| 11,590,116 B2 | 2/2023 | Owens et al. |
| 11,708,359 B2 | 7/2023 | Ameriks et al. |
| 2004/0082641 A1 | 4/2004 | Rytved et al. |
| 2004/0229911 A1 | 11/2004 | Saltarelli et al. |
| 2004/0254120 A1 | 12/2004 | Fogleman et al. |
| 2006/0223875 A1 | 10/2006 | Skolnick et al. |
| 2007/0207985 A1 | 9/2007 | Li et al. |
| 2008/0058398 A1 | 3/2008 | Hamprecht et al. |
| 2008/0194621 A1 | 8/2008 | Lang |
| 2009/0203676 A1 | 8/2009 | Barba et al. |
| 2009/0221582 A1 | 9/2009 | Monck et al. |
| 2010/0113782 A1 | 5/2010 | Bolin et al. |

(Continued)

FOREIGN PATENT DOCUMENTS

| | | |
|---|---|---|
| CN | 103602337 * | 2/2014 |
| CN | 106995413 A | 8/2017 |

(Continued)

OTHER PUBLICATIONS

Kourounakis et al, 51(18) J. Med. Chem. 5861-5865 (2008) (Year: 2008).*
Annoura et al., "A Novel Class of Na+ and CA2+ Channel Dual Blockers with Highly Potent Ani-Ischemic Effects," Bioorganic and Medicinal Chemistry Letters 9 (1999), pp. 2999-3002.
Banker, et. al., (1996), Modern Pharmaceuticals, p. 596.
CAS Registry No. 57536-86-4; entry dated Mar. 25, 2005.
Database Registry, Chemical Abstracts Service, XP002768756, retrieved from STN Database accession No. 1770149-41-1, Jun. 1, 2015.
Database Registry, Chemical Abstracts Service, XP002768757, retrieved from STN Database accession No. 1796858-42-8, Jul. 8, 2015.
European Search Report and Opinion dated Jan. 2, 2019, for EP Patent Application No. 16839887.3. 9 pages.
Extended European Search Report for EP Application No. 16839890. 7, dated Mar. 20, 2019. 5 pages.

(Continued)

*Primary Examiner* — Timothy R Rozof
(74) *Attorney, Agent, or Firm* — Sheppard Mullin Richter & Hampton LLP

(57) ABSTRACT

The present disclosure relates to novel compounds capable of binding to PCSK9, thereby modulating PCSK9 biological activity. Also provided are compositions comprising these compounds, methods of preparing the compounds, and methods for use of the compounds in the treatment of PCSK9-related conditions and diseases.

7 Claims, No Drawings

(56) References Cited

U.S. PATENT DOCUMENTS

| | | |
|---|---|---|
| 2013/0064825 A1 | 3/2013 | Chan et al. |
| 2014/0045854 A1 | 2/2014 | Uesugi et al. |
| 2014/0093513 A1 | 4/2014 | Miline et al. |
| 2015/0051144 A1 | 2/2015 | Pingali et al. |
| 2015/0111857 A1 | 4/2015 | Hodous et al. |
| 2018/0237381 A1 | 8/2018 | Barta et al. |
| 2018/0250291 A1 | 9/2018 | Barta et al. |
| 2019/0119236 A1 | 4/2019 | Pandey et al. |
| 2020/0207718 A1 | 7/2020 | Barta et al. |
| 2020/0253958 A1 | 8/2020 | Barta et al. |
| 2021/0032214 A1 | 2/2021 | Pandey et al. |
| 2021/0038605 A1 | 2/2021 | Jin et al. |
| 2021/0236481 A1 | 8/2021 | Barta et al. |
| 2021/0309613 A1 | 10/2021 | Barta et al. |
| 2022/0047582 A1 | 2/2022 | Barta et al. |
| 2022/0117982 A1 | 4/2022 | Yang et al. |
| 2022/0193058 A1 | 6/2022 | Bowers et al. |
| 2022/0267269 A1 | 8/2022 | Bowers et al. |
| 2023/0113202 A1 | 4/2023 | Abbott et al. |
| 2023/0117611 A1 | 4/2023 | Moyer et al. |
| 2023/0158152 A1 | 5/2023 | Lei et al. |
| 2023/0174548 A1 | 6/2023 | Natarajan |
| 2023/0322695 A1 | 10/2023 | Liu et al. |

FOREIGN PATENT DOCUMENTS

| | | |
|---|---|---|
| CN | 112300074 A | 2/2021 |
| CN | 112430229 A | 3/2021 |
| CN | 112457297 A | 3/2021 |
| CN | 113637002 A | 11/2021 |
| CN | 114181196 A | 3/2022 |
| CN | 115611860 A | 1/2023 |
| CN | 116199618 A | 6/2023 |
| EP | 0378207 | 7/1990 |
| EP | 1987827 | 11/2008 |
| EP | 2170866 | 12/2008 |
| WO | WO 92/02501 | 2/1992 |
| WO | WO 95/00161 | 1/1995 |
| WO | WO 99/02502 | 1/1999 |
| WO | WO 99/28313 | 6/1999 |
| WO | WO 99/33839 A1 | 7/1999 |
| WO | WO 2000/071107 A1 | 11/2000 |
| WO | WO 01/96301 | 12/2001 |
| WO | WO 02/36123 | 5/2002 |
| WO | WO 2003/072558 | 9/2003 |
| WO | WO 2004/043929 | 5/2004 |
| WO | WO 2004/060882 | 7/2004 |
| WO | WO 2004/069792 | 8/2004 |
| WO | WO 2005/000309 | 1/2005 |
| WO | WO 2005/115361 | 12/2005 |
| WO | WO 2006/049597 | 5/2006 |
| WO | WO 2006/125665 | 11/2006 |
| WO | WO 2007/009741 | 1/2007 |
| WO | WO 2007/042962 | 4/2007 |
| WO | WO 2009/002469 | 12/2008 |
| WO | WO 2009/112832 A1 | 9/2009 |
| WO | WO 2011/051961 | 5/2011 |
| WO | WO 2012/039660 | 3/2012 |
| WO | WO 2012/154760 | 11/2012 |
| WO | WO 2013/028382 A1 | 2/2013 |
| WO | WO 2014/037313 A1 | 3/2014 |
| WO | WO 2014/037340 A1 | 3/2014 |
| WO | WO 2014/079364 A1 | 5/2014 |
| WO | WO 2014/101120 | 7/2014 |
| WO | WO 2014/101373 | 7/2014 |
| WO | WO 2014/105666 | 7/2014 |
| WO | WO 2014/127316 | 8/2014 |
| WO | WO 2014/128198 | 8/2014 |
| WO | WO 2014/150395 | 9/2014 |
| WO | WO 2014/150983 | 9/2014 |
| WO | WO 2015/024016 | 2/2015 |
| WO | WO 2016/029307 | 2/2016 |
| WO | WO 2016/107602 | 7/2016 |
| WO | WO 2016/107603 | 7/2016 |
| WO | WO 2017/100726 | 6/2017 |
| WO | WO 2018/026866 | 2/2018 |
| WO | WO 2018/165718 A1 | 9/2018 |
| WO | WO 2019/201123 A1 | 10/2019 |
| WO | WO 2020/252383 A2 | 12/2020 |
| WO | WO 2022/226665 A1 | 11/2022 |
| WO | WO 2022/226666 A1 | 11/2022 |
| WO | WO 2022/226668 A1 | 11/2022 |
| WO | WO 2022/235945 A1 | 11/2022 |
| WO | WO 2022/251280 A1 | 12/2022 |
| WO | WO 2023/120331 A1 | 6/2023 |
| WO | WO 2023/139379 A1 | 7/2023 |
| WO | WO 2023/146991 A1 | 8/2023 |
| WO | WO 2023/187715 A1 | 10/2023 |

OTHER PUBLICATIONS

Extended European Search Report for EP Application No. 16839893.1, dated Feb. 25, 2019. 10 pages.

International Search Report and Written Opinion for PCT/US2016/047816, dated Nov. 16, 2016. 10 pages.

International Search Report and Written Opinion for PCT/US2016/047810, dated Nov. 16, 2016. 6 pages.

International Search Report and Written Opinion for PCT/US2017/019189 dated Jul. 24, 2017, 13 pages.

International Search Report and Written Opinion in PCT/US2016/047798, dated Jan. 13, 2017. 8 pages.

Le Bourdonnec et al. Synthesis and Pharmacological Evaluation of Novel Octahydro-1H-pyrido[1,2-a]pyrazine as μ-Opioid Receptor Antagonists. Journal of Medicinal Chemistry, 49(25), 7290-7306 (2006).

Luhn et al., "Dissolution Profile of Novel Composite Pellet Cores Based on Different Ratios of Microcrystal line Cellulose and Isomalt," Journal of Pharmaceutical Sciences, vol. 101, Issue 8, pp. 2675-2680, 2012.

Pubchem CID 14819316 Create Date: Feb. 9, 2007. Retrieved from the Internet: <URL: https://pubchem.ncbi.nlm.nih.gov/compound/14819316>.

Pubchem CID 23519490 Create Date: Dec. 6, 2007 Date Accessed: Oct. 20, 2016, p. 3, compound listed. Retrieved from the Internet: URL: https://pubchem.ncbi.nlm.nih.gov/compound/23519490/>.

Pubchem CID 28917034 Create Date: May 28, 2009 p. 3, Fig. Retrieved from the Internet: <URL: https://pubchem.ncbi.nlm.nih.gov/compound/28917034>.

Pubchem—CID 73012351 Date Created: Mar. 7, 2014, p. 3 figure listed. Retrieved from the Internet: URL: https://pubchem.ncbi.nlm.nih.gov/compound/73012351>.

Sam et al., "Phenylisoquinolines and Hydroisoquinolines," Journal of Pharmaceutical Sciences, Jan. 1970, vol. 59, No. 1, 59-62.

STN Registry database entry for CAS RN 769101-76-0, entry date of Oct. 26, 2004, accessed Feb. 18, 2020.

STN Registry database for CAS RN 758671-90-8, entry date of Oct. 8, 2004, accessed Sep. 26, 2019.

Wolff et. al., "Burger's Medicinal Chemistry and Drug Discovery," 5th Ed. Part 1, pp. 975-977 (1995).

Duff, et al. PCSK9: an emerging target for treatment of hypercholesterolemia. Expert Opinion on Therapeutic Targets. 2011; 15(2):157-168.

Lewis, et al. Efficacy and safety of high-dose pravastatin in hypercholesterolemic patients with well-compensated chronic liver disease: Results of a prospective, randomized, double-blind, placebo-controlled, multicenter trial. Hepatology. 2007; 46(5):1453-1463.

Burns, et al. On the origin of the haouamine alkaloids. Angewandte Chemie, International Edition (2008):47(1), 205-208.

Huang, et al. Synthesis of Chiral Piperazines via Hydrogenation of Pyrazines Activated by Alkyl Halides. Organic Letters (2016), 18(13):3082-3085.

Jones, et al. Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors. Journal of Medicinal Chemistry (2009), 52(22):7170-7185.

(56) References Cited

OTHER PUBLICATIONS

Knezevic, et al. Proteome-wide Profiling of Clinical PARP Inhibitors Reveals Compound-Specific Secondary Targets. Cell Chemical Biology (2016), 23(12):1490-1503.
Lewis, et al. Amino Acid-Derived Heterocycles as Combinatorial Library Targets: Bicyclic Aminal Lactones. Journal of Combinatorial Chemistry (2003), 5(3):278-284.
Li et al. Palladium(II)-catalyzed asymmetric C-H carbonylation to diverse isoquinoline derivatives bearing all-carbon quaternary stereocenters. Chemical Communications (Cambridge, United Kingdom) (2020), 56(78):11605-11608.
Penning, et al. Optimization of Phenyl-Substituted Benzimidazole Carboxamide Poly(ADP-Ribose) Polymerase Inhibitors: Identification of (S)-2-(2-Fluoro-4-(pyrrolidin-2-yl)phenyl)-1H-benzimidazole-4-carboxamide (A-966492), a Highly Potent and Efficacious Inhibitor. Journal of Medicinal Chemistry (2010), 53(8):3142-3153.
Shintani, et al. Palladium-catalyzed asymmetric synthesis of 2-pyrrolidinones with a quaternary carbon stereocenter. Chemical Communications (Cambridge, United Kingdom) (2012), 48(79):9936-9938.
Sosnicki, et al. Divergent Synthesis of Functionalized Indenopyridin-2-ones and 2-Pyridones via Benzyl Group Transfer: Two Cases of Aza-semipinacol-Type Rearrangement. Organic Letters (2022), 24(46):8498-8502.
Wawer, et al. Structure-Activity Relationship Anatomy by Network-like Similarity Graphs and Local Structure-Activity Relationship Indices. Journal of Medicinal Chemistry (2008), 51(19):6075-6084.
Wu, et al. Oxyamination of Unactivated Alkenes with Electron-Rich Amines and Acids via a Catalytic Triiodide Intermediate. Organic Letters (2020), 22(3):884-890.
Zhao, et al. Quaternary Ammonium Salts as Chromophores for Exciton-Coupled Circular Dichroism: Absolute Configuration of Hypocholesterolemic Quinuclidines. Journal of the American Chemical Society (1995):117(29), 7844-5.
International Search Report and Written Opinion for PCT/US2020/037591 dated Feb. 3, 2021, 10 pages.
Pubchem, CID 135243294, Dec. 15, 2018, pp. 1-9, Retrieved from the Internet <URL : https://pubchem.ncbl.nlm.nih.gov/compound/135243294>; p. 2, formula.
Pubchem, CID 84050476, Oct. 20, 2014, pp. 1-8, Retrieved from the Internet <URL: https://pubchem.ncbi.nlm.nih.gov/ compound/84050476> ; p. 2, formula.

* cited by examiner

COMPOUNDS FOR THE MODULATION OF PROPROTEIN CONVERTASE SUBTILISIN/KEXIN TYPE 9 (PCSK9)

FIELD

The present disclosure relates to compounds capable of binding to proprotein convertase subtilisin/kexin type 9 (PCSK9) to modulate PCSK9's biological activity, compositions, and methods thereof.

BACKGROUND

Elevated plasma levels of low density lipoprotein cholesterol (LDL-C) represent a great risk factor for the development of coronary heart disease. Clearance of LDL-C from the plasma occurs primarily by the liver through the action of low density lipoprotein receptors (LDLRs), which are cell surface glycoproteins that bind to apolipoprotein B100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein receptor (LDLR) mediates efficient endocytosis of very low density lipoprotein (VLDL), VLDL remnants, and LDL. As part of the endocytic process, the LDLR releases lipoproteins into hepatic endosomes.

Proprotein convertase subtilisin/kexin type 9 (PCSK9) is an enzyme encoded by the PCSK9 gene in humans. PCSK9 is believed to play a regulatory role in cholesterol homeostasis. For example, PCSK9 can bind to the epidermal growth factor-like repeat A (EGF-A) domain of the low-density lipoprotein receptor (LDLR) resulting in LDLR internalization and degradation.

A drug that could modulate the activity of PCSK9 would be useful in controlling LDL-cholesterol levels. Therefore, there remains a need for compounds that are effective in the treatment and prevention of conditions and disorders associated with PCSK9, including hypercholesterolemia and hypocholesterolemia. The compounds provided herein bind to PCSK9, thereby modulating PCSK9 proprotein convertase enzyme activity, and can be used to treat and prevent PCSK9-associated conditions and disorders.

SUMMARY

Provided herein are compounds that are useful for binding and modulating PCSK9 enzyme activity. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated by PCSK9. Moreover, the disclosure provides uses of the compounds or compositions thereof in the manufacture of a medicament for the treatment of a disease, disorder or condition that is mediated, at least in part, by PCSK9.

Accordingly, provided, in one embodiment, is a compound of Formula I:

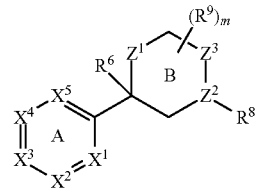

I or a pharmaceutically acceptable salt, prodrug, deuterated analog, stereoisomer, or mixture of stereoisomers thereof, wherein Ring A is a six-membered aromatic ring; $X^1$, $X^4$ and $X^5$ are independently N, CH or $CR^1$, $X^2$ is N, CH or $CR^2$, and $X^3$ is N, CH or $CR^3$, provided that no more than two of $X^1$, $X^2$, $X^3$, $X^4$ and $X^5$ are N, and at least one of $X^2$ and $X^3$ is other than N or CH;

Ring B is a six-membered non-aromatic ring; $Z^1$ is $CH_2$, $CHR^9$, $CR^9R^9$, NH, $NR^9$, O, or S, $Z^2$ is CH, $CR^{10}$, or N; and $Z^3$ is $CHR^7$, $CR^7R^9$, $NR^7$, O, or S; provided that when $Z^2$ is N, $Z^3$ is $CHR^7$ or $CR^7R^9$;

each $R^1$, $R^9$ or $R^{10}$ is independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$;

m is 0, 1, 2, 3 or 4;

one of $R^2$ and $R^3$ is $C_3$-$C_6$ cycloalkyl, phenyl, heteroaryl, or heterocyclyl, the other of $R^2$ and $R^3$ is H, $C_1$-$C_6$ alkyl, halo, OH, $C_1$-$C_6$ alkoxy, $C_1$-$C_6$ haloalkyl, $C_1$-$C_6$ hydroxyalkyl, CN, $NH_2$, $C_3$-$C_6$ cycloalkyl, phenyl, heteroaryl, or heterocyclyl, wherein the $C_3$-$C_6$ cycloalkyl, phenyl, heteroaryl, or heterocyclyl is optionally substituted with one to five $R^4$;

each $R^4$ is independently selected from $C_1$-$C_6$ alkyl, halo, OH, $C_1$-$C_6$ alkoxy, $C_1$-$C_6$ haloalkyl, $C_1$-$C_6$ hydroxyalkyl, $NH_2$ and CN;

$R^6$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^7$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^8$ is $C_1$-$C_6$ alkyl, $C_1$-$C_6$ heteroalkyl, $C_3$-$C_6$ cycloalkyl, heterocyclyl, aryl, heteroaryl, $C_3$-$C_6$ cycloalkyl-$C_1$-$C_6$ alkyl, aryl-$C_1$-$C_6$ alkyl, heteroaryl-$C_1$-$C_6$ alkyl, or heterocyclyl-$C_1$-$C_6$ alkyl; each of which is optionally substituted with one to four substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, =$NR^{11}$, CN, $NH_2$ and OH; or $R^8$ and $R^7$ together with the atoms to which they are attached form Ring C, which is a $C_3$-$C_6$ cycloalkyl or heterocyclyl ring fused with Ring B, wherein Ring C is optionally substituted with one to four $R^{12}$;

$R^{11}$ is H or $C_1$-$C_6$ alkyl;

each $R^{12}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; or two $R^{12}$ together with the atoms to which they are attached form Ring D, which is $C_3$-$C_6$ cycloalkyl or heterocyclyl fused with Ring C; or two $R^{12}$ on a same carbon atom form =O or =$NR^{11}$.

In one embodiment, provided is a compound of Formula I:

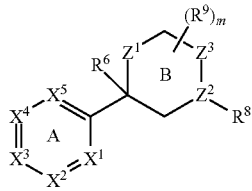

or a pharmaceutically acceptable salt, prodrug, deuterated analog, stereoisomer, or mixture of stereoisomers thereof, wherein Ring A is a six-membered aromatic ring; $X^1$, $X^4$ and $X^5$ are independently N, CH or $CR^1$, $X^2$ is N, CH or $CR^2$, and $X^3$ is N, CH or $CR^3$, provided that no more than three of $X^1$, $X^2$, $X^3$, $X^4$ and $X^5$ are N, and at least one of $X^2$ and $X^3$ is other than N or CH;

Ring B is a six-membered non-aromatic ring; $Z^1$ is $CH_2$, $CHR^9$, $CR^9R^9$, NH, $NR^9$, O, or S, $Z^2$ is CH, $CR^{10}$, or N; and $Z^3$ is $CHR^7$, $CR^7R^9$, $NR^7$, O, or S; provided that when $Z^2$ is N, $Z^3$ is $CHR^7$ or $CR^7R^9$;

each $R^1$, $R^9$ and $R^{10}$ is independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$;

m is 0, 1, 2, 3 or 4, and is not inclusive of $R^9$ groups at $Z^1$ or $Z^3$;

one of $R^2$ and $R^3$ is $C_3$-$C_6$ cycloalkyl, phenyl, heteroaryl, or heterocyclyl, the other of $R^2$ and $R^3$ is H, $C_1$-$C_6$ alkyl, halo, OH, $C_1$-$C_6$ alkoxy, $C_1$-$C_6$ haloalkyl, $C_1$-$C_6$ hydroxyalkyl, CN, $NH_2$, $C_3$-$C_6$ cycloalkyl, phenyl, heteroaryl, or heterocyclyl, wherein the $C_3$-$C_6$ cycloalkyl, phenyl, heteroaryl, or heterocyclyl is optionally substituted with one to five $R^4$;

each $R^4$ is independently selected from $C_1$-$C_6$ alkyl, halo, OH, $C_1$-$C_6$ alkoxy, $C_1$-$C_6$ haloalkyl, $C_1$-$C_6$ hydroxyalkyl, $NH_2$ and CN;

$R^6$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^7$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^8$ is $C_1$-$C_6$ alkyl, $C_1$-$C_6$ heteroalkyl, $C_3$-$C_6$ cycloalkyl, heterocyclyl, aryl, heteroaryl, $C_3$-$C_6$ cycloalkyl-$C_1$-$C_6$ alkyl, aryl-$C_1$-$C_6$ alkyl, heteroaryl-$C_1$-$C_6$ alkyl, or heterocyclyl-$C_1$-$C_6$ alkyl; each of which is optionally substituted with one to four substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, =$NR^{11}$, CN, $NH_2$ and OH; or $R^8$ and $R^7$ together with the atoms to which they are attached form Ring C, which is a $C_3$-$C_6$ cycloalkyl or heterocyclyl ring fused with Ring B, wherein Ring C is optionally substituted with one to four $R^{12}$;

$R^{11}$ is H or $C_1$-$C_6$ alkyl;

each $R^{12}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; or two $R^{12}$ together with the atoms to which they are attached form Ring D, which is $C_3$-$C_6$ cycloalkyl or heterocyclyl fused with Ring C; or two $R^{12}$ on a same carbon atom form =O or =$NR^{11}$.

In certain embodiments, provided is a compound selected from the compounds in Table 1, Table 2, or Table 3, or a pharmaceutically acceptable salt, prodrug, deuterated analog, stereoisomer, or mixture of stereoisomers thereof. In certain embodiments, provided is a compound selected from the compounds in Table 1, Table 2, Table 3, or Table 4, or a pharmaceutically acceptable salt, prodrug, deuterated analog, stereoisomer, or mixture of stereoisomers thereof. In some embodiments, the compound is

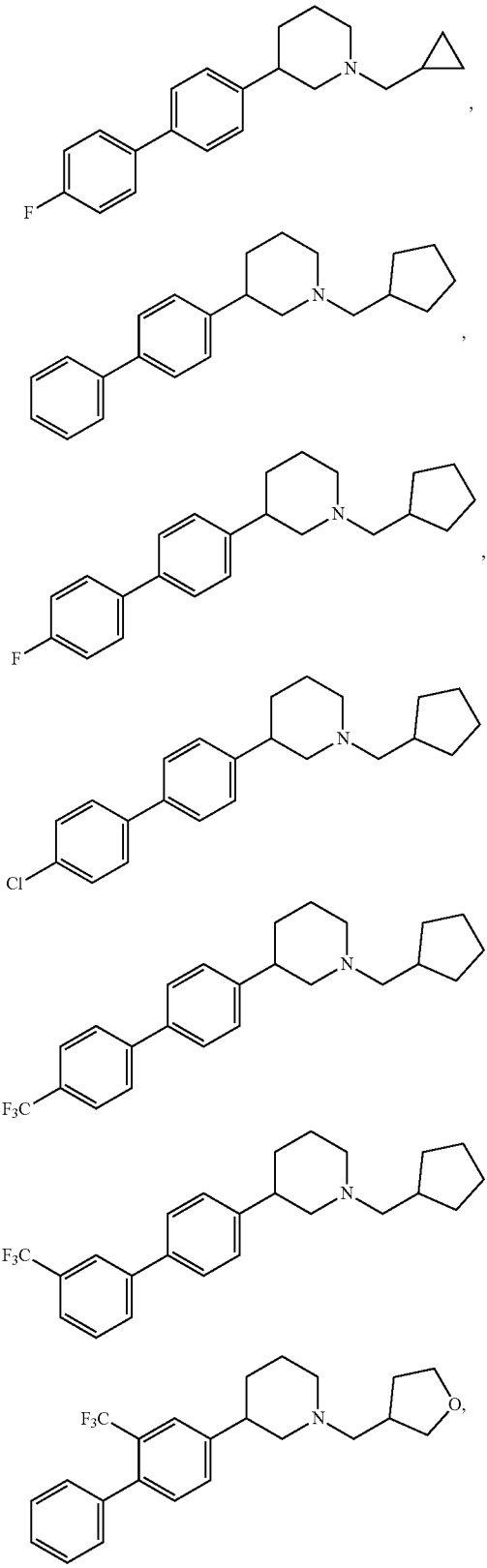

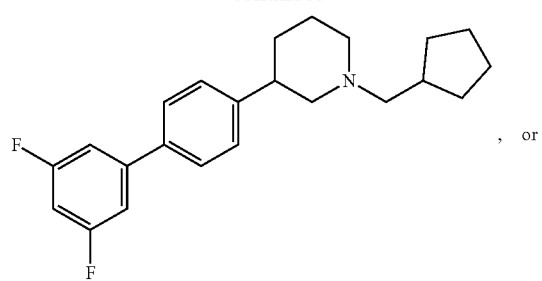
or a pharmaceutically acceptable salt, prodrug, deuterated analog, stereoisomer, or mixture of stereoisomers thereof.
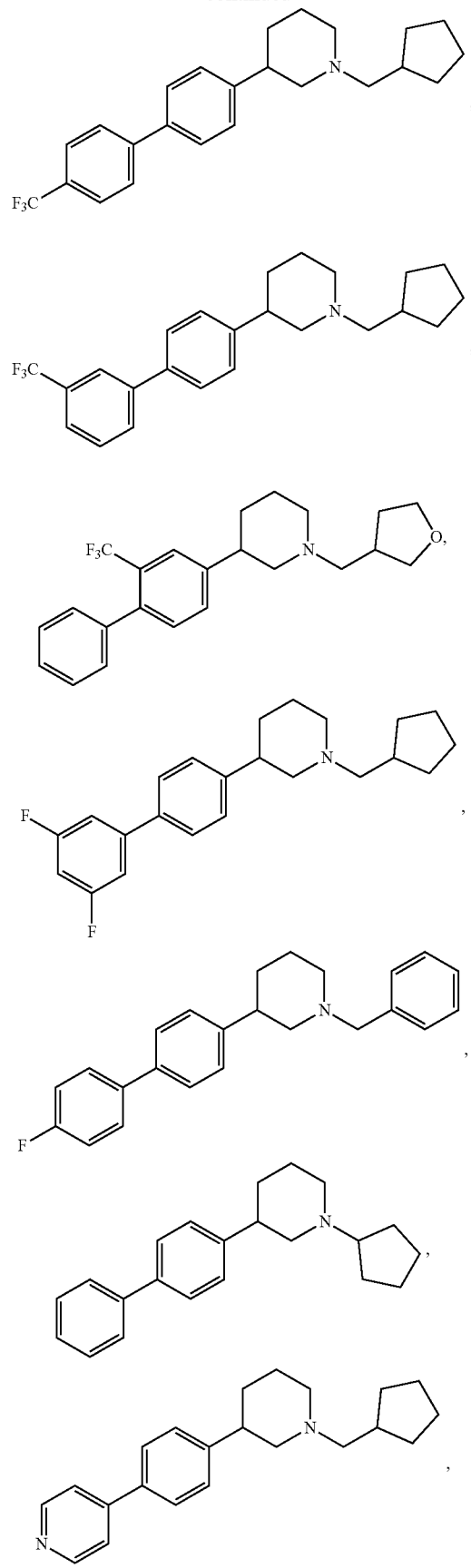

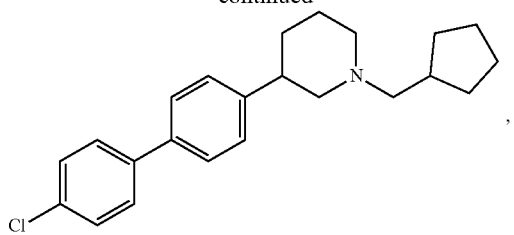

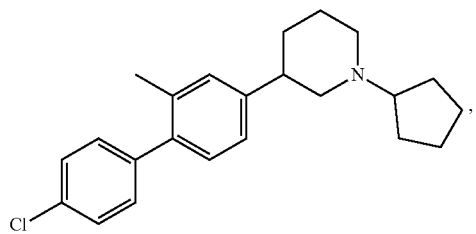

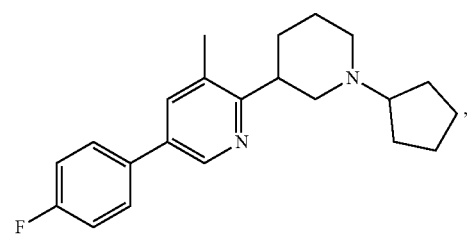

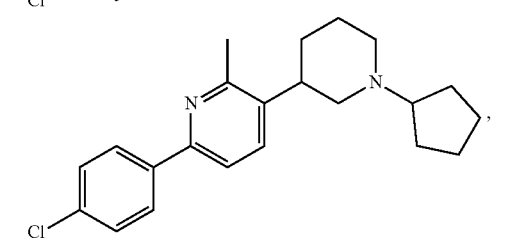

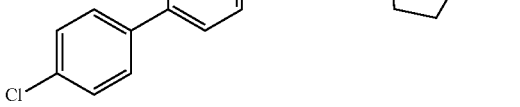

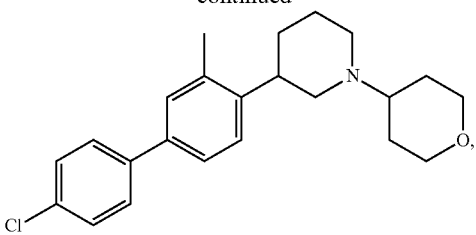

In some embodiments, provided is a compound selected from or a pharmaceutically acceptable salt, prodrug, deuterated analog, stereoisomer, or mixture of stereoisomers thereof.

In some embodiments, the compound is

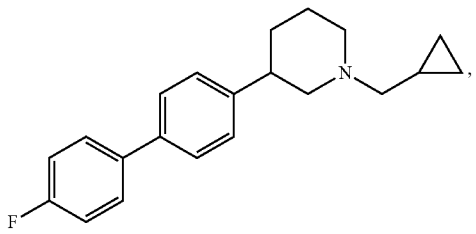 [SMILES: Fc1ccc(-c2ccc(C3CCCN(CC4CC4)C3)cc2)cc1]

or a pharmaceutically acceptable salt, prodrug, deuterated analog, stereoisomer, or mixture of stereoisomers thereof. In some embodiments, the compound is

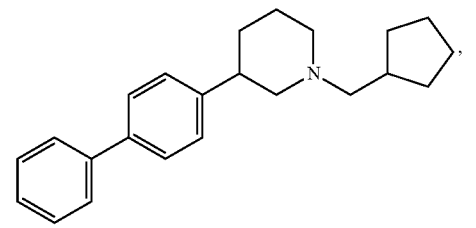 [SMILES: c1ccc(-c2ccc(C3CCCN(CC4CCCC4)C3)cc2)cc1]

or a pharmaceutically acceptable salt, prodrug, deuterated analog, stereoisomer, or mixture of stereoisomers thereof. In some embodiments, the compound is

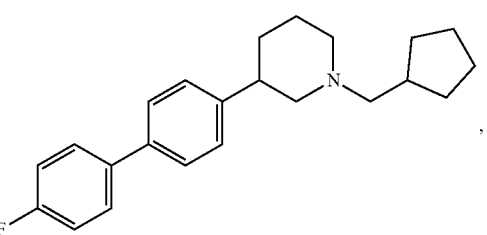

or a pharmaceutically acceptable salt, prodrug, deuterated analog, stereoisomer, or mixture of stereoisomers thereof. In some embodiments, the compound is

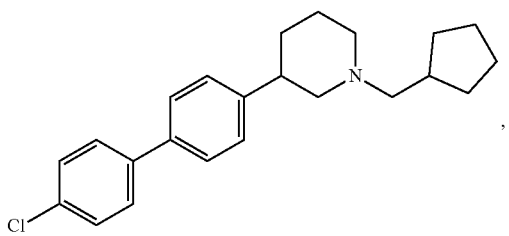 [SMILES: Clc1ccc(-c2ccc(C3CCCN(CC4CCCC4)C3)cc2)cc1]

or a pharmaceutically acceptable salt, prodrug, deuterated analog, stereoisomer, or mixture of stereoisomers thereof. In some embodiments, the compound is

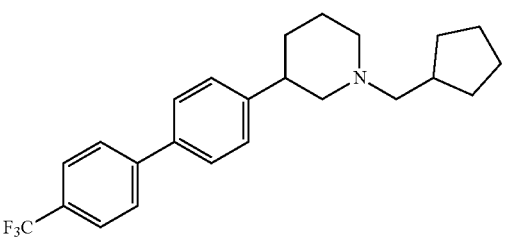

or a pharmaceutically acceptable salt, prodrug, deuterated analog, stereoisomer, or mixture of stereoisomers thereof. In some embodiments, the compound is

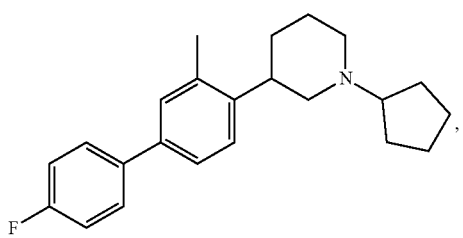 [SMILES: Cc1cc(-c2ccc(F)cc2)ccc1C1CCCN(C2CCCC2)C1]

or a pharmaceutically acceptable salt, prodrug, deuterated analog, stereoisomer, or mixture of stereoisomers thereof.

In certain embodiments, provided herein is a method of using a compound described herein or a pharmaceutically acceptable salt, prodrug, deuterated analog, stereoisomer, or mixture of stereoisomers thereof in the treatment of a disease or condition in a mammal that is mediated, at least in part, by PCSK9. Such diseases or conditions include cardiovascular diseases (e.g., coronary disease, hypertension, hypercholesterolemia, or atherosclerosis), a metabolic diseases (e.g., diabetes), hypocholesterolemia, a disease or condition where the mammal has elevated plasma levels of low density lipoprotein cholesterol, and a disease or condition where the mammal has suppressed plasma levels of low density lipoprotein cholesterol. Therefore, in certain embodiments, a compound described herein, or a pharmaceutically acceptable salt, prodrug, deuterated analog, isomer, or a mixture of isomers thereof is of use as a medicament for the treatment of the aforementioned diseases or conditions.

In certain embodiments, provided herein is a method of using a compound described herein, or a pharmaceutically acceptable salt, prodrug, deuterated analog, stereoisomer, or mixture of stereoisomers thereof to bind and modulate the biological activity of PCSK9 protein. In certain embodiments, provided herein is a method of using a compound described herein, or a pharmaceutically acceptable salt, prodrug, deuterated analog, stereoisomer, or mixture of stereoisomers thereof to bind and inhibit the biological activity of PCSK9 protein. In certain embodiments, provided herein is a compound described herein for use in the inhibition of PCSK9. In certain embodiments, provided herein is a compound described herein for use in the reduction of PCSK9-induced LDLR degradation. In certain embodiments, provided herein is a compound described herein for use in the treatment of hypercholesterolemia. In certain embodiments, provided herein is a compound described herein for use in the treatment of PCSK9-related disorders. In certain embodiments, provided herein is a compound described herein for use in the reduction of PCSK9 activity. In certain embodiments, provided herein is a compound described herein for use in treating allergies, asthma, cancer, cancer metastasis, inflammatory response to infection, or sepsis.

DETAILED DESCRIPTION

Before the present compositions and methods are described, it is to be understood that the disclosure is not limited to the particular compounds, compositions, methodologies, protocols, cell lines, assays, and reagents described, as these may vary. It is also to be understood that the terminology used herein is intended to describe particular embodiments of the present disclosure, and is in no way intended to limit the scope of the present disclosure as set forth in the appended claims.

1. Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_1$-6 alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, but are not limited to, methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —CH($CH_3$)$CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$). "Lower alkyl," as used herein, refers to an alkyl chain with 1 to 6 carbon atoms.

Certain commonly used alternative chemical names may be used. For example, a divalent group such as a divalent "alkyl" group, a divalent "aryl" group, etc., may also be referred to as an "alkylene" group, an "arylene" group, respectively. Also, unless indicated explicitly otherwise, where combinations of groups are referred to herein as one moiety, e.g. arylalkyl, the last mentioned group contains the atom by which the moiety is attached to the rest of the molecule. For example, "heterocyclylalkyl" refers to a heterocyclyl connected by an alkyl chain as a substituent wherein the alkyl chain is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, but are not limited to, ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, but are not limited to, methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl, or heteroaryl; each of which may be optionally substituted, as defined herein. Examples of acyl include, but are not limited to, formyl, acetyl, cyclohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aromatic" describes a ring or ring system that includes fully delocalized (throughout at least one ring of the ring or ring system) π and/or n electrons.

"Non-aromatic" describes a ring or ring system that does not include a ring having fully delocalized π and/or n electrons.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_6$-12 aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl" refers to —C(O)OH.

"Carboxyl ester" refers to both —OC(O)R and —C(O)OR, wherein R is alkyl, alkenyl, alkynyl, cycloalkyl, heterocyclyl, aryl, heteroalkyl, or heteroaryl; each of which may be optionally substituted, as defined herein.

"Carbocyclic" refers to a saturated, partially unsaturated or aromatic cyclic group having a single ring or multiple rings including fused, bridged, and spiro ring systems wherein all ring atoms are carbon.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. The term cycloalkyl is also intended to encompass any non-aromatic ring which may be fused to an aryl ring, regardless of the attachment to the remainder of the molecule. Further, the term "cycloalkylalkyl" refers to a cycloalkyl attached by an alkyl to the remainder of the molecule.

"Imino" refers to a group —C(NR)R, wherein each R is independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, for example, 1 to 5 halogens, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxyl group.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include, but are not limited to, —OCH$_3$, —CH$_2$OCH$_3$, —SCH$_3$, —CH$_2$SCH$_3$, —NRCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include, but are not limited to, pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). A "heteroaryl" group may be referred to as being "heteroaromatic". Heteroaryl does not encompass or overlap with aryl as defined above.

"Heterocyclyl" refers to a saturated or unsaturated non-aromatic cyclic alkyl group, with one or more ring heteroatoms independently selected from nitrogen, oxygen sulfur, and oxidized versions of nitrogen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) lactam (—NHCO) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, but are not limited to, pyrrolidinyl, piperidinyl, piperazinyl, oxetanyl, dioxolanyl, azetidinyl, and morpholinyl.

"Sulfonyl" refers to the group —S(O)$_2$R, where R is hydrogen, alkyl, alkenyl, alkynyl, cycloalkyl, heterocyclyl, aryl, heteroalkyl, or heteroaryl; each of which may be optionally substituted, as defined herein. Examples of sulfonyl groups include, but are not limited to, methylsulfonyl, ethylsulfonyl, phenylsulfonyl, and toluenesulfonyl.

"Sulfinyl" refers to the group —S(O)R, where R is hydrogen, alkyl, alkenyl, alkynyl, cycloalkyl, heterocyclyl, aryl, heteroalkyl, or heteroaryl; each of which may be optionally substituted, as defined herein. Examples of sulfinyl groups include, but are not limited to, methylsulfinyl, ethylsulfinyl, phenylsulfinyl, and toluenesulfinyl.

"Alkylsulfonyl" refers to the group —S(O)$_2$R, where R is alkyl.

"Alkylsulfinyl" refers to the group —S(O)R, where R is alkyl.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H and $^{14}$C are incorporated, may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to x hydrogens attached to a carbon atom is/are replaced by deuterium, in which x is the number of hydrogens in the molecule. Such compounds may exhibit increased resistance to metabolism and are thus useful for increasing the half-life of any compound described herein when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, or $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. In the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts of the compound (or prodrug, deuterated analog, stereoisomer, or mixture of stereoisomers) with inorganic acids or organic acids. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise all tautomers or each tautomer of the compounds. Thus, the amide containing compounds are understood to include their imidic acid tautomers. Likewise, the imidic acid containing compounds are understood to include their amide tautomers.

"Stereoisomers" are isomers that differ only in the way the atoms are arranged in space and include enantiomers and diastereomers.

"Enantiomers" are a pair of stereoisomers that are non-superimposable mirror images of each other. A 1:1 mixture of a pair of enantiomers is a "racemic" mixture.

"Diastereoisomers" are stereoisomers that have at least two asymmetric atoms, but which are not mirror-images of each other.

"Prodrugs" means any compound which releases an active parent drug according described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl or sulfhydryl group in a compound described herein is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds described herein, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

2. List of Abbreviations and Acronyms

| Abbreviation | Meaning |
| --- | --- |
| Ac | acetyl |
| ACN | acetonitrile |
| BH$_3$Me$_2$S (or BMS) | borane dimethyl sulfide |
| PIN | pinacolato |
| DMF | dimethylformamide |
| DMSO | dimethylsulfoxide |

-continued

| Abbreviation | Meaning |
| --- | --- |
| dppf | diphenylphosphino ferrocene |
| Et | ethyl |
| EtOAc | ethyl acetate |
| h or hrs | hours |
| HPLC | High performance liquid chromatography |
| LC-MS | liquid chromatography-mass spectrometry |
| Lg | Leaving group |
| Me | methyl |
| min | minute |
| MS | mass spectrometry |
| M + H | mass peak plus hydrogen |
| m/z | mass/charge |
| OAc | acetate |
| OMs | methanesulfonate |
| OTf | trifluoromethanesulfonate |
| OTs | p-toluenesulfonate |
| Pd(PPh$_3$)$_4$ | tetrakis(triphenylphosphine)palladium(0) |
| Pd/C | palladium on carbon |
| Ph | phenyl |
| psi | pounds per square inch |
| Pt/C | platinum on carbon |
| THF | tetrahydrofuran |

3. Compounds

Provided herein are compounds that are useful for binding PCSK9. In one embodiment, provided is a compound of Formula I:

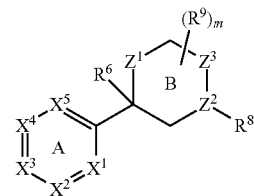

I or a pharmaceutically acceptable salt, prodrug, deuterated analog, stereoisomer, or mixture of stereoisomers thereof, wherein Ring A is a six-membered aromatic ring; $X^1$, $X^4$ and $X^5$ are independently N, CH or $CR^1$, $X^2$ is N, CH or $CR^2$, and $X^3$ is N, CH or $CR^3$, provided that no more than two of $X^1$, $X^2$, $X^3$, $X^4$ and $X^5$ are N, and at least one of $X^2$ and $X^3$ is other than N or CH;

Ring B is a six-membered non-aromatic ring; $Z^1$ is $CH_2$, $CHR^9$, $CR^9R^9$, NH, $NR^9$, O, or S, $Z^2$ is CH, $CR^{10}$, or N; and $Z^3$ is $CHR^7$, $CR^7R^9$, $NR^7$, O, or S; provided that when $Z^2$ is N, $Z^3$ is $CHR^7$ or $CR^7R^9$;

each $R^1$, $R^9$ or $R^{10}$ is independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$;

m is 0, 1, 2, 3 or 4;

one of $R^2$ and $R^3$ is $C_3$-$C_6$ cycloalkyl, phenyl, heteroaryl, or heterocyclyl, the other of $R^2$ and $R^3$ is H, $C_1$-$C_6$ alkyl, halo, OH, $C_1$-$C_6$ alkoxy, $C_1$-$C_6$ hydroxyalkyl, $C_1$-$C_6$ haloalkyl, CN, $NH_2$, $C_3$-$C_6$ cycloalkyl, phenyl, heteroaryl, or heterocyclyl, wherein the $C_3$-$C_6$ cycloalkyl, phenyl, heteroaryl, or heterocyclyl is optionally substituted with one to five $R^4$;

each $R^4$ is independently selected from $C_1$-$C_6$ alkyl, halo, OH, $C_1$-$C_6$ alkoxy, $C_1$-$C_6$ haloalkyl, $C_1$-$C_6$ hydroxyalkyl, $NH_2$ and CN;

$R^6$ is H, halo, $C_1$-$C_6$ alkyl, $C_1$-$C_6$ alkoxy, $C_1$-$C_6$ haloalkyl, $C_1$-$C_6$ hydroxyalkyl, OH, CN, or $NH_2$;

$R^7$ is H, halo, $C_1$-$C_6$ alkyl, $C_1$-$C_6$ alkoxy, $C_1$-$C_6$ haloalkyl, $C_1$-$C_6$ hydroxyalkyl, OH, CN, or $NH_2$;

$R^8$ is $C_1$-$C_6$ alkyl, $C_1$-$C_6$ heteroalkyl, $C_3$-$C_6$ cycloalkyl, heterocyclyl, aryl, heteroaryl, $C_3$-$C_6$ cycloalkyl-$C_1$-$C_6$ alkyl, aryl-$C_1$-$C_6$ alkyl, heteroaryl-$C_1$-$C_6$ alkyl, or heterocyclyl-$C_1$-$C_6$ alkyl; each of which is optionally substituted with one to four substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH; or $R^8$ and $R^7$ together with the atoms to which they are attached form Ring C, which is a $C_3$-$C_6$ cycloalkyl or heterocyclyl ring fused with Ring B, wherein Ring C is optionally substituted with one to four $R^{12}$;

$R^{11}$ is H or $C_1$-$C_6$ alkyl;

each $R^{12}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; or two $R^{12}$ together with the atoms to which they are attached form Ring D, which is $C_3$-$C_6$ cycloalkyl or heterocyclyl fused with Ring C; or two $R^{12}$ on a same carbon atom form $=O$ or $=NR^{11}$.

In some embodiments, no more than three of $X^1$, $X^2$, $X^3$, $X^4$ and $X^5$ are N.

In some embodiments, m is not inclusive of $R^9$ groups at $Z^1$ or $Z^3$. In some embodiments, m is 0, 1, 2, 3 or 4, and is not inclusive of $R^9$ groups at $Z^1$ or $Z^3$. In some embodiments, $Z^1$ is $CH_2$, $CHR^{9a}$, $CR^{9a}R^{9a}$, NH, $NR^{9a}$, O, or S, $Z^2$ is CH, $CR^{10}$, or N; and $Z^3$ is $CHR^7$, $CR^7R^{9a}$, $NR^7$, O, or S; provided that when $Z^2$ is N, $Z^3$ is $CHR^7$ or $CR^7R^{9a}$, wherein $R^{9a}$ is independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$, provided that $R^{9a}$ is not halo when bonded to N. In some embodiments, $R^{9a}$ is $R^9$.

In some embodiments, each $R^1$, $R^9$ or $R^{10}$ is independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$, provided that $R^1$, $R^9$ and $R^{10}$ are not halo when bonded to N.

In some embodiments, $Z^3$ is $CHR^7$. In some embodiments, $Z^3$ is $CR^7R^9$. In some embodiments, $Z^3$ is $NR^7$. In some embodiments, $R^7$ is H. In some embodiments, $Z^3$ is O. In some embodiments, $Z^3$ is S.

In some embodiments, $R^7$ is H.

In some embodiments, $R^8$ is $C_1$-$C_6$ alkyl, $C_1$-$C_6$ heteroalkyl, $C_3$-$C_6$ cycloalkyl, heterocyclyl, aryl, heteroaryl, $C_3$-$C_6$ cycloalkyl-$C_1$-$C_6$ alkyl, aryl-$C_1$-$C_6$ alkyl, heteroaryl-$C_1$-$C_6$ alkyl, or heterocyclyl-$C_1$-$C_6$ alkyl; each of which is optionally substituted with one or two substituents independently selected from $C_1$-$C_6$ alkyl, $C_1$-$C_6$ alkoxy, $C_1$-$C_6$ haloalkyl, halo, oxo, $=NR^{11}$, CN, $NH_2$ and OH.

In some embodiments, $R^8$ is unsubstituted $C_1$-$C_6$ alkyl. In some embodiments, $R^8$ is unsubstituted $C_1$-$C_6$ heteroalkyl. In some embodiments, $R^8$ is unsubstituted $C_3$-$C_6$ cycloalkyl. In some embodiments, $R^8$ is unsubstituted heterocyclyl. In some embodiments, $R^8$ is unsubstituted aryl. In some embodiments, $R^8$ is unsubstituted heteroaryl. In some embodiments, $R^8$ is unsubstituted $C_3$-$C_6$ cycloalkyl-$C_1$-$C_6$ alkyl. In some embodiments, $R^8$ is unsubstituted aryl-$C_1$-$C_6$ alkyl. In some embodiments, $R^8$ is unsubstituted heteroaryl-$C_1$-$C_6$ alkyl. In some embodiments, $R^8$ is unsubstituted heterocyclyl-$C_1$-$C_6$ alkyl.

In some embodiments, $R^8$ is $C_1$-$C_6$ alkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is $C_1$-$C_6$ heteroalkyl substituted with one substituent selected from $C_1$-$C_6$ alkyl, $C_1$-$C_6$ alkoxy, $C_1$-$C_6$ haloalkyl, halo, oxo, $=NR^{11}$, CN, $NH_2$ and OH. In some embodiments, $R^8$ is $C_3$-$C_6$ cycloalkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is heterocyclyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is aryl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH. In some embodiments, $R^8$ is heteroaryl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH. In some embodiments, $R^8$ is $C_3$-$C_6$ cycloalkyl-$C_1$-$C_6$ alkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is aryl-$C_1$-$C_6$ alkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is heteroaryl-$C_1$-$C_6$ alkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^8$ is heterocyclyl-$C_1$-$C_6$ alkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH.

In some embodiments, $R^8$ and $R^7$ together with the atoms to which they are attached form Ring C, which is a $C_3$-$C_6$ cycloalkyl or 3- to 6-membered heterocyclyl ring fused with Ring B, wherein Ring C is optionally substituted with one to four $R^{12}$.

In some embodiments, Ring C is unsubstituted.
In some embodiments, Ring C is substituted with one $R^{12}$.
In some embodiments, Ring C is substituted with two $R^{12}$.
In some embodiments, each $R^{12}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN.

In some embodiments, two $R^{12}$ together with the atoms to which they are attached form Ring D, which is $C_3$-$C_6$ cycloalkyl or 3- to 6-membered heterocyclyl fused with Ring C.

In some embodiments, two $R^{12}$ on a same carbon atom form $=O$ or $=NR^{11}$.

In some embodiments, provided is a compound of Formula II or III:

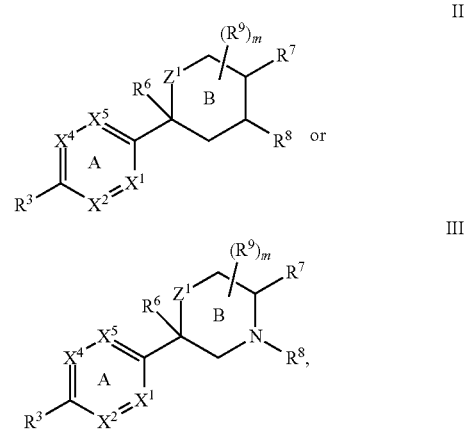

or a pharmaceutically acceptable salt, prodrug, deuterated analog, stereoisomer, or mixture of stereoisomers thereof, wherein
  $R^3$ is $C_3$-$C_6$ cycloalkyl, phenyl, 5- or 6-membered heteroaryl, or 5- or 6-membered heterocyclyl, wherein the $C_3$-$C_6$ cycloalkyl, phenyl, 5- or 6-membered heteroaryl, or 3- to 6-membered heterocyclyl is optionally substituted with one to five $R^4$,
  each $R^4$ is independently selected from $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; and
  Ring A, Ring B, m, $X^1$, $X^2$, $X^4$, $X^5$, $R^6$, $R^7$, $R^8$, $R^9$, and $Z^1$ are as defined herein.

In some embodiments, provided is a compound of Formula IV or V:

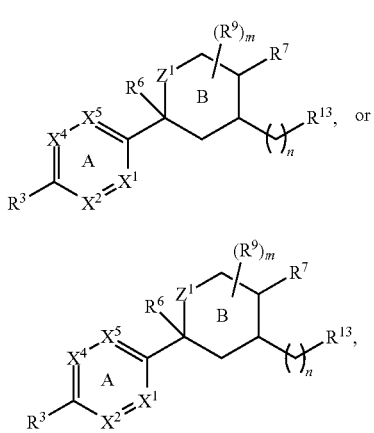

or a pharmaceutically acceptable salt, prodrug, deuterated analog, stereoisomer, or mixture of stereoisomers thereof, wherein
  $R^3$ is $C_3$-$C_6$ cycloalkyl, phenyl, 5- or 6-membered heteroaryl, or 3- to 6-membered heterocyclyl, wherein the $C_3$-$C_6$ cycloalkyl, phenyl, 5- or 6-membered heteroaryl, or 3- to 6-membered heterocyclyl are optionally substituted with one to five $R^4$,
  each $R^4$ is independently selected from $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN;
  n is 0, 1 or 2;
  $R^7$ is H, halo, $C_1$-$C_6$ alkyl, $C_1$-$C_6$ alkoxy, $C_1$-$C_6$ haloalkyl, OH, CN, or $NH_2$;
  $R^{13}$ is $C_3$-$C_6$ cycloalkyl, phenyl, 5- or 6-membered heteroaryl, or 3- to 6-membered heterocyclyl, wherein the $C_3$-$C_6$ cycloalkyl, phenyl, 5- or 6-membered heteroaryl, or 3- to 6-membered heterocyclyl is optionally substituted with one or two substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH; and
  Ring A, Ring B, m, $X^1$, $X^2$, $X^4$, $X^5$, $R^6$, $R^9$, and $Z^1$ are as defined herein.

In some embodiments, $R^7$ is H.
In some embodiments, n is 0. In some embodiments, n is 1.
In some embodiments, $R^{13}$ is unsubstituted $C_3$-$C_6$ cycloalkyl. In some embodiments, $R^{13}$ is unsubstituted heterocyclyl. In some embodiments, $R^{13}$ is unsubstituted aryl. In some embodiments, $R^{13}$ is unsubstituted heteroaryl.

In some embodiments, $R^{13}$ is $C_3$-$C_6$ cycloalkyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^{13}$ is heterocyclyl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^{13}$ is aryl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH. In some embodiments, $R^{13}$ is heteroaryl substituted with one substituent selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH.

In some embodiments, $R^{13}$ is $C_3$-$C_6$ cycloalkyl substituted with two substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^{13}$ is heterocyclyl substituted with two substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, $=NR^{11}$, CN, $NH_2$ and OH. In some embodiments, $R^{13}$ is aryl substituted with two substituents independently selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH. In some embodiments, $R^{13}$ is heteroaryl substituted with two substituents independently selected from $C_1$-$C_6$ alkyl, $C_1$-$C_6$ alkoxy, $C_1$-$C_6$ hydroxyalkyl, $C_1$-$C_6$ haloalkyl, halo, CN, $NH_2$ and OH.

In some embodiments, provided is a compound of Formula VI or VII:

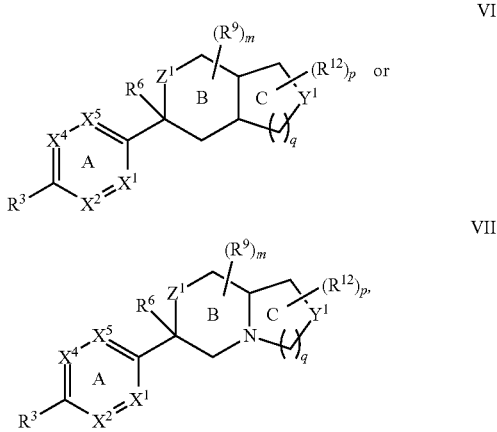

or a pharmaceutically acceptable salt, prodrug, deuterated analog, stereoisomer, or mixture of stereoisomers thereof, wherein
  $R^3$ is $C_3$-$C_6$ cycloalkyl, phenyl, 5- or 6-membered heteroaryl, or 5- or 6-membered heterocyclyl, wherein the $C_3$-$C_6$ cycloalkyl, phenyl, 5- or 6-membered heteroaryl, or 5- or 6-membered heterocyclyl are optionally substituted with one to five $R^4$,
  each $R^4$ is independently selected from $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN;
  $Y^1$ is O, S, SO, $SO_2$, $CH_2$, $CHR^{12}$, $CR^{12}R^{12}$, NH or $NR^{12}$;
  p is 0, 1, 2, 3, or 4; provided that the total number of $R^{12}$ is not more than 4;
  q is 0, 1 or 2; and
  Ring A, Ring B, Ring C, m, $X^1$, $X^2$, $X^4$, $X^5$, $R^6$, $R^9$, $R^{12}$, and $Z^1$ are as defined herein.

In some embodiments, provided is a compound of Formula VIII:

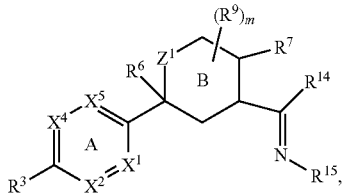

VIII or a pharmaceutically acceptable salt, prodrug, deuterated analog, stereoisomer, or mixture of stereoisomers thereof, wherein
$R^3$ is $C_3$-$C_6$ cycloalkyl, phenyl, 5- or 6-membered heteroaryl, or 5- or 6-membered heterocyclyl, wherein the $C_3$-$C_6$ cycloalkyl, phenyl, 5- or 6-membered heteroaryl, or 5- or 6-membered heterocyclyl are optionally substituted with one to five $R^4$,
each $R^4$ is independently selected from $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN;
$R^7$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;
$R^{14}$ is H, $C_1$-$C_5$ alkyl, $C_1$-$C_5$ heteroalkyl, $C_3$-$C_6$ cycloalkyl, heterocyclyl, aryl, or heteroaryl; each of which is optionally substituted with one substituent selected from $C_1$-$C_6$ alkyl, $C_1$-$C_6$ alkoxy, $C_1$-$C_6$ haloalkyl, halo, oxo, $=NR^{11}$, CN, $NH_2$ and OH;
$R^{15}$ is H or $C_1$-$C_6$ alkyl; or
$R^7$ and $R^{14}$ together with the atoms to which they are attached form $C_3$-$C_6$ cycloalkyl or 5- or 6-membered heterocyclyl optionally substituted with one or two $R^{12}$; or
$R^{14}$ is H, and $R^7$ and $R^{15}$ together with the atoms to which they are attached form 5- or 6-membered heterocyclyl optionally substituted with one to four $R^{12}$; or
$R^{14}$ and $R^{15}$ together with the atoms to which they are attached form 5- or 6-membered heteroaryl or 5- or 6-membered heterocyclyl optionally substituted with one to four $R^{16}$; or
$R^7$ and $R^{14}$ together with the atoms to which they are attached, and $R^{14}$ and $R^{15}$ together with the atoms to which they are attached form a fused bicyclic heterocyclyl optionally substituted with one or two $R^{16}$;
each $R^{16}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; and
Ring A, Ring B, m, $X^1$, $X^2$, $X^4$, $X^5$, $R^6$, $Z^1$, $R^9$, and $R^{12}$ are as defined herein.
In some embodiments, provided is a compound of Formula IX:

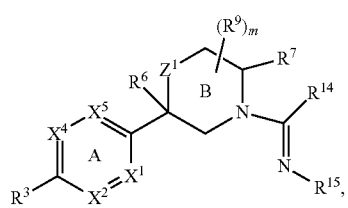

IX or a pharmaceutically acceptable salt, prodrug, deuterated analog, stereoisomer, or mixture of stereoisomers thereof, wherein
$R^3$ is $C_3$-$C_6$ cycloalkyl, phenyl, 5- or 6-membered heteroaryl, or 5- or 6-membered heterocyclyl, wherein the $C_3$-$C_6$ cycloalkyl, phenyl, 5- or 6-membered heteroaryl, or 5- or 6-membered heterocyclyl are optionally substituted with one to five $R^4$,
each $R^4$ is independently selected from $C_1$-$C_6$ alkyl, halo, OH, $C_1$-$C_6$ alkoxy, $C_1$-$C_6$ haloalkyl, $NH_2$ and CN;
$R^7$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;
$R^{14}$ is H, $C_1$-$C_5$ alkyl, $C_1$-$C_5$ heteroalkyl, $C_3$-$C_6$ cycloalkyl, heterocyclyl, aryl, or heteroaryl; each of which is optionally substituted with one or two substituents independently selected from $C_1$-$C_6$ alkyl, $C_1$-$C_6$ alkoxy, $C_1$-$C_6$ haloalkyl, halo, oxo, $=NR^{11}$, CN, $NH_2$ and OH;
$R^{15}$ is H or $C_1$-$C_6$ alkyl; or
$R^7$ and $R^{14}$ together with the atoms to which they are attached form 5- or 6-membered heterocyclyl optionally substituted with one or two $R^{12}$; or
$R^{14}$ is H, $R^7$ and $R^{15}$ together with the atoms to which they are attached form 5- or 6-membered heterocyclyl optionally substituted with one to four $R^{12}$; or
$R^{14}$ and $R^{15}$ together with the atoms to which they are attached form 5- or 6-membered heteroaryl or 5- or 6-membered heterocyclyl optionally substituted with one to four $R^{16}$; or
$R^7$ and $R^{14}$ together with the atoms to which they are attached, and $R^{14}$ and $R^{15}$ together with the atoms to which they are attached form a fused bicyclic heterocyclyl optionally substituted with one or two $R^{16}$;
each $R^{16}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; and
Ring A, Ring B, m, $X^1$, $X^2$, $X^4$, $X^5$, $R^6$, $Z^1$, $R^9$, and $R^{12}$ are as defined herein.
In some embodiments, $X^1$, $X^4$ and $X^5$ are CH or $CR^1$, and $X^2$ is CH or $CR^2$. In some embodiments, $X^1$, $X^4$ and $X^5$ are CH or $CR^1$, and $X^2$ is N. In some embodiments, $X^1$ is N, $X^4$ and $X^5$ are CH or $CR^1$, and $X^2$ is CH or $CR^2$. In some embodiments, $X^4$ is N, $X^1$ and $X^5$ are CH or $CR^1$, and $X^2$ is CH or $CR^2$. In some embodiments, $X^5$ is N, $X^1$ and $X^4$ are CH or $CR^1$, and $X^2$ is CH or $CR^2$. In some embodiments, $R^1$ is $CH_3$, $CF_3$, F, or Cl. In some embodiments, $R^2$ is $CH_3$, $CF_3$, F, Cl, phenyl or 5- or 6-membered heteroaryl optionally substituted with one to five $R^4$.

In some embodiments, $X^2$ is N, CH or $CR^2$, $R^2$ is $CH_3$, $CF_3$, F, Cl, phenyl or 5- or 6-membered heteroaryl optionally substituted with one to five $R^4$, $X^3$ is $CR^3$, and $R^3$ is phenyl or 5- or 6-membered heteroaryl optionally substituted with one to five $R^4$. In some embodiments, $X^2$ is $CR^2$, $R^2$ is phenyl or 5- or 6-membered heteroaryl optionally substituted with one to five $R^4$, $X^3$ is N, CH or $CR^3$, and $R^3$ is $CH_3$, $CF_3$, F, Cl, phenyl optionally substituted with one to five $R^4$, or 5- or 6-membered heteroaryl optionally substituted with one to four $R^4$.

In some embodiments, one of $R^2$ and $R^3$ is $C_3$-$C_6$ cycloalkyl, phenyl, 5- or 6-membered heteroaryl, or 3- to 6-membered heterocyclyl, the other of $R^2$ and $R^3$ is H, $C_1$-$C_6$ alkyl, halo, OH, $C_1$-$C_6$ alkoxy, $C_1$-$C_6$ haloalkyl, CN, $NH_2$, $C_3$-$C_6$ cycloalkyl, phenyl, 5- or 6-membered heteroaryl, or 3- to 6-membered heterocyclyl, wherein the $C_3$-$C_6$ cycloalkyl, phenyl, 5- or 6-membered heteroaryl, or 3- to 6-membered heterocyclyl is optionally substituted with one to five $R^4$.

In some embodiments, $R^3$ is phenyl optionally substituted with one to five $R^4$ or 5- or 6-membered heteroaryl optionally substituted with one to five $R^4$. In some embodiments, $R^3$ is phenyl optionally substituted with one $R^4$. In some embodiments, $R^3$ is 5- or 6-membered heteroaryl optionally substituted with one $R^4$.

In some embodiments, each $R^4$ independently is $CH_3$, $CF_3$, OH, F, or Cl.

In some embodiments, provided is a compound of Formula Ia:

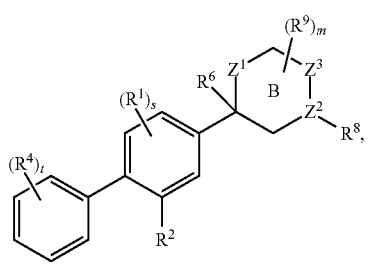

Ia or a pharmaceutically acceptable salt, prodrug, deuterated analog, stereoisomer, or mixture of stereoisomers thereof, wherein s is 0, 1, 2, or 3, t is 0, 1, 2, 3, 4, or 5, and other variables are as defined herein.

In some embodiments, provided is a compound of Formula IIa:

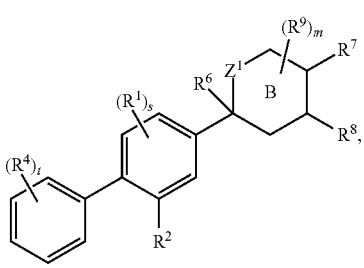

IIa or a pharmaceutically acceptable salt, prodrug, deuterated analog, stereoisomer, or mixture of stereoisomers thereof, wherein s is 0, 1, 2, or 3, t is 0, 1, 2, 3, 4, or 5, and other variables are as defined herein.

In some embodiments, provided is a compound of Formula IIIa:

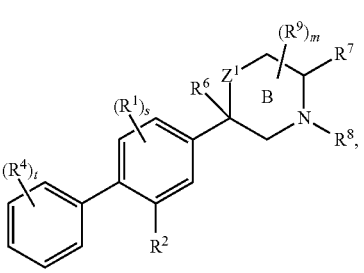

IIIa or a pharmaceutically acceptable salt, prodrug, deuterated analog, stereoisomer, or mixture of stereoisomers thereof, wherein s is 0, 1, 2, or 3, t is 0, 1, 2, 3, 4, or 5, and other variables are as defined herein.

In some embodiments, provided is a compound of Formula IVa:

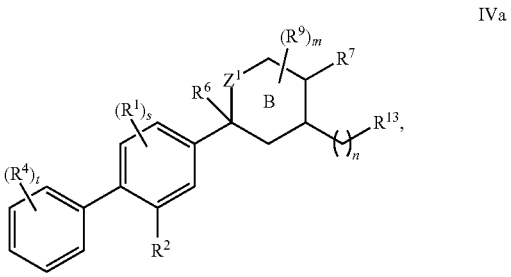

IVa or a pharmaceutically acceptable salt, prodrug, deuterated analog, stereoisomer, or mixture of stereoisomers thereof, wherein s is 0, 1, 2, or 3, t is 0, 1, 2, 3, 4, or 5;

$R^7$ is H, halo, $C_1$-$C_6$ alkyl, $C_1$-$C_6$ alkoxy, $C_1$-$C_6$ haloalkyl, OH, CN, or $NH_2$;

$R^{13}$ is $C_3$-$C_6$ cycloalkyl, phenyl, 5- or 6-membered heteroaryl, or 3- to 6-membered heterocyclyl, wherein the $C_3$-$C_6$ cycloalkyl, phenyl, 5- or 6-membered heteroaryl, or 3- to 6-membered heterocyclyl is optionally substituted with one or two substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, =$NR^{11}$, CN, $NH_2$ and OH; and other variables are as defined herein.

In some embodiments, provided is a compound of Formula Va:

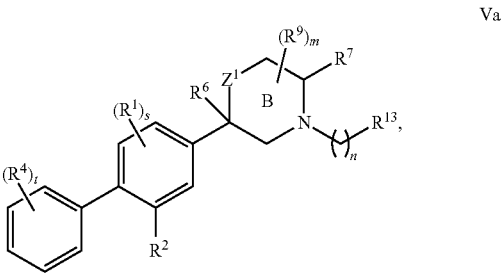

Va or a pharmaceutically acceptable salt, prodrug, deuterated analog, stereoisomer, or mixture of stereoisomers thereof, wherein s is 0, 1, 2, or 3, t is 0, 1, 2, 3, 4, or 5;

$R^7$ is H, halo, $C_1$-$C_6$ alkyl, $C_1$-$C_6$ alkoxy, $C_1$-$C_6$ haloalkyl, OH, CN, or $NH_2$;

$R^{13}$ is $C_3$-$C_6$ cycloalkyl, phenyl, 5- or 6-membered heteroaryl, or 3- to 6-membered heterocyclyl, wherein the $C_3$-$C_6$ cycloalkyl, phenyl, 5- or 6-membered heteroaryl, or 3- to 6-membered heterocyclyl is optionally substituted with one or two substituents independently selected from $C_1$-$C_6$ alkyl, $C_1$-$C_6$ alkoxy, $C_1$-$C_6$ hydroxyalkyl, $C_1$-$C_6$ haloalkyl, halo, oxo, =$NR^{11}$, CN, $NH_2$ and OH; and other variables are as defined herein.

In some embodiments, provided is a compound of Formula VIa:

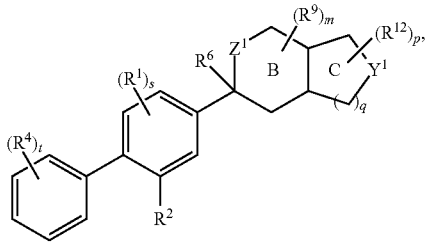

or a pharmaceutically acceptable salt, prodrug, deuterated analog, stereoisomer, or mixture of stereoisomers thereof, wherein
s is 0, 1, 2, or 3,
t is 0, 1, 2, 3, 4, or 5,
$Y^1$ is O, S, SO, $SO_2$, $CH_2$, $CHR^{12}$, $CR^{12}R^{12}$, NH or $NR^{12}$;
p is 0, 1, 2, 3, or 4; provided that the total number of $R^{12}$ is not more than 4;
q is 0, 1 or 2; and
other variables are as defined herein.

In some embodiments, provided is a compound of Formula VIIa:

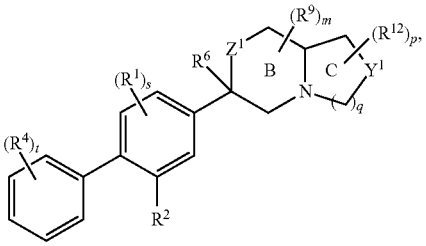

or a pharmaceutically acceptable salt, prodrug, deuterated analog, stereoisomer, or mixture of stereoisomers thereof, wherein
s is 0, 1, 2, or 3,
t is 0, 1, 2, 3, 4, or 5,
$Y^1$ is O, S, SO, $SO_2$, $CH_2$, $CHR^{12}$, $CR^{12}R^{12}$, NH or $NR^{12}$;
p is 0, 1, 2, 3, or 4; provided that the total number of $R^{12}$ is not more than 4;
q is 0, 1 or 2; and
other variables are as defined herein.

In some embodiments, provided is a compound of Formula VIIIa:

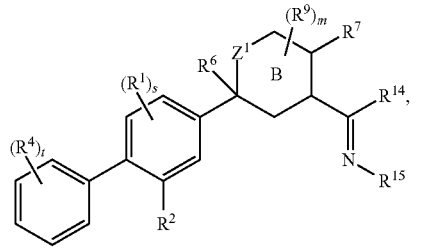

or a pharmaceutically acceptable salt, prodrug, deuterated analog, stereoisomer, or mixture of stereoisomers thereof, wherein
s is 0, 1, 2, or 3,
t is 0, 1, 2, 3, 4, or 5;
$R^7$ is H, halo, $C_1$-$C_6$ alkyl, $C_1$-$C_6$ alkoxy, $C_1$-$C_6$ haloalkyl, OH, CN, or $NH_2$;
$R^{14}$ is H, $C_1$-$C_6$ alkyl, $C_1$-$C_6$ heteroalkyl, $C_3$-$C_6$ cycloalkyl, heterocyclyl, aryl, or heteroaryl; each of which is optionally substituted with one or two substituents independently selected from $C_1$-$C_6$ alkyl, $C_1$-$C_6$ alkoxy, $C_1$-$C_6$ haloalkyl, halo, oxo, $=NR^{11}$, CN, $NH_2$ and OH;
$R^{15}$ is H or $C_1$-$C_6$ alkyl; or
$R^7$ and $R^{14}$ together with the atoms to which they are attached form $C_3$-$C_6$ cycloalkyl or 5- or 6-membered heterocyclyl optionally substituted with one or two $R^{12}$; or
$R^{14}$ is H, and $R^7$ and $R^{15}$ together with the atoms to which they are attached form 5- or 6-membered heterocyclyl optionally substituted with one to four $R^{12}$; or
$R^{14}$ and $R^{15}$ together with the atoms to which they are attached form 5- or 6-membered heteroaryl or 5- or 6-membered heterocyclyl optionally substituted with one to four $R^{16}$; or
$R^7$ and $R^{14}$ together with the atoms to which they are attached, and $R^{14}$ and $R^{15}$ together with the atoms to which they are attached form a fused bicyclic heterocyclyl optionally substituted with one or two $R^{16}$;
each $R^{16}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; and
other variables are as defined herein.

In some embodiments, provided is a compound of Formula IXa:

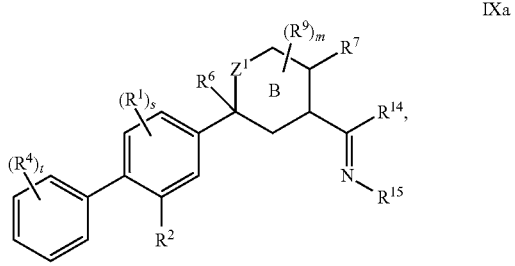

or a pharmaceutically acceptable salt, prodrug, deuterated analog, stereoisomer, or mixture of stereoisomers thereof, wherein
s is 0, 1, 2, or 3,
t is 0, 1, 2, 3, 4, or 5;
$R^7$ is H, halo, $C_1$-$C_6$ alkyl, $C_1$-$C_6$ alkoxy, $C_1$-$C_6$ haloalkyl, OH, CN, or $NH_2$;
$R^{14}$ is H, $C_1$-$C_5$ alkyl, $C_1$-$C_5$ heteroalkyl, $C_3$-$C_6$ cycloalkyl, heterocyclyl, aryl, or heteroaryl; each of which is optionally substituted with one or two substituents independently selected from $C_1$-$C_6$ alkyl, $C_1$-$C_6$ alkoxy, $C_1$-$C_6$ haloalkyl, halo, oxo, $=NR^{11}$, CN, $NH_2$ and OH;
$R^{15}$ is H or $C_1$-$C_6$ alkyl; or
$R^7$ and $R^{14}$ together with the atoms to which they are attached form 5- or 6-membered heterocyclyl optionally substituted with one or two $R^{12}$; or
$R^{14}$ is H, and $R^7$ and $R^{15}$ together with the atoms to which they are attached form 5- or 6-membered heterocyclyl optionally substituted with one to four $R^{12}$; or R$^{14}$ and R$^{15}$ together with the atoms to which they are attached form 5- or 6-membered heteroaryl or 5- or 6-membered heterocyclyl optionally substituted with one to four R$^{16}$; or R$^7$ and R$^{14}$ together with the atoms to which they are attached, and R$^{14}$ and R$^{15}$ together with the atoms to which they are attached form a fused bicyclic heterocyclyl optionally substituted with one or two R$^{16}$;

each R$^{16}$ is independently selected from the group consisting of C$_1$-C$_6$ alkyl, halo, OH, C$_1$-C$_6$ alkoxy, C$_1$-C$_6$ hydroxyalkyl, C$_1$-C$_6$ haloalkyl, NH$_2$ and CN; and other variables are as defined herein.

In some embodiments, provided is a compound of Formula X:

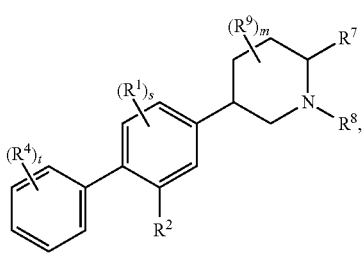

X or a pharmaceutically acceptable salt, prodrug, deuterated analog, stereoisomer, or mixture of stereoisomers thereof, wherein s is 0, 1, 2, or 3, t is 0, 1, 2, 3, 4, or 5;

R$^7$ is H, halo, C$_1$-C$_6$ alkyl, C$_1$-C$_6$ alkoxy, C$_1$-C$_6$ haloalkyl, OH, CN, or NH$_2$;

R$^8$ is C$_1$-C$_6$ alkyl, C$_1$-C$_6$ heteroalkyl, C$_3$-C$_6$ cycloalkyl, heterocyclyl, aryl, heteroaryl, C$_3$-C$_6$ cycloalkyl-C$_1$-C$_6$ alkyl, aryl-C$_1$-C$_6$ alkyl, heteroaryl-C$_1$-C$_6$ alkyl, or heterocyclyl-C$_1$-C$_6$ alkyl; each of which is optionally substituted with one to four substituents independently selected from C$_1$-C$_6$ alkyl, C$_1$-C$_6$ alkoxy, C$_1$-C$_6$ haloalkyl, halo, oxo, =NR$^{11}$, CN, NH$_2$ and OH; and other variables are as defined herein.

In some embodiments, provided is a compound of Formula XI:

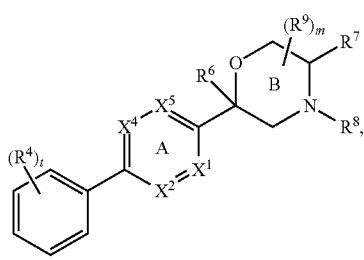

XI or a pharmaceutically acceptable salt, prodrug, deuterated analog, stereoisomer, or mixture of stereoisomers thereof, wherein t is 0, 1, 2, 3, 4, or 5;

other variables are as defined herein.

In some embodiments, s is 0 or 1. In some embodiments, t is 0 or 1.

In some embodiments, Z$^1$ is O.

In some embodiments, R$^7$ is H.

In some embodiments, R$^8$ is C$_1$-C$_6$ alkyl optionally substituted with one or two substituents independently selected from C$_1$-C$_6$ alkoxy, C$_1$-C$_6$ haloalkyl, halo, oxo, =NR$^{11}$, CN, NH$_2$ and OH.

In some embodiments, R$^8$ is C$_1$-C$_6$ heteroalkyl optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is C$_3$-C$_6$ cycloalkyl optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is 3- to 6-membered heterocyclyl optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is aryl optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, CN, NH$_2$ and OH.

In some embodiments, R$^8$ is 5- or 6-heteroaryl optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, CN, NH$_2$ and OH.

In some embodiments, R$^8$ is C$_3$-C$_6$ cycloalkyl-CH$_2$— optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is 3- to 6-membered heterocyclyl-CH$_2$— optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is aryl-CH$_2$— optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^8$ is 5- or 6-heteroaryl-CH$_2$— optionally substituted with one or two substituents independently selected from C$_1$-C$_6$ alkyl, C$_1$-C$_6$ alkoxy, C$_1$-C$_6$ hydroxyalkyl, C$_1$-C$_6$ haloalkyl, halo, oxo, =NR$^{11}$, CN, NH$_2$ and OH.

In some embodiments, R$^2$ is H.

In some embodiments, R$^2$ is phenyl optionally substituted with one to five R$^4$ or 5- or 6-membered heteroaryl optionally substituted with one to five R$^4$. In some embodiments, R$^2$ is phenyl optionally substituted with one R$^4$. In some embodiments, R$^2$ is 5- or 6-membered heteroaryl optionally substituted with one R$^4$.

In some embodiments, each R$^4$ independently is CH$_3$, CF$_3$, OH, F, or Cl.

In some embodiments, m is 0. In some embodiments, m is 1.

In some embodiments, a compound may be selected from those compounds in Table 1 or a pharmaceutically acceptable salt, prodrug, deuterated analog, stereoisomer, or mixture of stereoisomers thereof.

TABLE 1

| Compound # | Name | Structure |
|---|---|---|
| 1,001 | 1-(cyclopropylmethyl)-3-(4'-fluoro-[1,1'-biphenyl]-4-yl)piperidine | 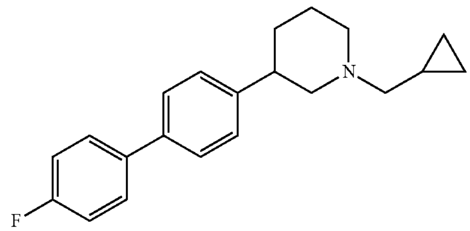 [SMILES: Fc1ccc(-c2ccc(C3CCCN(CC4CC4)C3)cc2)cc1] |
| 1,002 | 3-([1,1'-biphenyl]-4-yl)-1-((tetrahydrofuran-3-yl)methyl)piperidine | 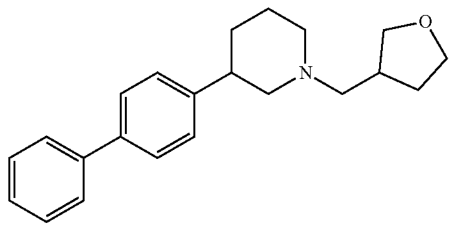 [SMILES: c1ccc(-c2ccc(C3CCCN(CC4CCOC4)C3)cc2)cc1] |
| 1,003 | 3-([1,1'-biphenyl]-4-yl)-1-cyclopentylpiperidine | 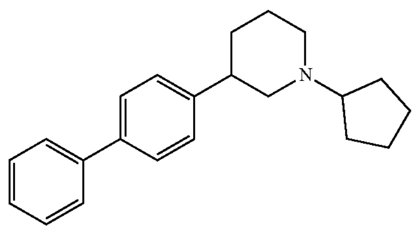 [SMILES: c1ccc(-c2ccc(C3CCCN(C4CCCC4)C3)cc2)cc1] |
| 1,004 | 3-([1,1'-biphenyl]-4-yl)-1-(pyrrolidin-3-ylmethyl)piperidine | 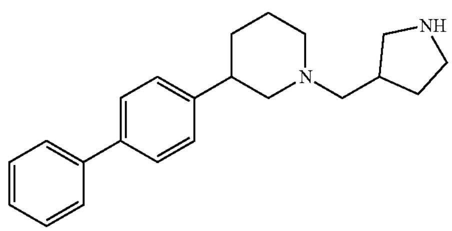 [SMILES: c1ccc(-c2ccc(C3CCCN(CC4CCNC4)C3)cc2)cc1] |
| 1,005 | 4-(4-(1-(cyclopentylmethyl)piperidin-3-yl)phenyl)pyridine | 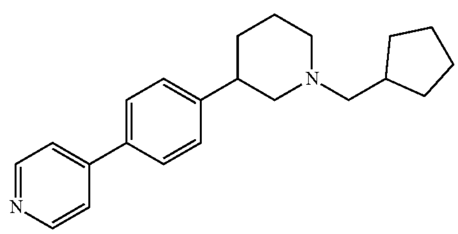 [SMILES: c1cc(-c2ccc(C3CCCN(CC4CCCC4)C3)cc2)ccn1] |
| 1,006 | 3-([1,1'-biphenyl]-4-yl)-1-(cyclopentylmethyl)piperidine | 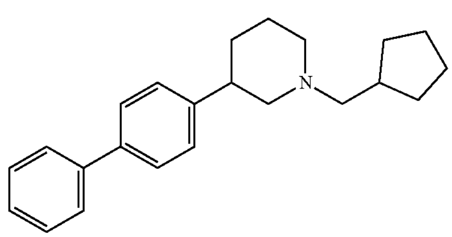 [SMILES: c1ccc(-c2ccc(C3CCCN(CC4CCCC4)C3)cc2)cc1] |

TABLE 1-continued

| Compound # | Name | Structure |
|---|---|---|
| 1,007 | 3-([1,1'-biphenyl]-4-yl)-1-(cyclopropylmethyl)piperidine | 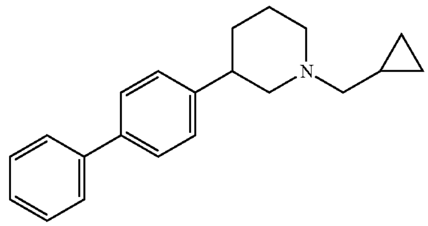 [SMILES: c1ccc(-c2ccc(C3CCCN(CC4CC4)C3)cc2)cc1] |
| 1,008 | 3-([1,1'-biphenyl]-4-yl)-1-benzylpiperidine | 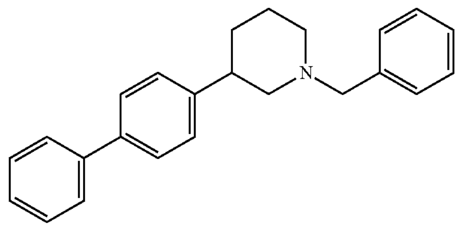 [SMILES: c1ccc(CN2CCCC(c3ccc(-c4ccccc4)cc3)C2)cc1] |
| 1,009 | 1-(cyclopentylmethyl)-3-(4'-fluoro-[1,1'-biphenyl]-4-yl)piperidine | 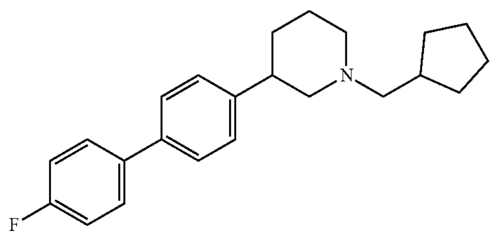 [SMILES: Fc1ccc(-c2ccc(C3CCCN(CC4CCCC4)C3)cc2)cc1] |
| 1,010 | 3-(4'-chloro-[1,1'-biphenyl]-4-yl)-1-(cyclopentylmethyl)piperidine | 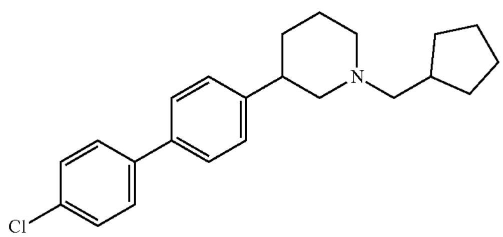 [SMILES: Clc1ccc(-c2ccc(C3CCCN(CC4CCCC4)C3)cc2)cc1] |
| 1,011 | 1-(cyclopentylmethyl)-3-(4'-(trifluoromethyl)-[1,1'-biphenyl]-4-yl)piperidine | 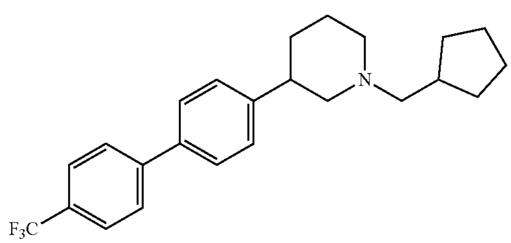 [SMILES: FC(F)(F)c1ccc(-c2ccc(C3CCCN(CC4CCCC4)C3)cc2)cc1] |
| 1,012 | 4'-(1-(cyclopentylmethyl)piperidin-3-yl)-[1,1'-biphenyl]-4-ol | 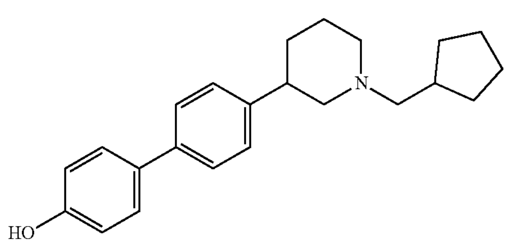 [SMILES: Oc1ccc(-c2ccc(C3CCCN(CC4CCCC4)C3)cc2)cc1] |

TABLE 1-continued

| Compound # | Name | Structure |
|---|---|---|
| 1,013 | 1-(cyclopentylmethyl)-3-(3'-(trifluoromethyl)-[1,1'-biphenyl]-4-yl)piperidine | 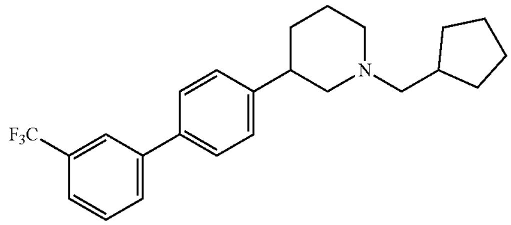 [SMILES: FC(F)(F)c1cccc(-c2ccc(C3CCCN(CC4CCCC4)C3)cc2)c1] |
| 1,014 | 1-(cyclopentylmethyl)-3-(2,2'-dimethyl-[1,1'-biphenyl]-4-yl)piperidine | 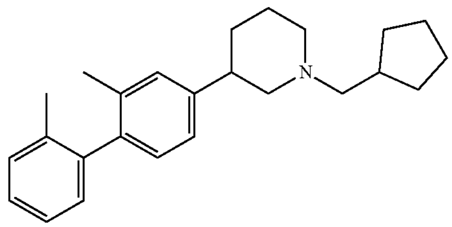 [SMILES: Cc1ccccc1-c1ccc(C2CCCN(CC3CCCC3)C2)cc1C] |
| 1,015 | 2-(5-(4-chlorothiophen-2-yl)-6-methylpyridin-2-yl)-4-(cyclopentylmethyl)morpholine | 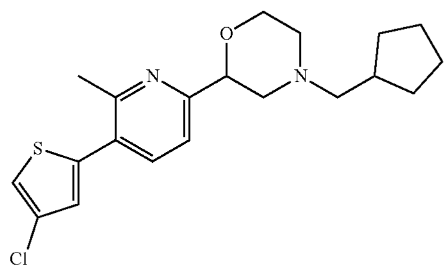 [SMILES: Cc1nc(C2CN(CC3CCCC3)CCO2)ccc1-c1cc(Cl)cs1] |
| 1,016 | 3-([1,1'-biphenyl]-4-yl)-1-(cyclopentylmethyl)piperidin-3-ol | 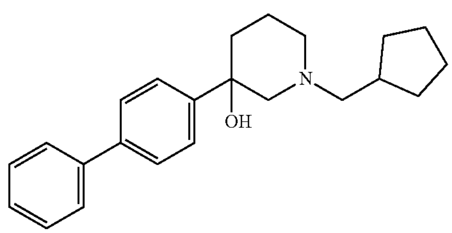 [SMILES: OC1(c2ccc(-c3ccccc3)cc2)CCCN(CC2CCCC2)C1] |
| 1,017 | 3-([1,1'-biphenyl]-4-yl)-1-(cyclopentylmethyl)piperidin-3-amine | 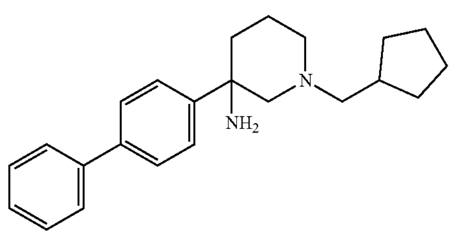 [SMILES: NC1(c2ccc(-c3ccccc3)cc2)CCCN(CC2CCCC2)C1] |
| 1,018 | 3-([1,1'-biphenyl]-4-yl)-1-(cyclopentylmethyl)-3-fluoropiperidine | 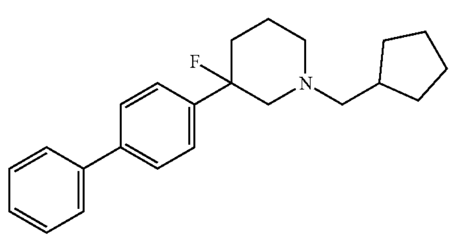 [SMILES: FC1(c2ccc(-c3ccccc3)cc2)CCCN(CC2CCCC2)C1] |

TABLE 1-continued

| Compound # | Name | Structure |
|---|---|---|
| 1,019 | 3-([1,1':2',1''-terphenyl]-4'-yl)-1-(cyclopentylmethyl)piperidin-3-amine | 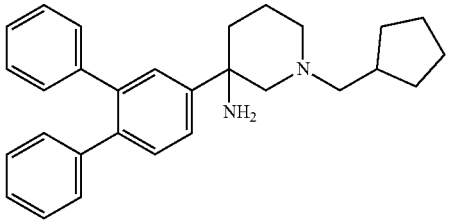 [SMILES: NC1(c2ccc(-c3ccccc3)c(-c3ccccc3)c2)CCCN(CC2CCCC2)C1] |
| 1,020 | 1-(cyclopentylmethyl)-3-(6-(trifluoromethyl)-[1,1'-biphenyl]-3-yl)piperidine | 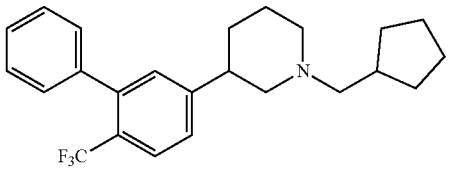 [SMILES: FC(F)(F)c1ccc(C2CCCN(CC3CCCC3)C2)cc1-c1ccccc1] |
| 1,021 | 3-([1,1'-biphenyl]-4-yl)-1-isopropylpiperidine | 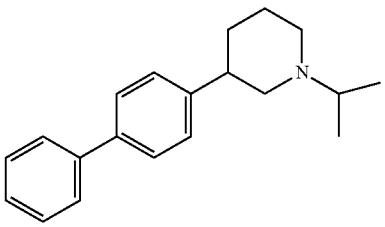 [SMILES: CC(C)N1CCCC(c2ccc(-c3ccccc3)cc2)C1] |
| 1,022 | 3-([1,1'-biphenyl]-4-yl)-1-cyclopentylpiperidin-3-ol | 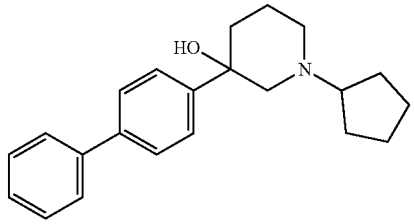 [SMILES: OC1(c2ccc(-c3ccccc3)cc2)CCCN(C2CCCC2)C1] |
| 1,023 | 3-([1,1'-biphenyl]-4-yl)octahydropyrido[2,1-c[1,2,4]oxazine | 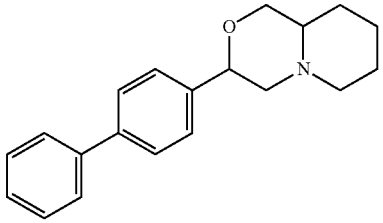 [SMILES: c1ccc(-c2ccc(C3CN4CCCCC4CO3)cc2)cc1] |
| 1,024 | 3-([1,1'-biphenyl]-4-yl)hexahydro-1H-[1,4]oxazino[3,4-c][1,4]oxazine | 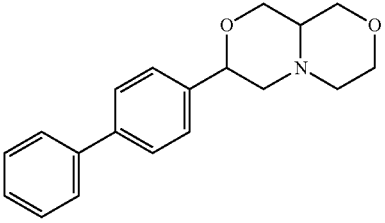 [SMILES: c1ccc(-c2ccc(C3CN4CCOCC4CO3)cc2)cc1] |
| 1,025 | 3-([1,1'-biphenyl]-4-yl)hexahydro-1H-pyrrolo[2,1-c][1,4]oxazine | 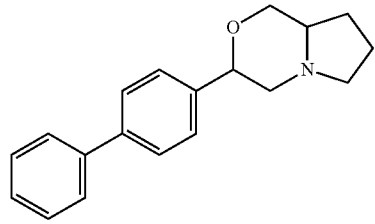 [SMILES: c1ccc(-c2ccc(C3CN4CCCC4CO3)cc2)cc1] |

TABLE 1-continued

| Compound # | Name | Structure |
|---|---|---|
| 1,026 | 1-(cyclopentylmethyl)-3-(4'-fluoro-[1,1'-biphenyl]-4-yl)piperidin-3-ol | 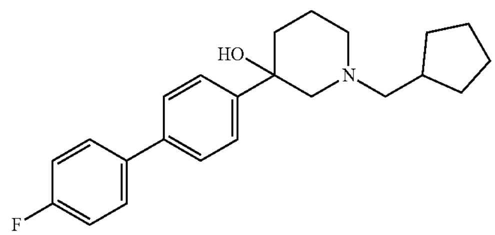 [SMILES: OC1(c2ccc(-c3ccc(F)cc3)cc2)CCCN(CC2CCCC2)C1] |
| 1,027 | 1-((tetrahydrofuran-3-yl)methyl)-3-(2-(trifluoromethyl)-[1,1'-biphenyl]-4-yl)piperidine | 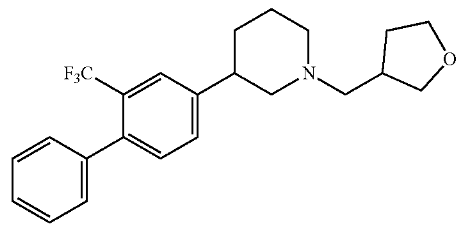 [SMILES: FC(F)(F)c1cc(C2CCCN(CC3CCOC3)C2)ccc1-c1ccccc1] |
| 1,028 | 3-(4-(tetrahydrofuran-2-yl)-3-(trifluoromethyl)phenyl)-1-((tetrahydrofuran-3-yl)methyl)piperidine | 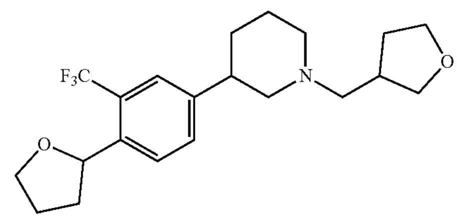 [SMILES: FC(F)(F)c1cc(C2CCCN(CC3CCOC3)C2)ccc1C1CCCO1] |
| 1,029 | 1-(cyclopentylmethyl)-3-(3',5'-difluoro[1,1'-biphenyl]-4-yl)piperidine | 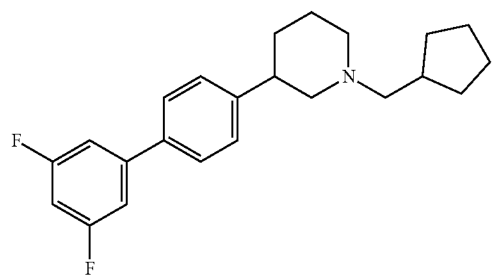 [SMILES: Fc1cc(F)cc(-c2ccc(C3CCCN(CC4CCCC4)C3)cc2)c1] |
| 1,030 | 2-(5-(1-((tetrahydrofuran-3-yl)methyl)piperidin-3-yl)-[1,1'-biphenyl]-2-yl)pyridine | 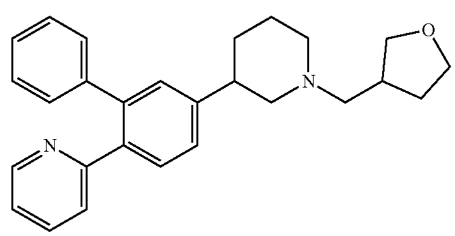 [SMILES: c1ccc(-c2cc(C3CCCN(CC4CCOC4)C3)ccc2-c2ccccn2)cc1] |
| 1,031 | 2-(3-([1,1'-biphenyl]-4-yl)piperidin-1-yl)thiazole | 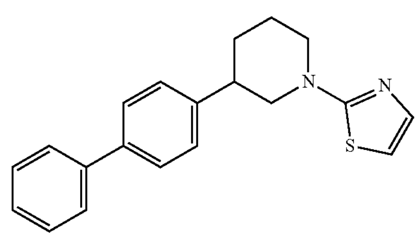 [SMILES: c1ccc(-c2ccc(C3CCCN(c4nccs4)C3)cc2)cc1] |

TABLE 1-continued

| Compound # | Name | Structure |
|---|---|---|
| 1,032 | 3-([1,1'-biphenyl]-4-yl)-1-(3,4-dihydro-2H-pyrrol-5-yl)piperidine | 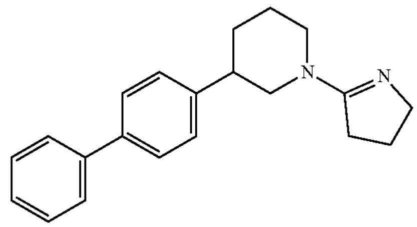 [SMILES: c1ccc(-c2ccc(C3CCCN(C4=NCCC4)C3)cc2)cc1] |
| 1,033 | 2-(3-([1,1-biphenyl]-4-yl)piperidin-1-yl)pyridine | 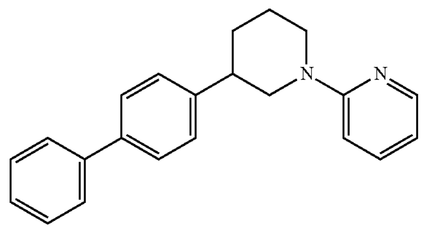 [SMILES: c1ccc(-c2ccc(C3CCCN(c4ccccn4)C3)cc2)cc1] |
| 1,034 | 1-(pyridin-2-yl)-3-(2-(trifluoromethyl)-[1,1'-biphenyl]-4-yl)piperidin-3-amine | 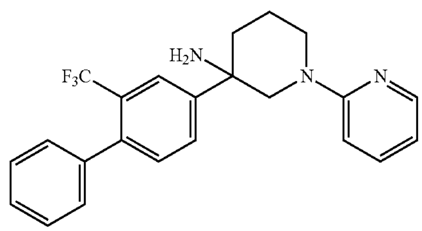 [SMILES: NC1(c2ccc(-c3ccccc3)c(C(F)(F)F)c2)CCCN(c2ccccn2)C1] |
| 1,035 | 1-benzyl-3-(4'-fluoro-[1,1'-biphenyl]-4-yl)piperidine | 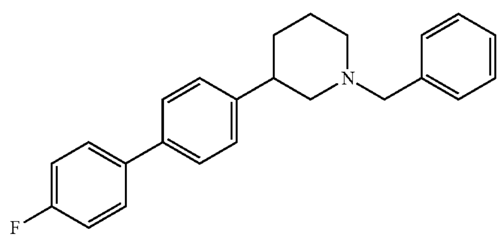 [SMILES: Fc1ccc(-c2ccc(C3CCCN(Cc4ccccc4)C3)cc2)cc1] |
| 1,036 | 1-(cyclopentylmethyl)-3-(2-(trifluoromethyl)-[1,1'-biphenyl]-4-yl)piperidine | 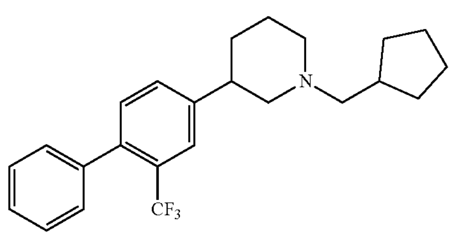 [SMILES: FC(F)(F)c1cc(C2CCCN(CC3CCCC3)C2)ccc1-c1ccccc1] |
| 1037 | 1-((tetrahydrofuran-3-yl)methyl)-3-(2-(trifluoromethyl)-[1,1'-biphenyl]-4-yl)piperidine | 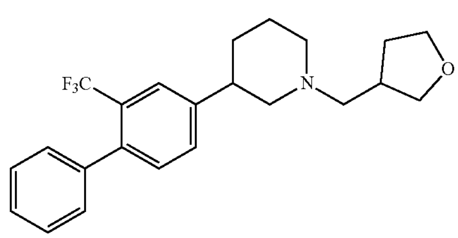 [SMILES: FC(F)(F)c1cc(C2CCCN(CC3CCOC3)C2)ccc1-c1ccccc1] |

TABLE 1-continued

| Compound # | Name | Structure |
|---|---|---|
| 1038 | 3-(4'-chloro-2-methyl-[1,1'-biphenyl]-4-yl)-1-(cyclopentylmethyl)piperidine | 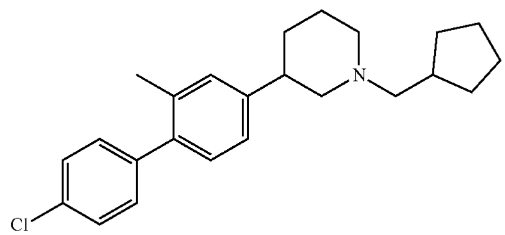 [SMILES: Cc1cc(C2CCCN(CC3CCCC3)C2)ccc1-c1ccc(Cl)cc1] |
| 1039 | 3-(4'-chloro-3-methyl-[1,1'-biphenyl]-4-yl)-1-(cyclopentylmethyl)piperidine | 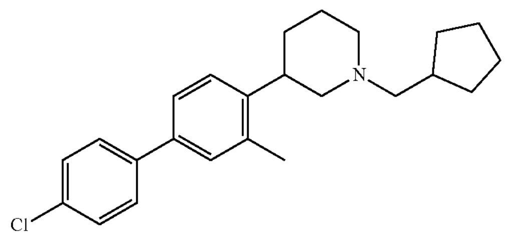 [SMILES: Cc1cc(-c2ccc(Cl)cc2)ccc1C1CCCN(CC2CCCC2)C1] |
| 1040 | 3-(4'-chloro-2-methyl-[1,1'-biphenyl]-4-yl)-1-cyclopentylpiperidine | 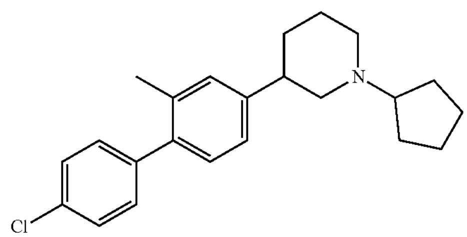 [SMILES: Cc1cc(C2CCCN(C3CCCC3)C2)ccc1-c1ccc(Cl)cc1] |
| 1041 | 1-cyclopentyl-3-(4'-fluoro-3-methyl-[1,1'-biphenyl]-4-yl)piperidine | 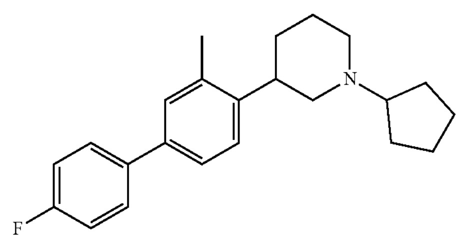 |
| 1042 | 3-(4'-chloro-3-methyl-[1,1'-biphenyl]-4-yl)-1-cyclopentylpiperidine | 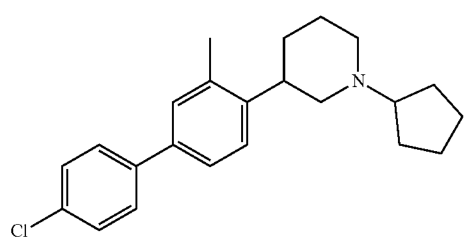 [SMILES: Cc1cc(-c2ccc(Cl)cc2)ccc1C1CCCN(C2CCCC2)C1] |
| 1043 | 2-(1-cyclopentylpiperidin-3-yl)-5-(4-fluorophenyl)-3-methylpyridine | 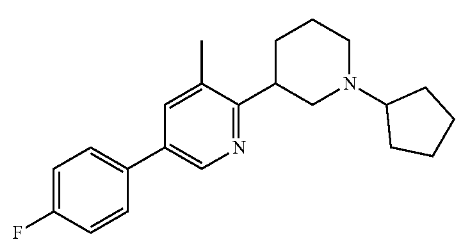 |

TABLE 1-continued

| Compound # | Name | Structure |
|---|---|---|
| 1044 | 1-(cyclopropylmethyl)-3-(4'-fluoro-[1,1'-biphenyl]-4-yl)piperidine | 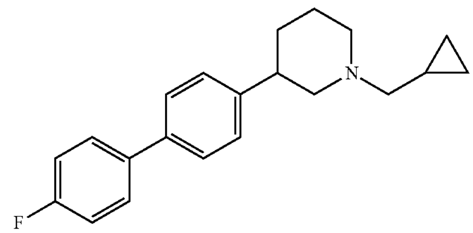 [SMILES: Fc1ccc(-c2ccc(C3CCCN(CC4CC4)C3)cc2)cc1] |
| 1045 | 1-benzyl-3-(4'-fluoro-[1,1'-biphenyl]-4-yl)piperidine | 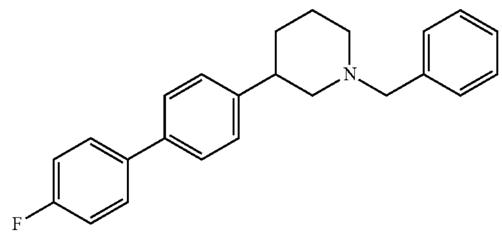 [SMILES: Fc1ccc(-c2ccc(C3CCCN(Cc4ccccc4)C3)cc2)cc1] |
| 1046 | 5-(4-chlorophenyl)-2-(1-cyclopentylpiperidin-3-yl)-3-methylpyridine | 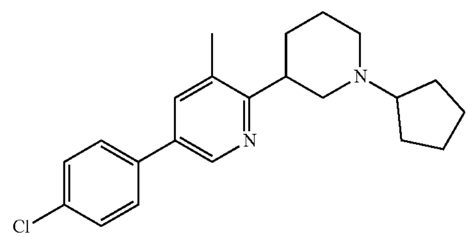 [SMILES: Cc1cc(-c2ccc(Cl)cc2)cnc1C1CCCN(C2CCCC2)C1] |
| 1047 | 5-(1-cyclopentylpiperidin-3-yl)-2-(4-fluorophenyl)-4-methylpyridine | 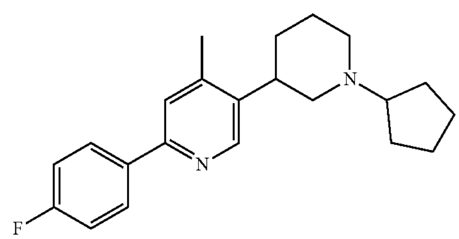 |
| 1048 | 2-(4-chlorophenyl)-5-(1-cyclopentylpiperidin-3-yl)-4-methylpyridine | 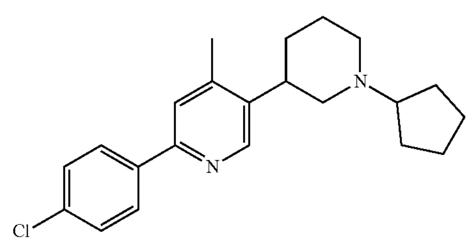 [SMILES: Cc1cc(-c2ccc(Cl)cc2)ncc1C1CCCN(C2CCCC2)C1] |
| 1049 | 3-(1-cyclopentylpiperidin-3-yl)-6-(4-fluorophenyl)-2-methylpyridine | 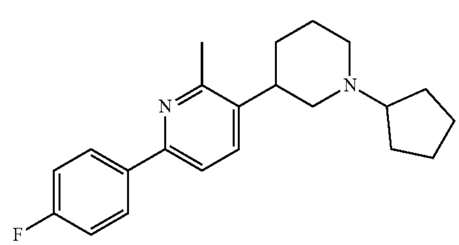 |

TABLE 1-continued

| Compound # | Name | Structure |
|---|---|---|
| 1050 | 6-(4-chlorophenyl)-3-(1-cyclopentylpiperidin-3-yl)-2-methylpyridine | 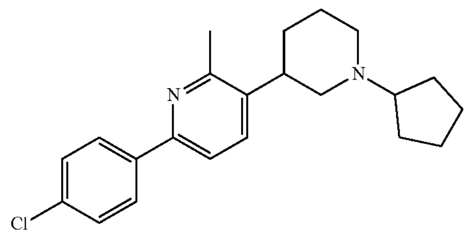 [SMILES: Cc1nc(-c2ccc(Cl)cc2)ccc1C1CCCN(C2CCCC2)C1] |
| 1051 | 2-(4-chlorophenyl)-5-(1-cyclopentylpiperidin-3-yl)-4-methylpyrimidine | 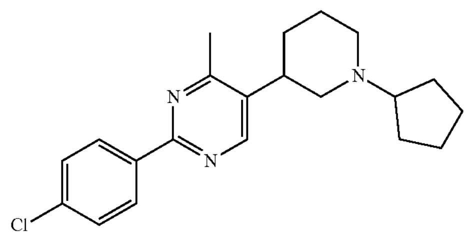 [SMILES: Cc1nc(-c2ccc(Cl)cc2)ncc1C1CCCN(C2CCCC2)C1] |
| 1052 | 5-(4-chlorophenyl)-2-(1-cyclopentylpiperidin-3-yl)-3-methylpyrazine | 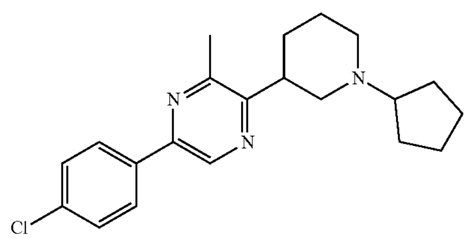 [SMILES: Cc1nc(-c2ccc(Cl)cc2)cnc1C1CCCN(C2CCCC2)C1] |
| 1053 | 3-(4-chlorophenyl)-6-(1-cyclopentylpiperidin-3-yl)-5-methyl-1,2,4-triazine | 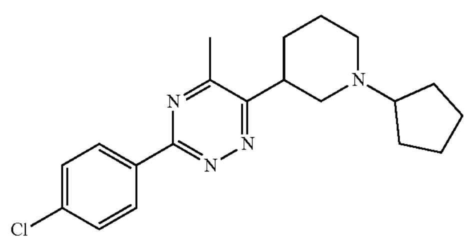 [SMILES: Cc1nc(-c2ccc(Cl)cc2)nnc1C1CCCN(C2CCCC2)C1] |
| 1054 | 5-chloro-6'-(1-cyclopentylpiperidin-3-yl)-5'-methyl-2,3'-bipyridine | 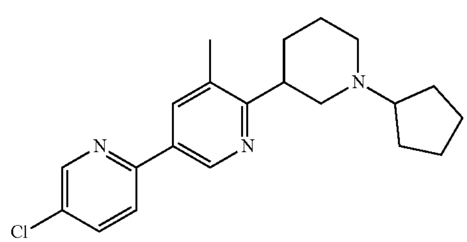 [SMILES: Cc1cc(-c2ccc(Cl)cn2)cnc1C1CCCN(C2CCCC2)C1] |
| 1055 | 5-(1-cyclopentylpiperidin-3-yl)-2-(4-fluorophenyl)isonicotinonitrile | 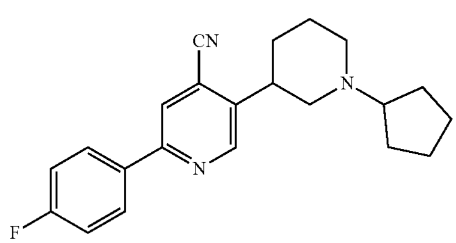 [SMILES: N#Cc1cc(-c2ccc(F)cc2)ncc1C1CCCN(C2CCCC2)C1] |

TABLE 1-continued

| Compound # | Name | Structure |
|---|---|---|
| 1056 | 3-(4'-fluoro-3-methyl-[1,1'-biphenyl]-4-yl)-1-(tetrahydro-2H-pyran-4-yl)piperidine | 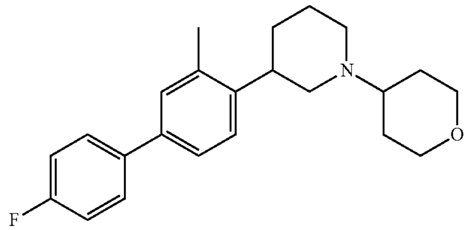 [SMILES: Cc1cc(-c2ccc(F)cc2)ccc1C1CCCN(C2CCOCC2)C1] |
| 1057 | 3-(4'-chloro-3-methyl-[1,1'-biphenyl]-4-yl)-1-(tetrahydro-2H-pyran-4-yl)piperidine | 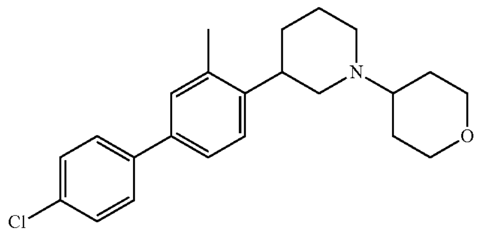 [SMILES: Cc1cc(-c2ccc(Cl)cc2)ccc1C1CCCN(C2CCOCC2)C1] |
| 1058 | 4-cyclopentyl-2-(4'-fluoro-3-methyl-[1,1'-biphenyl]-4-yl)morpholine | 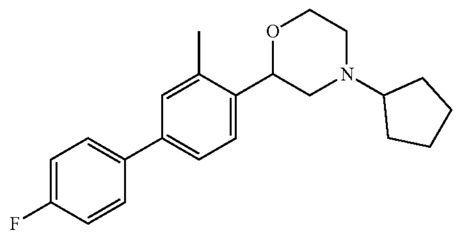 |
| 1059 | 2-(4'-chloro-3-methyl-[1,1'-biphenyl]-4-yl)-4-cyclopentylmorpholine | 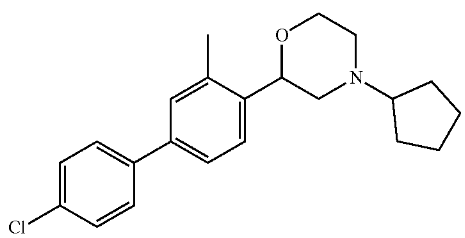 [SMILES: Cc1cc(-c2ccc(Cl)cc2)ccc1C1CN(C2CCCC2)CCO1] |

In one embodiment, a compound may be selected from those compounds in Table 2 or a pharmaceutically acceptable salt, prodrug, deuterated analog, stereoisomer, or mixture of stereoisomers thereof.

TABLE 2

| Compound # | Name | Structure |
|---|---|---|
| 2,001 | 2-(3-([1,1'-biphenyl]-4-yl)cyclohexyl)-4,5-dihydro-1H-imidazole | 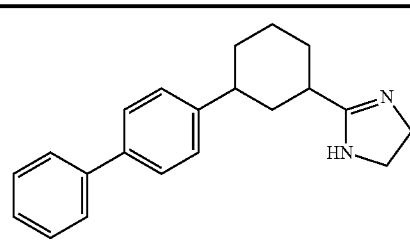 |

TABLE 2-continued

| Compound # | Name | Structure |
|---|---|---|
| 2,002 | 2-(2-([1,1'-biphenyl]-4-yl)tetrahydro-2H-pyran-4-yl)-4,5-dihydro-1H-imidazole | 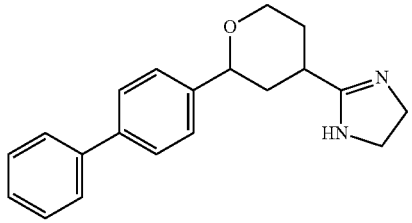 [SMILES: c1ccc(-c2ccc(C3CC(C4=NCCN4)CCO3)cc2)cc1] |
| 2,003 | 2-(2-(4'-fluoro-[1,1'-biphenyl]-4-yl)tetrahydro-2H-pyran-4-yl)-4,5-dihydro-1H-imidazole | 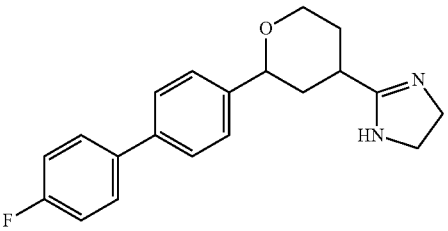 [SMILES: Fc1ccc(-c2ccc(C3CC(C4=NCCN4)CCO3)cc2)cc1] |
| 2,004 | 1-([1,1'-biphenyl]-4-yl)-3-(4,5-dihydro-1H-imidazol-2-yl)cyclohexan-1-ol | 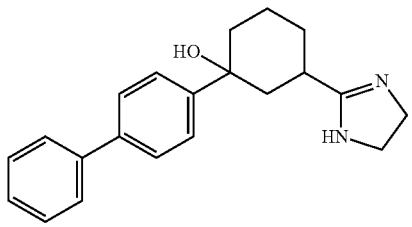 [SMILES: OC1(c2ccc(-c3ccccc3)cc2)CCCC(C2=NCCN2)C1] |
| 2,005 | 4-([1,1'-biphenyl]-4-yl)-2-(4,5-dihydro-1H-imidazol-2-yl)tetrahydro-2H-pyran-4-ol | 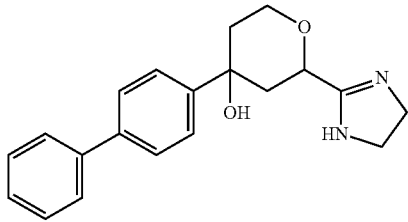 [SMILES: OC1(c2ccc(-c3ccccc3)cc2)CCOC(C2=NCCN2)C1] |
| 2,006 | 3-(4,5-dihydro-1H-imidazol-2-yl)-1-(6-(trifluoromethyl)-[1,1'-biphenyl]-3-yl)cyclohexan-1-ol | 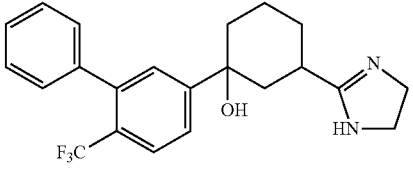 [SMILES: OC1(c2ccc(C(F)(F)F)c(-c3ccccc3)c2)CCCC(C2=NCCN2)C1] |
| 2,007 | 1-(4,5-dihydro-1H-imidazol-2-yl)-3-(6-(trifluoromethyl)-[1,1'-biphenyl]-3-yl)cyclohexan-1-ol | 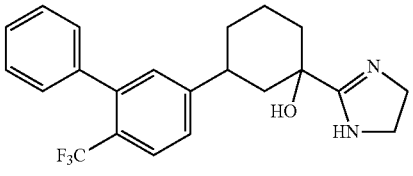 [SMILES: OC1(C2=NCCN2)CCCC(c2ccc(C(F)(F)F)c(-c3ccccc3)c2)C1] |
| 2,008 | 1-([1,1':2',1''-terphenyl]-4'-yl)-3-(4,5-dihydro-1H-imidazol-2-yl)cyclohexan-1-ol | 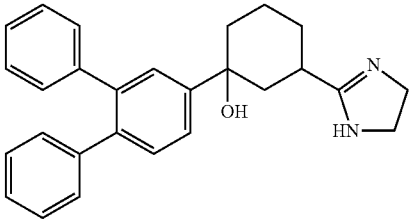 [SMILES: OC1(c2ccc(-c3ccccc3)c(-c3ccccc3)c2)CCCC(C2=NCCN2)C1] |

TABLE 2-continued

| Compound # | Name | Structure |
|---|---|---|
| 2,009 | 1-([1,1'-biphenyl]-4-yl)-3-(pyrrolidin-2-yl)cyclohexan-1-ol | 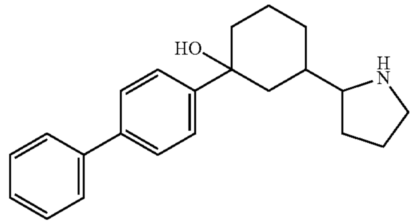 [SMILES: OC1(c2ccc(-c3ccccc3)cc2)CCCC(C2CCCN2)C1] |

In one embodiment, a compound may be selected from those compounds in Table 3 or a pharmaceutically acceptable salt, prodrug, deuterated analog, stereoisomer, or mixture of stereoisomers thereof.

TABLE 3

| Compound # | Name | Structure |
|---|---|---|
| 3,001 | 3-([1,1'-biphenyl]-4-yl)-1-(4,5-dihydro-1H-imidazol-2-yl)piperidine | 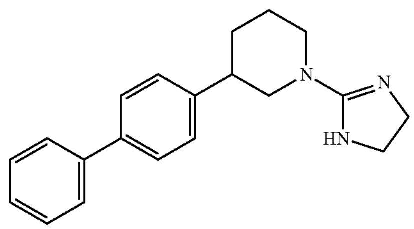 [SMILES: c1ccc(-c2ccc(C3CCCN(C4=NCCN4)C3)cc2)cc1] |
| 3,002 | 2-([1,1'-biphenyl]-4-yl)-4-(4,5-dihydro-1H-imidazol-2-yl)morpholine | 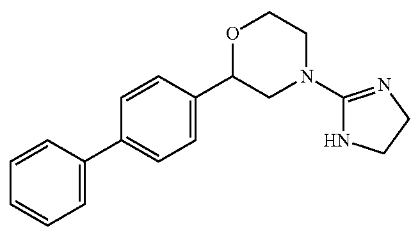 [SMILES: c1ccc(-c2ccc(C3CN(C4=NCCN4)CCO3)cc2)cc1] |
| 3,003 | 4-(4,5-dihydro-1H-imidazol-2-yl)-2-(4'-fluoro-[1,1'-biphenyl]-4-yl)morpholine | 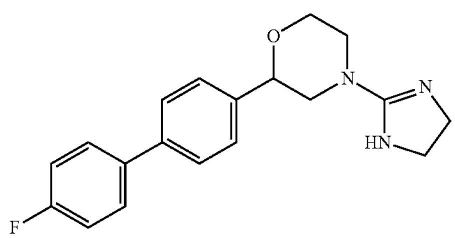 [SMILES: Fc1ccc(-c2ccc(C3CN(C4=NCCN4)CCO3)cc2)cc1] |
| 3,004 | 3-([1,1'-biphenyl]-4-yl)-1-(4,5-dihydro-1H-imidazol-2-yl)piperidin-3-ol | 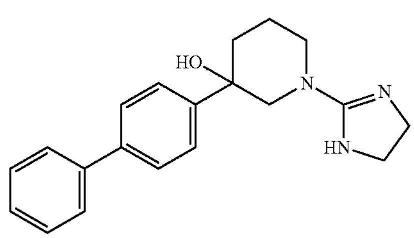 [SMILES: OC1(c2ccc(-c3ccccc3)cc2)CCCN(C2=NCCN2)C1] |

TABLE 3-continued

| Compound # | Name | Structure |
|---|---|---|
| 3,005 | 6-([1,1'-biphenyl]-4-yl)hexahydro-3H-imidazo[5,1-c][1,4]oxazin-3-imine | 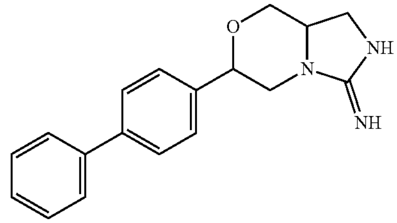 [SMILES: N=C1NCC2COC(c3ccc(-c4ccccc4)cc3)CN12] |
| 3,006 | 6-([1,1'-biphenyl]-4-yl)-3-iminooctahydroimidazo[1,5-a]pyridin-6-ol | 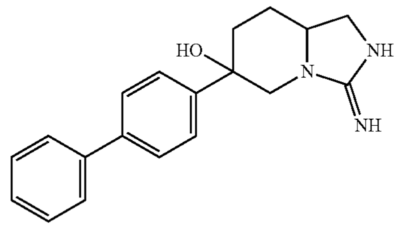 [SMILES: N=C1NCC2CCC(O)(c3ccc(-c4ccccc4)cc3)CN12] |
| 3,007 | 8-([1,1'-biphenyl]-4-yl)-2,3,5,5a,6,7,8,9-octahydroimidazo[2',1':2,3]imidazo[1,5-a]pyridin-8-ol | 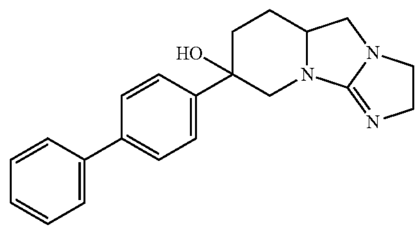 [SMILES: OC1(c2ccc(-c3ccccc3)cc2)CCC2CN3CCN=C3N2C1] |

In one embodiment, a compound may be selected from those compounds in Table 4 or a pharmaceutically acceptable salt, prodrug, deuterated analog, stereoisomer, or mixture of stereoisomers thereof.

TABLE 4

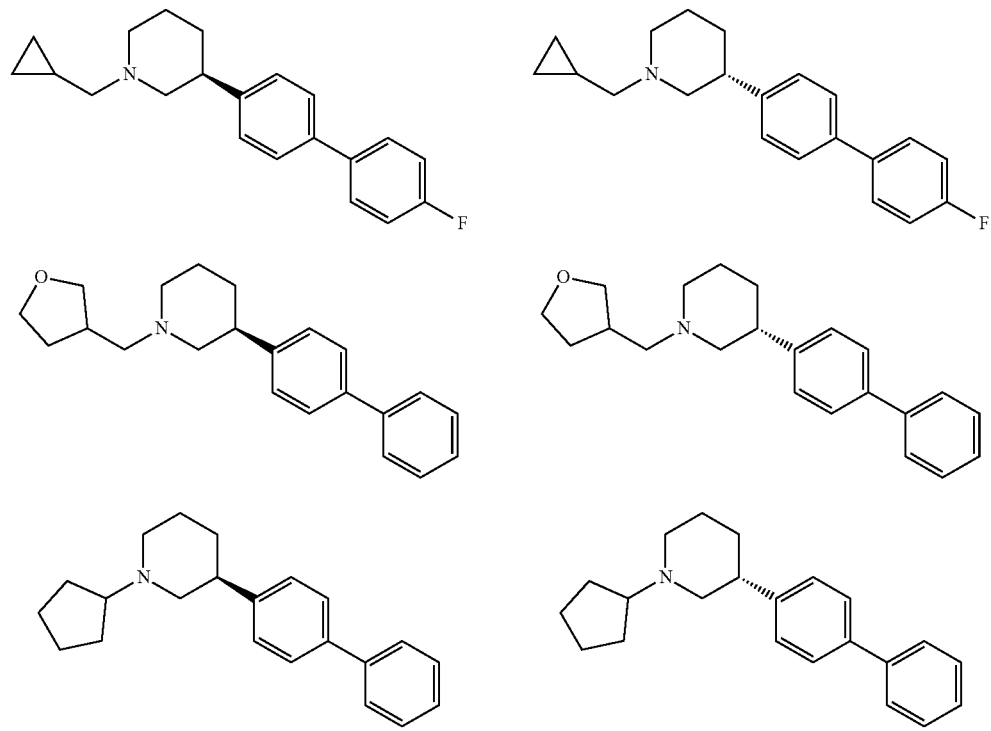

TABLE 4-continued
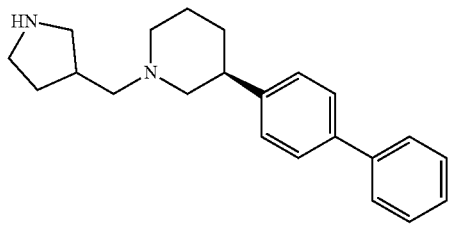 [SMILES: c1ccc(-c2ccc([C@@H]3CCCN(CC4CCNC4)C3)cc2)cc1]
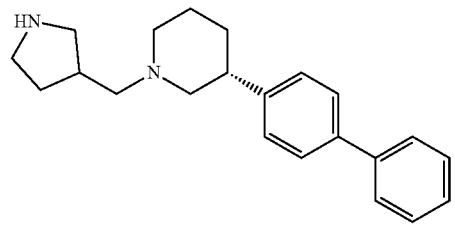 [SMILES: c1ccc(-c2ccc([C@H]3CCCN(CC4CCNC4)C3)cc2)cc1]
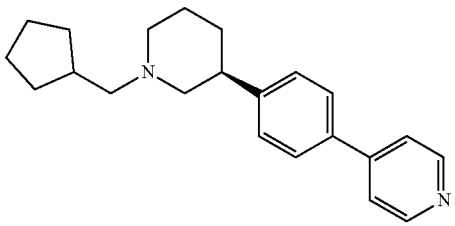 [SMILES: c1cc(-c2ccc([C@@H]3CCCN(CC4CCCC4)C3)cc2)ccn1]
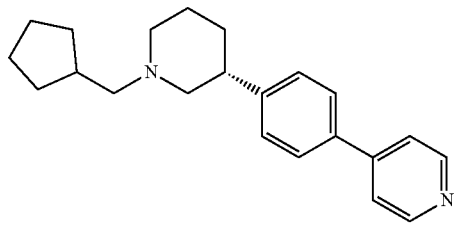 [SMILES: c1cc(-c2ccc([C@H]3CCCN(CC4CCCC4)C3)cc2)ccn1]
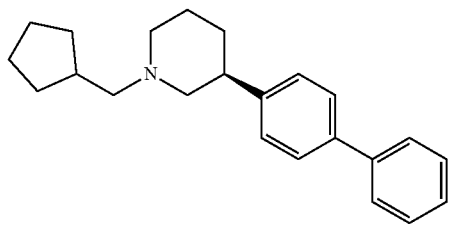 [SMILES: c1ccc(-c2ccc([C@@H]3CCCN(CC4CCCC4)C3)cc2)cc1]
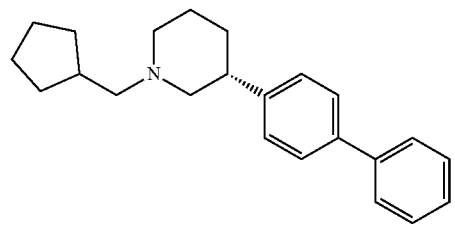 [SMILES: c1ccc(-c2ccc([C@H]3CCCN(CC4CCCC4)C3)cc2)cc1]
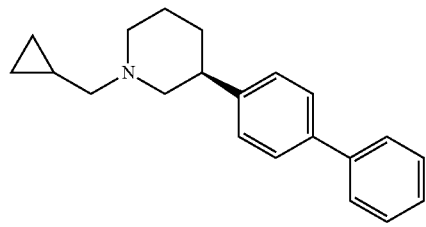 [SMILES: c1ccc(-c2ccc([C@@H]3CCCN(CC4CC4)C3)cc2)cc1]
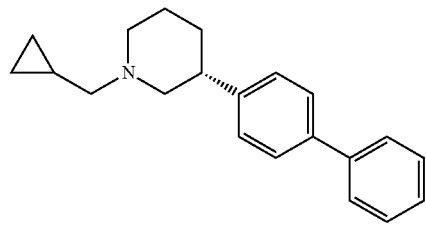 [SMILES: c1ccc(-c2ccc([C@H]3CCCN(CC4CC4)C3)cc2)cc1]
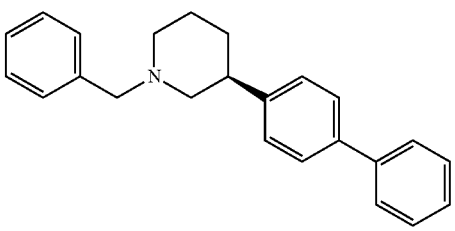 [SMILES: c1ccc(CN2CCC[C@@H](c3ccc(-c4ccccc4)cc3)C2)cc1]
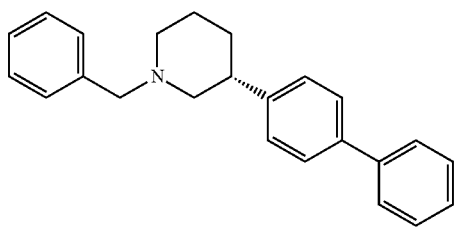 [SMILES: c1ccc(CN2CCC[C@H](c3ccc(-c4ccccc4)cc3)C2)cc1]
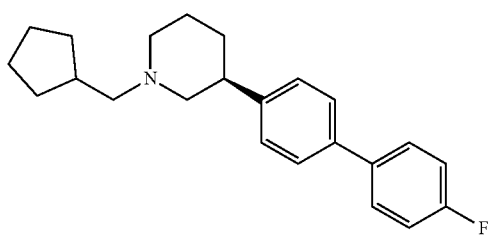 [SMILES: Fc1ccc(-c2ccc([C@@H]3CCCN(CC4CCCC4)C3)cc2)cc1]
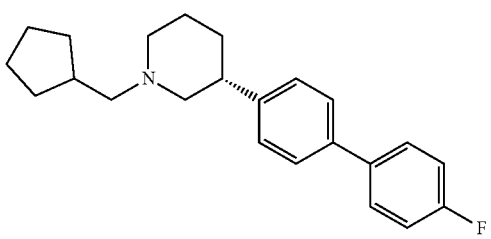 [SMILES: Fc1ccc(-c2ccc([C@H]3CCCN(CC4CCCC4)C3)cc2)cc1]

TABLE 4-continued
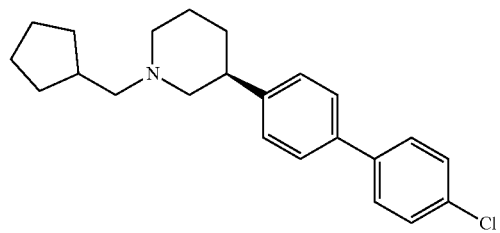 [SMILES: Clc1ccc(-c2ccc([C@@H]3CCCN(CC4CCCC4)C3)cc2)cc1]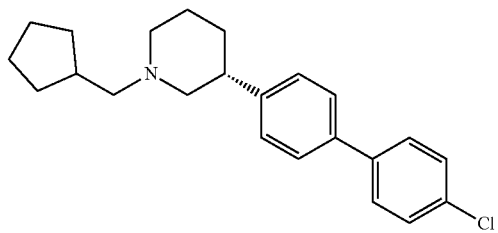 [SMILES: Clc1ccc(-c2ccc([C@H]3CCCN(CC4CCCC4)C3)cc2)cc1]
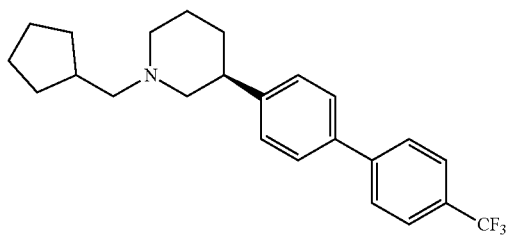 [SMILES: FC(F)(F)c1ccc(-c2ccc([C@@H]3CCCN(CC4CCCC4)C3)cc2)cc1]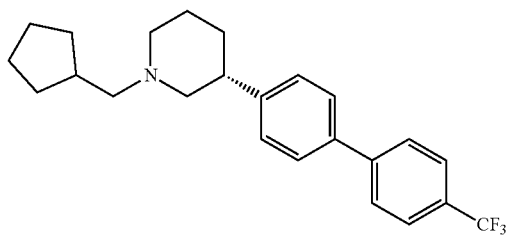 [SMILES: FC(F)(F)c1ccc(-c2ccc([C@H]3CCCN(CC4CCCC4)C3)cc2)cc1]
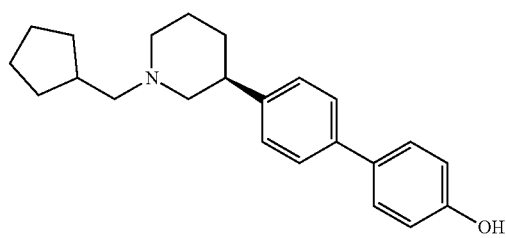 [SMILES: Oc1ccc(-c2ccc([C@@H]3CCCN(CC4CCCC4)C3)cc2)cc1]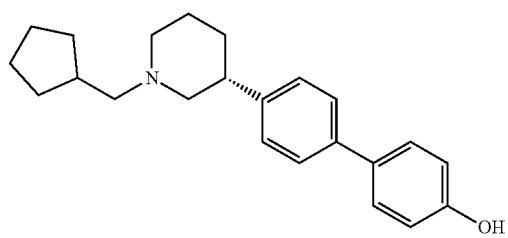 [SMILES: Oc1ccc(-c2ccc([C@H]3CCCN(CC4CCCC4)C3)cc2)cc1]
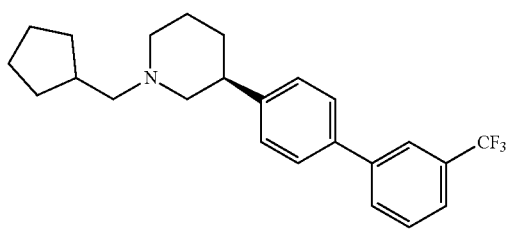 [SMILES: FC(F)(F)c1cccc(-c2ccc([C@@H]3CCCN(CC4CCCC4)C3)cc2)c1]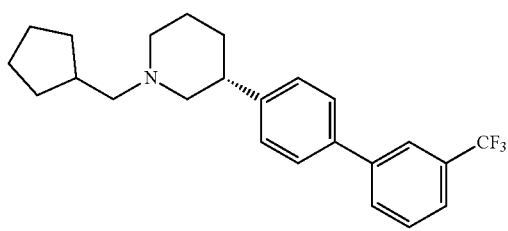 [SMILES: FC(F)(F)c1cccc(-c2ccc([C@H]3CCCN(CC4CCCC4)C3)cc2)c1]
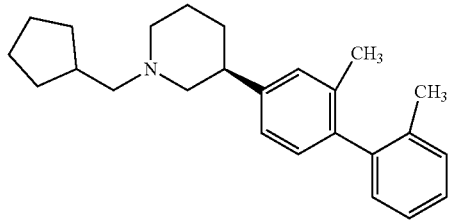 [SMILES: Cc1ccccc1-c1ccc([C@@H]2CCCN(CC3CCCC3)C2)cc1C]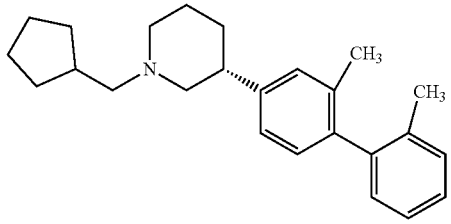 [SMILES: Cc1ccccc1-c1ccc([C@H]2CCCN(CC3CCCC3)C2)cc1C]
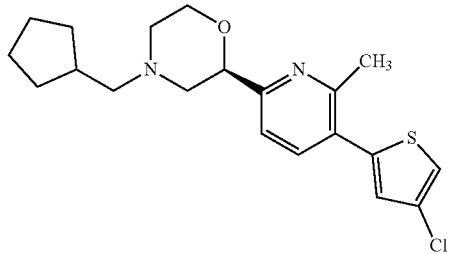 [SMILES: Cc1nc([C@H]2CN(CC3CCCC3)CCO2)ccc1-c1cc(Cl)cs1]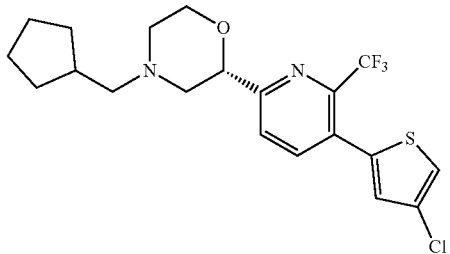 [SMILES: FC(F)(F)c1nc([C@@H]2CN(CC3CCCC3)CCO2)ccc1-c1cc(Cl)cs1]

TABLE 4-continued
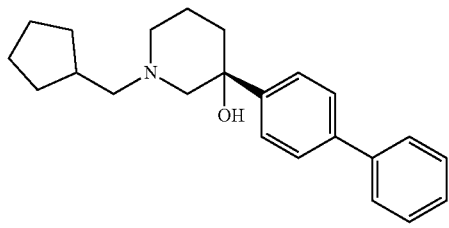 [SMILES: O[C@@]1(c2ccc(-c3ccccc3)cc2)CCCN(CC2CCCC2)C1]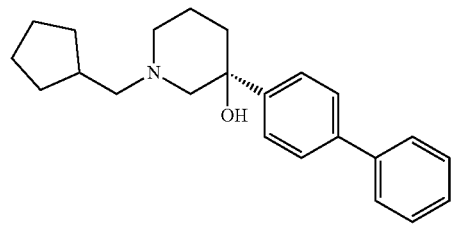 [SMILES: O[C@]1(c2ccc(-c3ccccc3)cc2)CCCN(CC2CCCC2)C1]
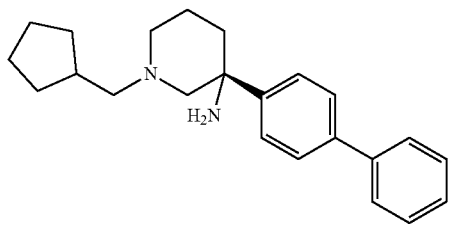 [SMILES: N[C@@]1(c2ccc(-c3ccccc3)cc2)CCCN(CC2CCCC2)C1]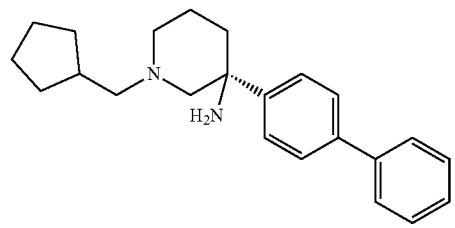 [SMILES: N[C@]1(c2ccc(-c3ccccc3)cc2)CCCN(CC2CCCC2)C1]
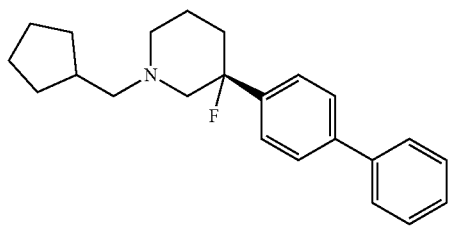 [SMILES: F[C@@]1(c2ccc(-c3ccccc3)cc2)CCCN(CC2CCCC2)C1]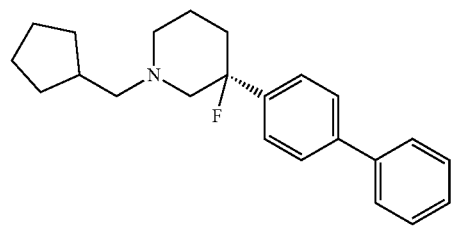 [SMILES: F[C@]1(c2ccc(-c3ccccc3)cc2)CCCN(CC2CCCC2)C1]
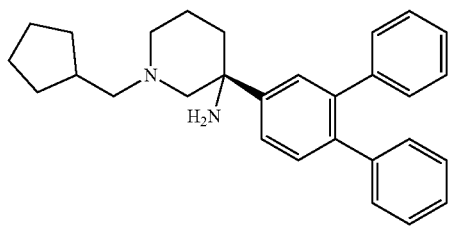 [SMILES: N[C@@]1(c2ccc(-c3ccccc3)c(-c3ccccc3)c2)CCCN(CC2CCCC2)C1]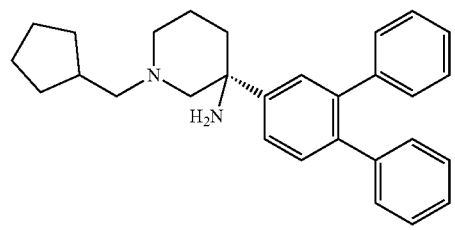 [SMILES: N[C@]1(c2ccc(-c3ccccc3)c(-c3ccccc3)c2)CCCN(CC2CCCC2)C1]
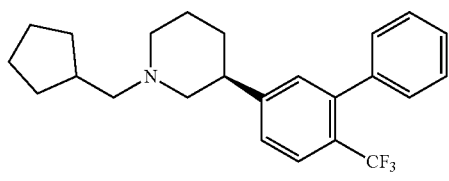 [SMILES: FC(F)(F)c1ccc([C@@H]2CCCN(CC3CCCC3)C2)cc1-c1ccccc1]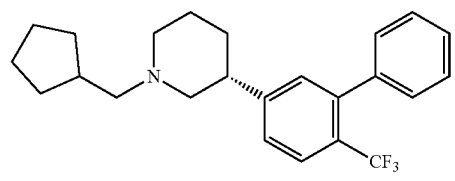 [SMILES: FC(F)(F)c1ccc([C@H]2CCCN(CC3CCCC3)C2)cc1-c1ccccc1]
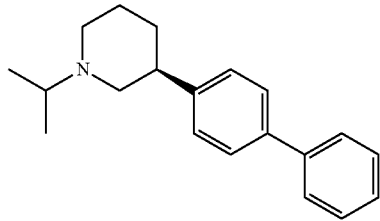 [SMILES: CC(C)N1CCC[C@@H](c2ccc(-c3ccccc3)cc2)C1]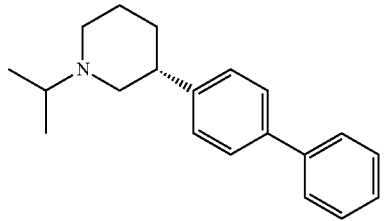 [SMILES: CC(C)N1CCC[C@H](c2ccc(-c3ccccc3)cc2)C1]
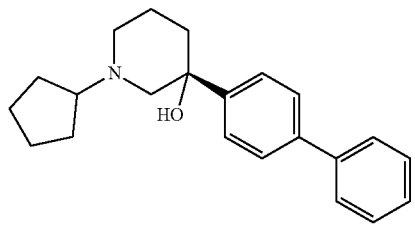 [SMILES: O[C@@]1(c2ccc(-c3ccccc3)cc2)CCCN(C2CCCC2)C1]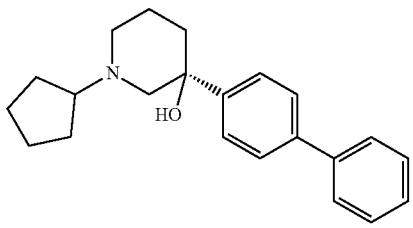 [SMILES: O[C@]1(c2ccc(-c3ccccc3)cc2)CCCN(C2CCCC2)C1]

TABLE 4-continued
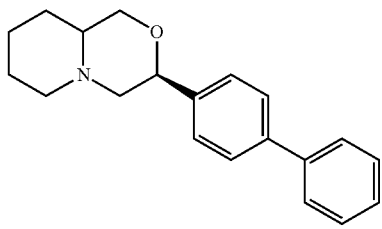 [SMILES: c1ccc(-c2ccc([C@H]3CN4CCCCC4CO3)cc2)cc1] 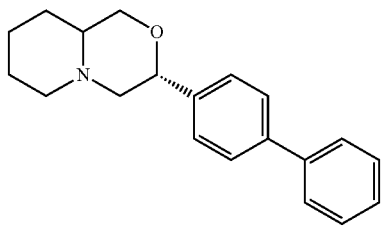 [SMILES: c1ccc(-c2ccc([C@@H]3CN4CCCCC4CO3)cc2)cc1]
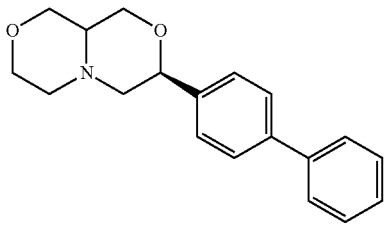 [SMILES: c1ccc(-c2ccc([C@H]3CN4CCOCC4CO3)cc2)cc1] 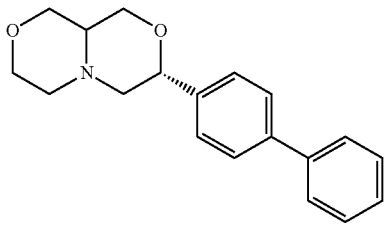 [SMILES: c1ccc(-c2ccc([C@@H]3CN4CCOCC4CO3)cc2)cc1]
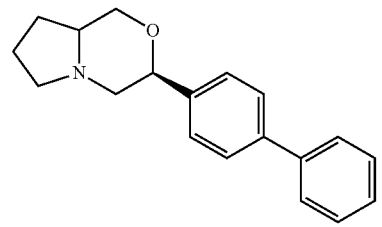 [SMILES: c1ccc(-c2ccc([C@H]3CN4CCCC4CO3)cc2)cc1] 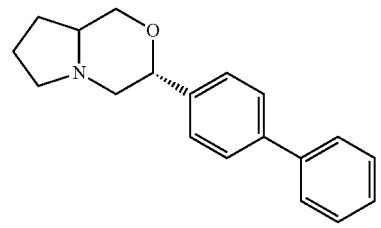 [SMILES: c1ccc(-c2ccc([C@@H]3CN4CCCC4CO3)cc2)cc1]
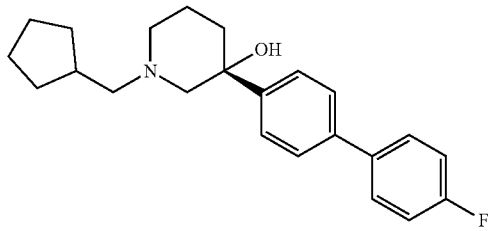 [SMILES: O[C@@]1(c2ccc(-c3ccc(F)cc3)cc2)CCCN(CC2CCCC2)C1] 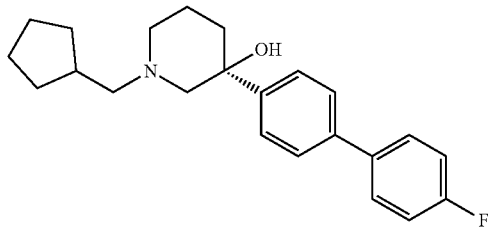 [SMILES: O[C@]1(c2ccc(-c3ccc(F)cc3)cc2)CCCN(CC2CCCC2)C1]
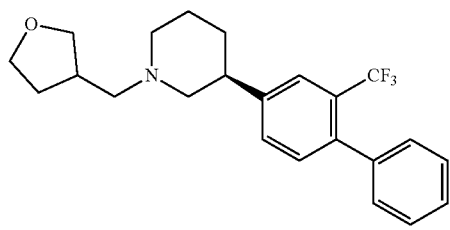 [SMILES: FC(F)(F)c1cc([C@@H]2CCCN(CC3CCOC3)C2)ccc1-c1ccccc1] 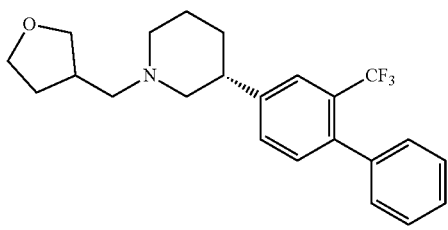 [SMILES: FC(F)(F)c1cc([C@H]2CCCN(CC3CCOC3)C2)ccc1-c1ccccc1]
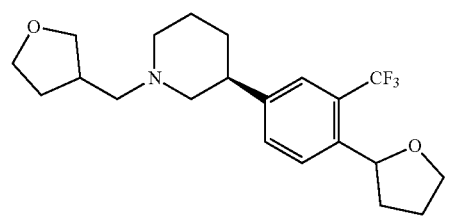 [SMILES: FC(F)(F)c1cc([C@@H]2CCCN(CC3CCOC3)C2)ccc1C1CCCO1] 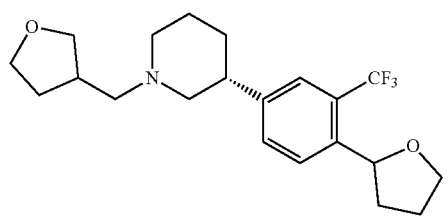 [SMILES: FC(F)(F)c1cc([C@H]2CCCN(CC3CCOC3)C2)ccc1C1CCCO1]

TABLE 4-continued
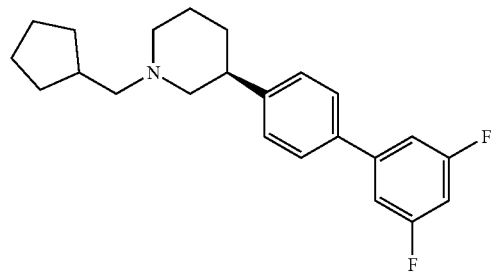 [SMILES: Fc1cc(F)cc(-c2ccc([C@@H]3CCCN(CC4CCCC4)C3)cc2)c1]
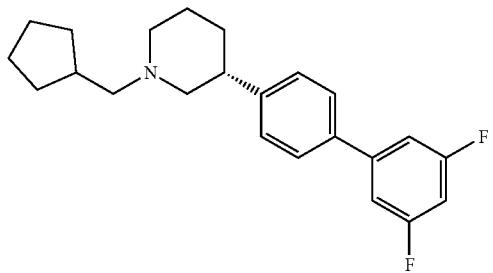 [SMILES: Fc1cc(F)cc(-c2ccc([C@H]3CCCN(CC4CCCC4)C3)cc2)c1]
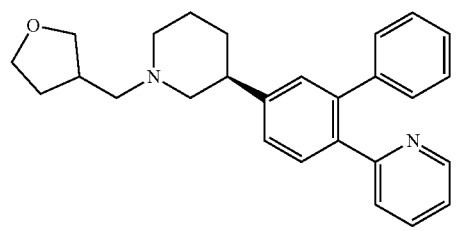 [SMILES: c1ccc(-c2cc([C@@H]3CCCN(CC4CCOC4)C3)ccc2-c2ccccn2)cc1]
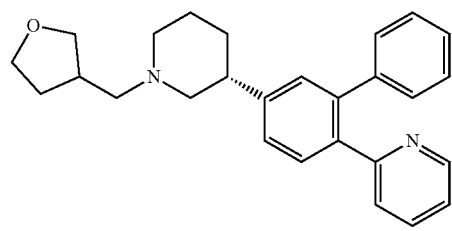 [SMILES: c1ccc(-c2cc([C@H]3CCCN(CC4CCOC4)C3)ccc2-c2ccccn2)cc1]
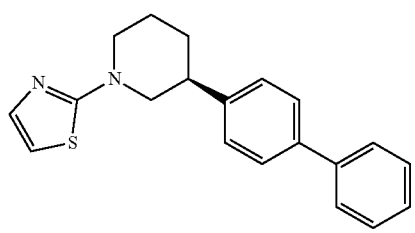 [SMILES: c1ccc(-c2ccc([C@@H]3CCCN(c4nccs4)C3)cc2)cc1]
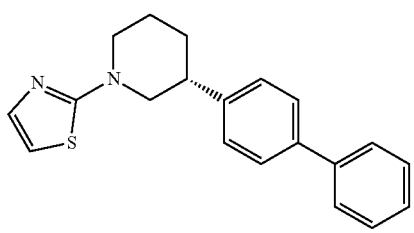 [SMILES: c1ccc(-c2ccc([C@H]3CCCN(c4nccs4)C3)cc2)cc1]
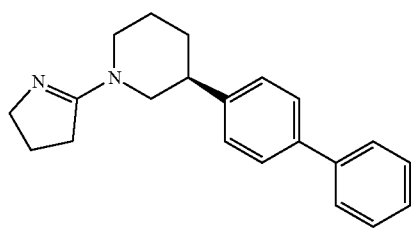 [SMILES: c1ccc(-c2ccc([C@@H]3CCCN(C4=NCCC4)C3)cc2)cc1]
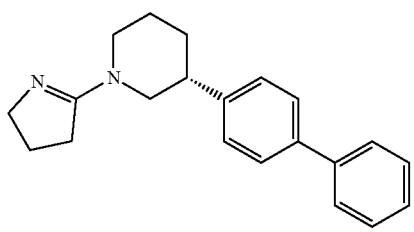 [SMILES: c1ccc(-c2ccc([C@H]3CCCN(C4=NCCC4)C3)cc2)cc1]
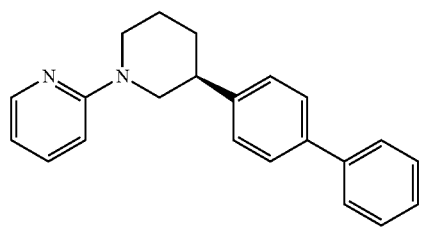 [SMILES: c1ccc(-c2ccc([C@@H]3CCCN(c4ccccn4)C3)cc2)cc1]
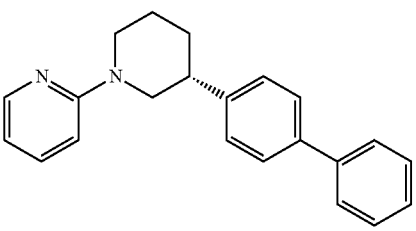 [SMILES: c1ccc(-c2ccc([C@H]3CCCN(c4ccccn4)C3)cc2)cc1]
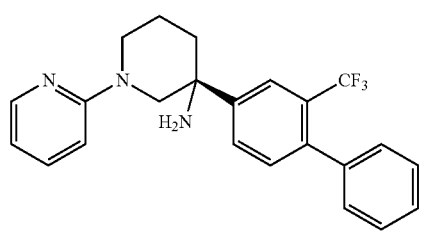 [SMILES: N[C@@]1(c2ccc(-c3ccccc3)c(C(F)(F)F)c2)CCCN(c2ccccn2)C1]
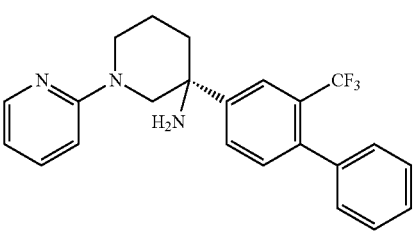 [SMILES: N[C@]1(c2ccc(-c3ccccc3)c(C(F)(F)F)c2)CCCN(c2ccccn2)C1]

TABLE 4-continued
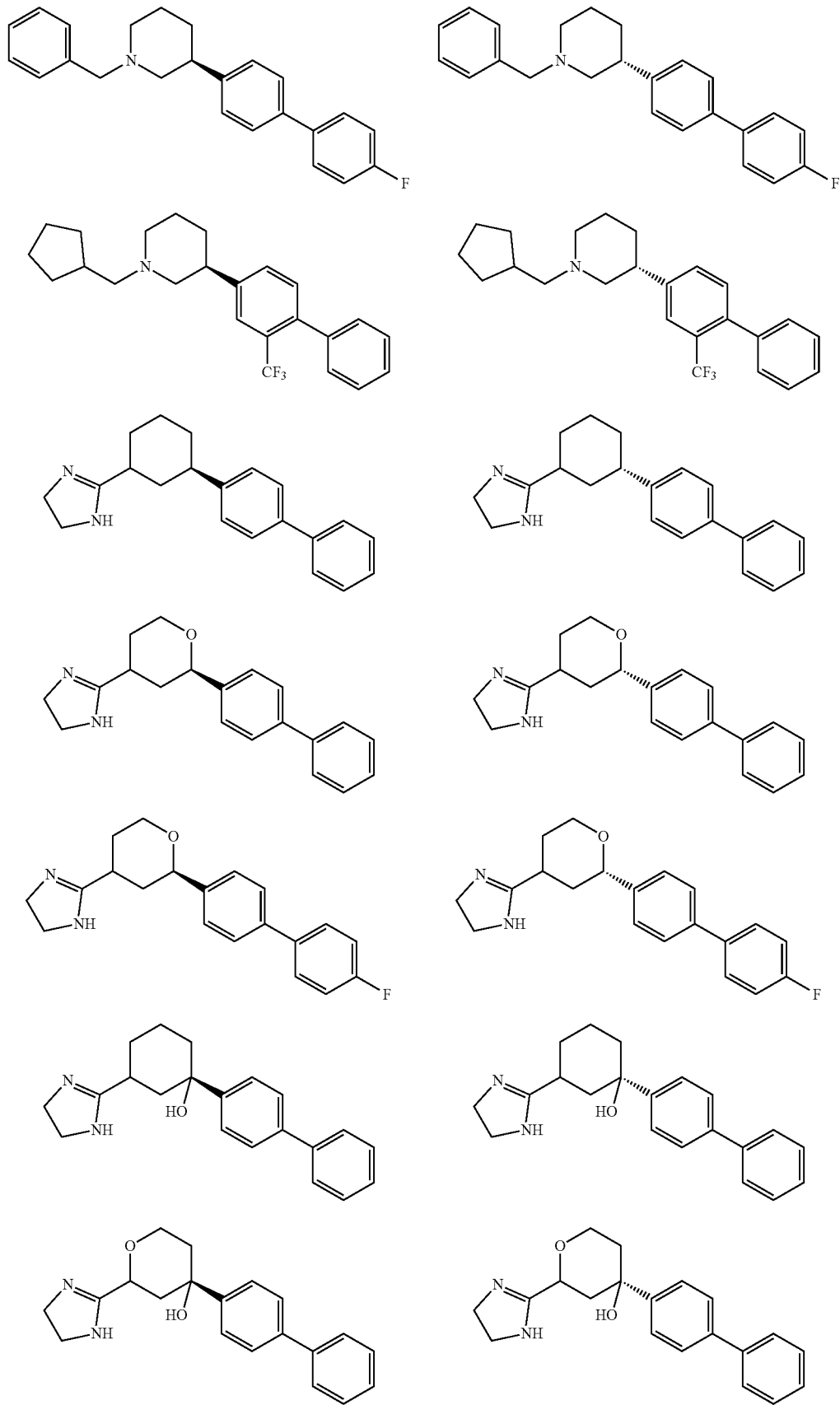

TABLE 4-continued
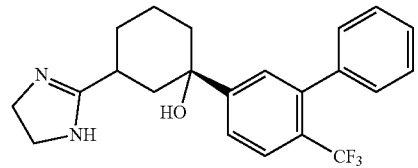 [SMILES: O[C@@]1(c2ccc(C(F)(F)F)c(-c3ccccc3)c2)CCCC(C2=NCCN2)C1]
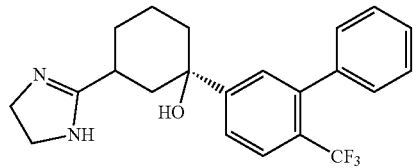 [SMILES: O[C@]1(c2ccc(C(F)(F)F)c(-c3ccccc3)c2)CCCC(C2=NCCN2)C1]
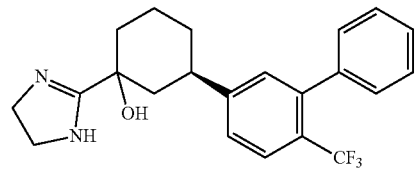 [SMILES: OC1(C2=NCCN2)CCC[C@@H](c2ccc(C(F)(F)F)c(-c3ccccc3)c2)C1]
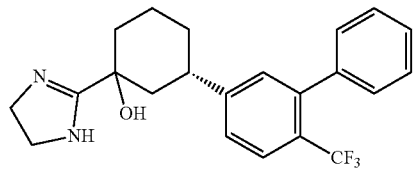 [SMILES: OC1(C2=NCCN2)CCC[C@H](c2ccc(C(F)(F)F)c(-c3ccccc3)c2)C1]
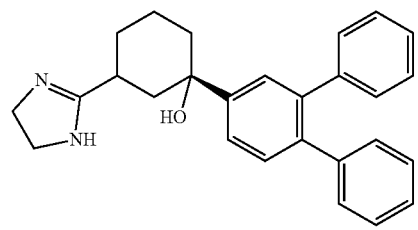 [SMILES: O[C@@]1(c2ccc(-c3ccccc3)c(-c3ccccc3)c2)CCCC(C2=NCCN2)C1]
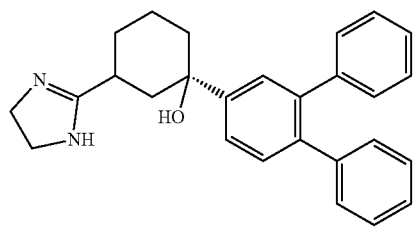 [SMILES: O[C@]1(c2ccc(-c3ccccc3)c(-c3ccccc3)c2)CCCC(C2=NCCN2)C1]
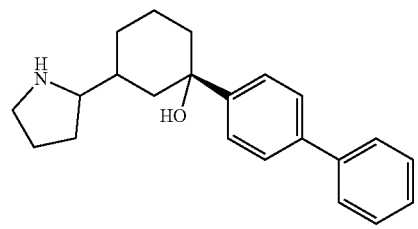 [SMILES: O[C@@]1(c2ccc(-c3ccccc3)cc2)CCCC(C2CCCN2)C1]
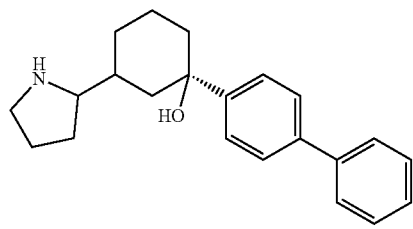 [SMILES: O[C@]1(c2ccc(-c3ccccc3)cc2)CCCC(C2CCCN2)C1]
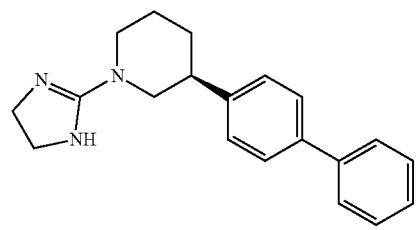 [SMILES: c1ccc(-c2ccc([C@@H]3CCCN(C4=NCCN4)C3)cc2)cc1]
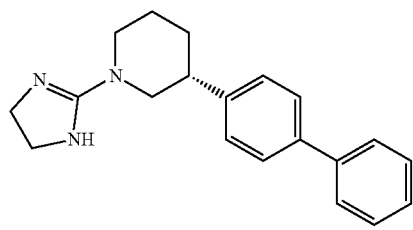 [SMILES: c1ccc(-c2ccc([C@H]3CCCN(C4=NCCN4)C3)cc2)cc1]
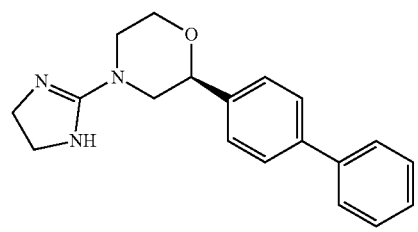 [SMILES: c1ccc(-c2ccc([C@H]3CN(C4=NCCN4)CCO3)cc2)cc1]
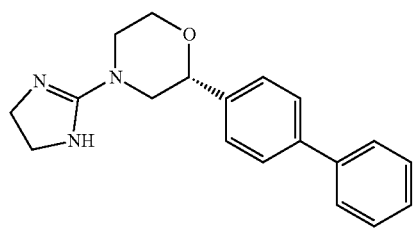 [SMILES: c1ccc(-c2ccc([C@@H]3CN(C4=NCCN4)CCO3)cc2)cc1]
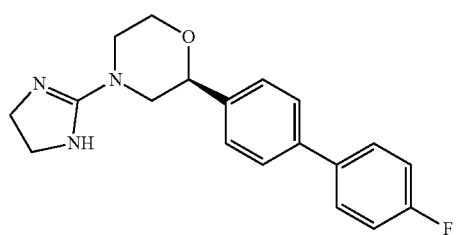 [SMILES: Fc1ccc(-c2ccc([C@H]3CN(C4=NCCN4)CCO3)cc2)cc1]
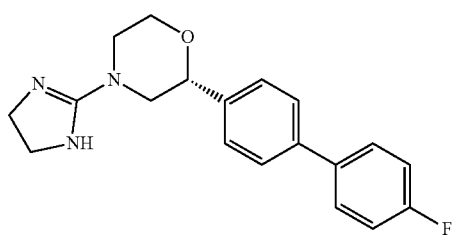 [SMILES: Fc1ccc(-c2ccc([C@@H]3CN(C4=NCCN4)CCO3)cc2)cc1]

TABLE 4-continued

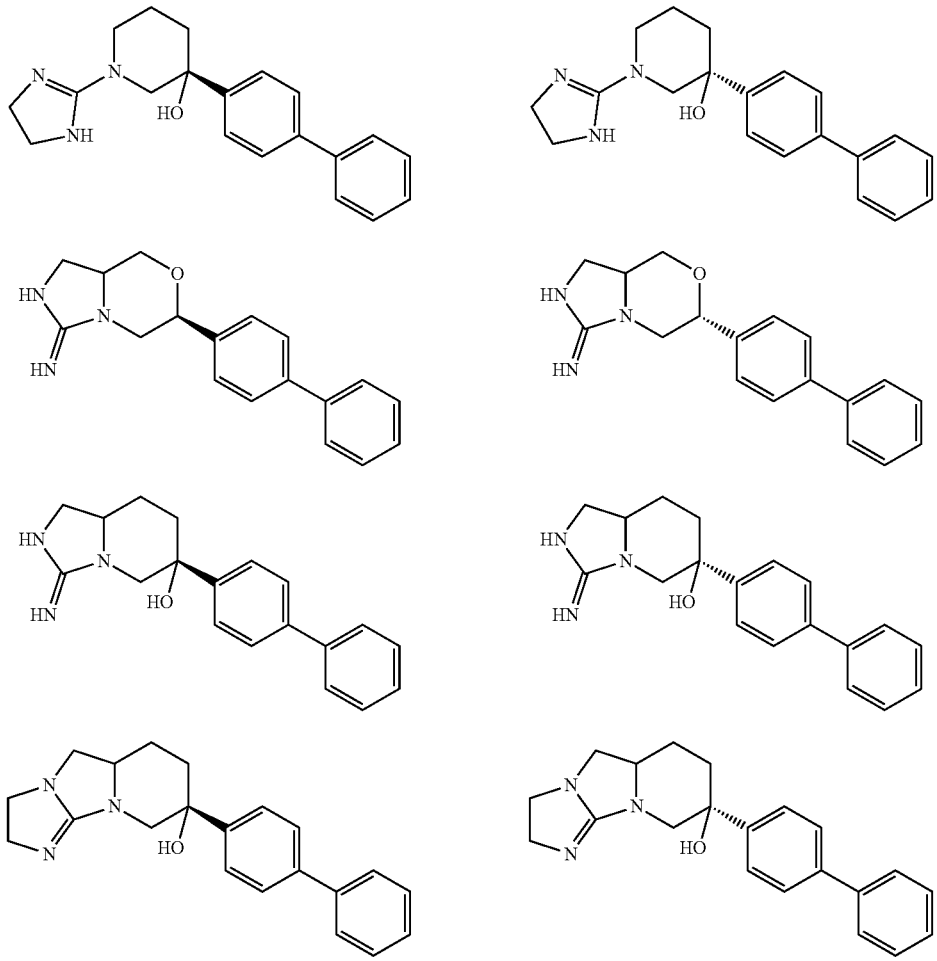

4. Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" or "patient" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition as described herein. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Compounds described throughout, are contemplated to be useful in treating diseases or conditions mediated, at least in part by, PCSK9. Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation," Proc. Natl. Acad. Sci. U.S.A. 100 (3): 928-933 (2003). Similar genes (orthologs) are found across many species. Many enzymes, including PCSK9, are inactive when they are first synthesized, because they have a section of peptide chains that blocks their activity; proprotein convertases remove that section to activate the enzyme.

The PCSK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence can have RefSeq (protein) NP_777596.

PCSK9 is believed to play a regulatory role in cholesterol homeostasis. For example, PCSK9 can bind to the epidermal growth factor-like repeat A (EGF-A) domain of the low-density lipoprotein receptor (LDLR) resulting in LDLR internalization and degradation. Clearly, it would be expected that reduced LDLR levels result in decreased metabolism of LDL-C, which could lead to hypercholesterolemia.

As it is estimated that approximately nine million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (e.g., by increasing the availability of LDLRs and, consequently, LDL-C clearance). Some such drugs, such as Evolocumab (trade name Repatha™ from Amgen, Inc.) and Alirocumab (tradename Praluent™ from Sanofi U.S., LLC and Regeneron Pharmaceuticals, Inc.) have been FDA approved, but are still in clinical trials to determine if they can improve outcomes in heart disease.

Variants of PCSK9 can reduce or increase circulating cholesterol. Abifadel et al., "Mutations in PCSK9 cause autosomal dominant hypercholesterolemia" Nat. Genet. 34 (2): 154-156 (2003). LDL-C is normally removed from the blood when it binds to an LDLR on the surface of liver cells, and is internalized within the hepatocyte as a receptor-ligand complex. When PCSK9 binds to an LDLR, the LDLR is concomitantly degraded along with the complexed LDL particle. However, if a PCSK9 is not bound to an LDLR, the LDLR is recycled after internalization thereby returning to the surface of the cell for removal of more cholesterol.

Disclosed herein are compounds contemplated to have a modulation effect on PCSK9's ability to form an LDLR/PCSK9 complex. In some embodiments, the compounds may bind to a PCSK9 protein and modulate the protein's biological activity. In some embodiments, compounds decrease LDLR/PCSK9 complex formation and are thereby useful to treat various diseases involving lipid dysregulation. In some embodiments, compounds increase LDLR/PCSK9 complex formation and are thereby useful in research and development of therapies relevant to LDL dysregulation.

Without being bound by any particular theory, it is believed that "gain-of-function" (GOF) PCSK9 mutants may result in conditions including, but not limited to, hypercholesterolemia. For example, compounds that bind to a PCSK9 and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Further, and without being bound by any particular theory, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, compounds that bind to a PCSK9 that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The compounds of the present disclosure are therefore useful for treating diseases and conditions mediated, at least in part by, PCSK9, including but not limited to cardiovascular diseases (e.g., a coronary disease) and metabolic diseases. For example, the compounds of the present disclosure are useful for treating diseases and conditions including, but not limited to hypercholesterolemia, atherosclerosis, and hypertension. Further, the compounds of the present disclosure are useful for reducing symptoms including, but not limited to elevated low density lipoprotein receptor density, reduced low density lipoprotein receptor density, symptoms of liver disease or liver dysfunction. The compounds of the present disclosure are also contemplated for reducing symptoms of liver stress, liver dysfunction, or liver disease including conditions such as non-alcoholic fatty liver disease (NAFLD), and for reducing elevated ALT (>55 U/L) and/or AST (>48 U/L) liver enzyme levels. The compounds of the present disclosure are also useful for reducing elevated ALT and/or AST enzymes in patients having elevated dietary fat intake, e.g., above healthy levels (e.g., above recommended daily values as set by the U.S.

USDA). In some embodiments, elevated dietary fat intake is indicated by a saturated fat intake in excess of 10% of total daily calorie intake.

Without being bound to any particular theory, PCSK9 inhibition has been described as useful in the treatment, prevention, or amelioration of symptoms of other conditions, diseases, pathologies, and pathophysiological states. PCSK9 inhibition has been described for treating asthma and allergies (WO2020049026A1), treating cancer or for reducing cancer metastasis (WO2020229718A1), treating inflammatory response to infection and for treating sepsis (US20150140005A1). PCSK9 inhibition has also been described to increase major histocompatibility protein class I (MHC I) proteins on the cell surface of tumor cells (Liu et al., 2020) and may also therefore be beneficial in treating cancers, especially for use in combination with cancer checkpoint inhibitors (e.g., PD-1/PD-L1 therapies) and for increasing antigen presentation as part of the body's immune response. In certain embodiments, provided herein is a method of using a compound described herein to inhibit PCSK9 in the treatment of a disease or condition in a mammal that is mediated, at least in part, by PCSK9 including allergies, asthma, cancer, cancer metastasis, inflammatory response to infection, and sepsis. In certain embodiments, provided herein is a method of treatment of a disease or condition mediated, at least in part, by PCSK9 comprising administering to a subject in need thereof a compound described herein wherein the disease or condition is allergies, asthma, cancer, cancer metastasis, inflammatory response to infection, or sepsis. In certain embodiments, provided herein is a method of using a compound described herein to inhibit PCSK9 to increase MHC I protein expression on the cell surface of tumor cells, or to increase MHC I protein expression by immune system cells. Liu, X., Bao, X., Hu, M. et al. Inhibition of PCSK9 potentiates immune checkpoint therapy for cancer. Nature (2020). https://doi.org/10.1038/s41586-020-2911-7.

Without being bound by any particular theory, it is believed that the administration of a compound of the present disclosure, induces a conformational shift of the PCSK9 protein such that the affinity of the low density lipoprotein binding site for a low density lipoprotein receptor is decreased, wherein PCSK9/LDLR complex formation is decreased. The decrease in PCSK9/LDLR complex formation results in an increase in the bioavailability of LDLR receptors for binding to circulating LDL, thereby increasing the internalization and clearance of LDL by LDLR. It is further believed that administration of the compound may result in increased bioavailability of hepatocyte cell LDLRs.

Further, and also without being bound by any particular theory, it is believed that the administration of a compound of the present disclosure, induces a conformational shift of the PCSK9 protein such that the affinity of the low density lipoprotein binding site for a low density lipoprotein receptor is increased, wherein PCSK9/LDLR complex formation is increased or stabilized. The increase or stabilization in PCSK9/LDLR complex formation results in a decrease in the bioavailability of LDLR receptors for binding to circulating LDL, thereby decreasing the internalization and clearance of LDL by LDLR. It is further believed that a PCSK9 allosteric activator compound may result in decreased bioavailability of hepatocyte cell LDLRs.

In certain embodiments, provided herein is a method of treating a disease or condition mediated, at least in part, by PCSK9, the method comprising administering to a patient in need thereof a therapeutically effective mount of a compound as disclosed herein.

In certain embodiments, provided herein is a method of treating a disease or condition mediated, at least in part, by PCSK9, the method comprising administering to a patient in need thereof a therapeutically effective mount of a compound selected from Table 1, 2 or 3, or a pharmaceutically acceptable salt, prodrug, isomer, or mixture of isomers thereof.

In certain embodiments, provided is a compound as defined herein, for use in the treatment of a disease or condition mediated, at least in part, by PCSK9.

In certain embodiments, provided is use of a compound as defined herein, for the treatment of a disease or condition mediated, at least in part, by PCSK9.

In certain embodiments, provided is use of a compound as defined herein, for the manufacture of a medicament for treating a disease or condition mediated, at least in part, by PCSK9.

In certain embodiments, provided is a method of inhibiting the activity of PCSK9, wherein the method comprises binding a compound as defined herein, to PCSK9, thereby inhibiting the activity of PCSK9.

In certain embodiments, provided is a method of inhibiting the activity of PCSK9, wherein the method comprises binding a compound, as described in Table 1, 2, or 3, or a pharmaceutically acceptable salt, prodrug, isomer, or mixture of isomers thereof, to PCSK9, thereby inhibiting the activity of PCSK9.

In certain embodiments, provided herein is a method of using a compound described herein in the treatment of a disease or condition in a mammal that is mediated, at least in part, by PCSK9. Such diseases or conditions include cardiovascular diseases (e.g., coronary disease, hypertension, hypercholesterolemia, or atherosclerosis), a metabolic diseases (e.g., diabetes), hypocholesterolemia, a disease or condition where the mammal has elevated plasma levels of low density lipoprotein cholesterol, and a disease or condition where the mammal has suppressed plasma levels of low density lipoprotein cholesterol. Therefore, in certain embodiments, a compound described herein is of use as a medicament for the treatment of the aforementioned diseases or conditions.

In certain embodiments, provided herein is a method of using a compound described herein to bind and modulate the biological activity of PCSK9 protein. In certain embodiments, provided herein is a method of using a compound described herein to bind and inhibit the biological activity of PCSK9 protein. In certain embodiments, provided herein is a compound described herein for use in the inhibition of PCSK9. In certain embodiments, provided herein is a compound described herein for use in the reduction of PCSK9-induced LDLR degradation. In certain embodiments, provided herein is a compound described herein for use in the treatment of hypercholesterolemia. In certain embodiments, provided herein is a compound described herein for use in the treatment of PCSK9-related disorders. In certain embodiments, provided herein is a compound described herein for use in the reduction of PCSK9 activity.

In some embodiments, provided is a method of treating a disease or condition mediated, at least in part, by PCSK9, the method comprising administering to a patient in need thereof an effective amount of a Compound

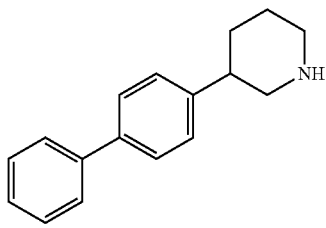 [SMILES: c1ccc(-c2ccc(C3CCCNC3)cc2)cc1]

or a pharmaceutically acceptable salt, prodrug, deuterated analog, stereoisomer, or mixture of stereoisomers thereof.

In some embodiments, provided is a method of treating a disease or condition mediated, at least in part, by PCSK9, the method comprising administering to a patient in need thereof an effective amount of a Compound

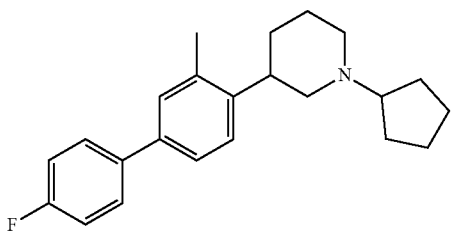

or a pharmaceutically acceptable salt, prodrug, deuterated analog, stereoisomer, or mixture of stereoisomers thereof.

Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" The Lancet 2003; 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" BMJ 337: a993. Genetic abnormalities are in some cases completely responsible for hypercholesterolemia, such as in familial hypercholesterolemia where there is one or more genetic mutations in the autosomal dominant APOB gene, the autosomal recessive LDL-RAP1 gene, autosomal dominant familial hypercholesterolemia (HCHOLA3) variant of the PCSK9 gene, or the LDL receptor gene. "Hypercholesterolemia" Genetics Home Reference U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia," eMedicine Medscape, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" Adv Physiol Educ 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" Circulation 109(23 Suppl 1): III 2-7. In contrast, higher levels of HDL cholesterol are protective. Kontush et al., (2006) "Antiatherogenic small, dense HDL—guardian angel of the arterial wall?" Nat Clin Pract Cardiovasc Med 3(3):144-153. Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood. These fats are called lipids. There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" BMJ 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn A V, Nakano M, Narula J, Kolodgie F D, Virmani R (July 2010). "Concept of vulnerable/unstable plaque" Arterioscler. Thromb. Vasc. Biol. 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" Circulation 97(18):1876-1887.

Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" Circulation 86 (3): 1046-1060; and Suarez E. C., (1999) "Relations of trait depression and anxiety to low lipid and lipoprotein concentrations in healthy young adult women". Psychosom Med 61(3): 273-279. It is also possible that whatever causes the low cholesterol level also causes mortality, and that the low cholesterol is simply a marker of poor health.

In some embodiments, hypercholesterolemia is indicated by elevated total cholesterol values and/or elevated LDL cholesterol values, for example, total cholesterol (TC) >200 mg/dL, 200-239 mg/dL, or >240 mg/dL, and/or LDL >70 mg/dL, 70-100 mg/dL, >100, or >160 mg/dL. Age may also be taken into account, for example, an LDL of >160 mg/dL may be considered elevated enough to warrant lipid lowering in adults under 40 years, while adults 40-75 with LDL between 70 and 190 mg/dL could be indicated for lipid lowering treatment based on the patient's individual risk profile. In some embodiments, hypercholesterolemia may be determined by a medical practitioner, e.g., following American Heart Association guidelines.

Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy. Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

In some embodiments, pre-diabetes may be indicated by one of more of: A1C of 5.7%-6.4%, fasting plasma glucose of 100-125 mg/dL, and/or plasma glucose of 140-199 mg/dL at 2-hour post 75 g oral glucose challenge.

In some embodiments, a patient exhibits reduced levels of ALT and/or AST following a course of treatment. In some embodiments, the reduction in ALT and/or AST is at least 5%, at least 10%, at least 20%, at least 30%, at least 40%, at least 50%, at least 60%, or at least 70% relative to pre-treatment levels, or a range of values between any two listed.

In some embodiments, a patient exhibits reduced LDL levels following a course of treatment. In some embodiments, the reduction in LDL levels is at least 5%, at least 10%, at least 20%, at least 30%, at least 40%, at least 50%, at least 60%, or at least 70% relative to pre-treatment levels, or a range of values between any two listed.

Combination Therapy

Patients being treated by administration of the compounds of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like.

Cardiovascular Agent Combination Therapy

Cardiovascular related diseases or conditions that can benefit from a combination treatment of the compounds of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the compounds of the disclosure with therapeutic agents suitable for treating cardiovascular related conditions allows enhancement in the standard of care therapy the patient is currently receiving. In some embodiments, the compounds of the disclosure are co-administered with ranolazine (RANEXA®).

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein IIb/IIIa inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include ezetimibe (Zetia®), bempedoic acid (Nexletol®), bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

PCSK9 Inhibitors

Drugs that block PCSK9 biological actions are believed to lower circulating low-density lipoprotein cholesterol (LDL-C) levels (e.g., by increasing the availability of LDLRs and, consequently, LDL-C clearance). Examples include FDA approved Evolocumab (trade name Repatha™ from Amgen, Inc.) and FDA approved Alirocumab (tradename Praluent™ from Sanofi U.S., LLC and Regeneron Pharmaceuticals, Inc.).

Additional Combination Therapies

A patient presenting with an acute coronary disease event often suffers from secondary medical conditions such as one or more of a metabolic disorder, a pulmonary disorder, or a peripheral vascular disorder. Such patients can benefit from treatment of a combination therapy comprising administering to the patient a compound of the disclosure in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Accordingly, one aspect of the disclosure provides for a composition comprising the compounds of the disclosure and at least one therapeutic agent. In an alternative embodiment, the composition comprises the compounds of the disclosure and at least two therapeutic agents. In further alternative embodiments, the composition comprises the compounds of the disclosure and at least three therapeutic agents, the compounds of the disclosure and at least four therapeutic agents, or the compounds of the disclosure and at least five therapeutic agents.

The methods of combination therapy include co-administration of a single formulation containing the compounds of the disclosure and therapeutic agent or agents, essentially contemporaneous administration of more than one formulation comprising the compounds of the disclosure and therapeutic agent or agents, and consecutive administration of a compound of the disclosure and therapeutic agent or agents, in any order, wherein preferably there is a time period where the compounds of the disclosure and therapeutic agent or agents simultaneously exert their therapeutic effect.

These and other embodiments of the present disclosure will readily occur to those of ordinary skill in the art in view of the disclosure herein and are specifically contemplated.

5. Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, bottle, bag, ampoule, preloaded syringe, and intravenous bag.

6. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof (collectively and individually, "active ingredient") and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., *Remington's Pharmaceutical Sciences*, Mace Publishing Co., Philadelphia, Pa. 17th Ed. (1985); and *Modern Pharmaceutics*, Marcel Dekker, Inc. 3rd Ed. (G. S. Banker & C. T. Rhodes, Eds.). The pharmaceutical compositions may comprising from about 0.01% to about 90% of an active ingredient described herein.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

7. Dosing

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound described herein may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

8. Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), Larock's Comprehensive Organic Transformations (VCH Publishers Inc., 1989), Heterocyclic Chemistry (Blackwell Publishing, 4$^{th}$ Edition, 2002), Vogel's Textbook of Practical Organic Chemistry (Prentice Hall, 5$^{th}$ Edition, 1996).

The term "solvent" refers to an organic medium which is generally a liquid under the conditions of the reaction being described in conjunction therewith, and in which a reaction takes place (including, for example, benzene, toluene, acetonitrile, tetrahydrofuran ("THF"), dimethylformamide ("DMF"), chloroform, methylene chloride (or dichloromethane), diethyl ether, methanol, pyridine and the like).

The terms "inert organic solvent" and "inert solvent" refer to a solvent that is inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like).

The compounds may be characterized by NMR (nuclear magnetic resonance), such as $^1$H NMR, spectra. The following abbreviations are used for reporting NMR data: δ (chemical shift (ppm)), s (singlet), d (doublet), t (triplet), m (multiplet), br (broadened), dd (doublet of doublets), dt (doublet of triplets). Coupling constant (J) is expressed in hertz (Hz).

In the following exemplary schemes, Ring A, Ring B, m, $X^1$, $X^2$, $X^3$, $X^4$, $X^5$, $R^6$, $Z^1$, $Z^2$, $Z^3$, $R^1$, $R^2$, $R^4$, $R^7$, $R^8$, and $R^9$ are as defined herein.

Scheme I shows an exemplary example of a synthetic route for preparing compounds of Formula I as described herein.

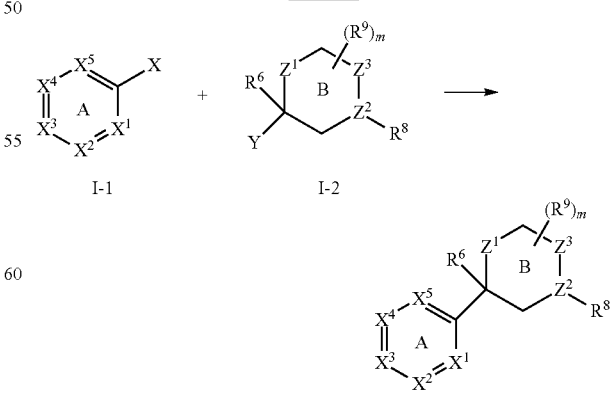

In Scheme I, X is triflate, Cl, Br, or I, Y is BF$_2$, boronic acid or a boronic ester, and compounds I-1 and I-2 react in the presence of a catalyst, such as a palladium or nickel catalyst, under cross-coupling conditions, such as Suzuki or Suzuki-Miyaura reaction conditions, to form a compound of formula I.

Alternatively, in Scheme I, X is triflate, Cl, Br, or I, Y is MgBr, and compounds I-1 and I-2 react in the presence of a catalyst, such as a palladium or nickel catalyst, under Kumada Coupling reaction conditions, to form a compound of formula I.

Scheme II shows an exemplary example of a synthetic route for preparing compounds of Formula X as described herein.

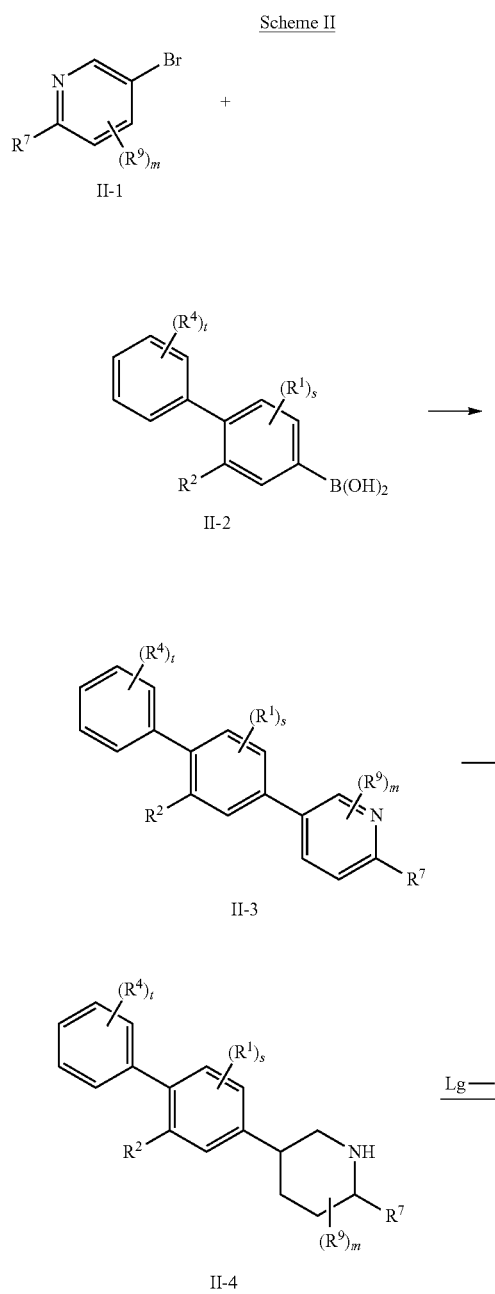

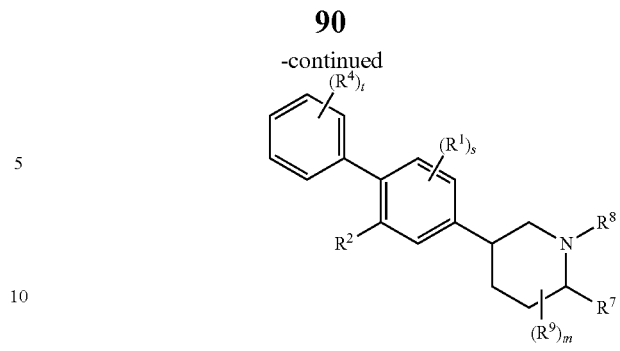

In Scheme II, compound II-3 is prepared by reaction of compounds II-1 and II-2 under cross-coupling conditions, such as in the presence of a base (e.g., Cs$_2$CO$_3$) and a catalyst (e.g., Pd(PPh$_3$)$_4$). The reaction can be conducted in a solvent, such as dioxane, water or a mixture thereof. The reaction can be conducted at a temperature of about 80° C. or above, such as about 80° C. to about 120° C.

Compound II-3 is converted to Compound II-4 under hydrogenation conditions, such as under a H$_2$ gas pressure in the presence of a catalyst, such as Pd on carbon. The hydrogenation can be conducted in a solvent, such as acetic acid, methanol, DCM, or a combination thereof, optionally with heating, such as at a temperature of about 40° C. to about 80° C.

Compound II-4 reacts with compound R$^8$-Lg to form a compound of Formula X, wherein Lg is a leaving group, such as Cl, Br, tosylate (OTs), mesylate (OMs) or triflate (OTf).

EXAMPLES

Example 1: Synthesis

Preparation of Compound 1,006: 3-([1,1'-biphenyl]-4-yl)-1-(cyclopentylmethyl)piperidine

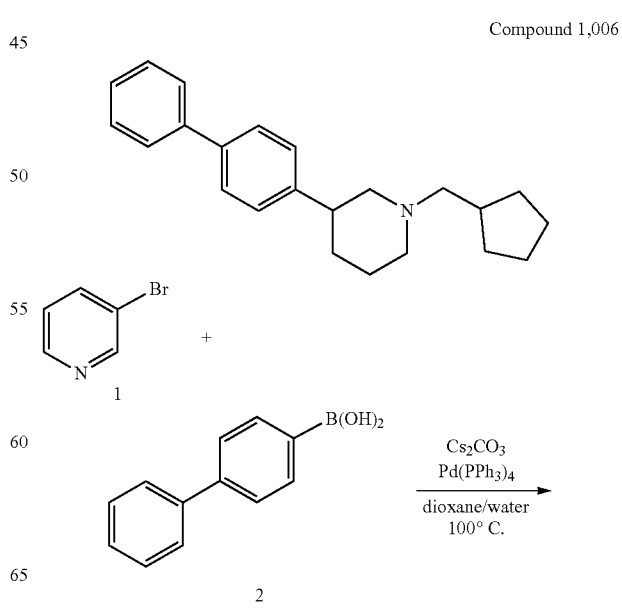

Step 3: Synthesis of 3-([1,1'-biphenyl]-4-yl)-1-(cyclopentyl methyl)piperidine. Compound 1,006

To a stirred solution of compound 4 (200 mg, 0.83 mmol) in acetone (7 mL), were added compound 5 (270 mg, 1.67 mmol) and K$_2$CO$_3$ (370 mg, 2.49 mmol.). The resulting reaction mixture was heated to 70° C. for 12 h in a sealed tube. After completion of the reaction, the reaction mixture was filtered and the filtrate was concentrated. The crude residue was purified by silica gel column chromatography [gradient elution with 5% MeOH in DCM] to afford Compound 1,006, 3-([1,1'-biphenyl]-4-yl)-1-(cyclopentylmethyl)piperidine (50 mg, 10%). LC-MS (m/z): 320.2 [M+H]$^+$. $^1$H NMR (400 MHz, dmso-d6): δ 7.67-7.64 (m, 4H), 7.48-7.44 (t, J=7.6 Hz, 2H), 7.39-7.36 (m, 3H), 4.06-40.3 (m, 2H), 3.56-3.06 (m, 5H), 2.33-2.29 (t, J=8 Hz, 1H), 1.94-1.5 (m, 10H), 1.27-1.22 (m, 2H).

Compounds 1,002, 1,004, 1,007, and 1,008 were prepared according to the method described with respect to Compound 1,006 with substitution of an appropriate electrophile in place of compound 5.

Preparation of Compound 1,009: 1-(cyclopentylmethyl)-3-(4'-fluoro-[1,1'-biphenyl]-4-yl)piperidine

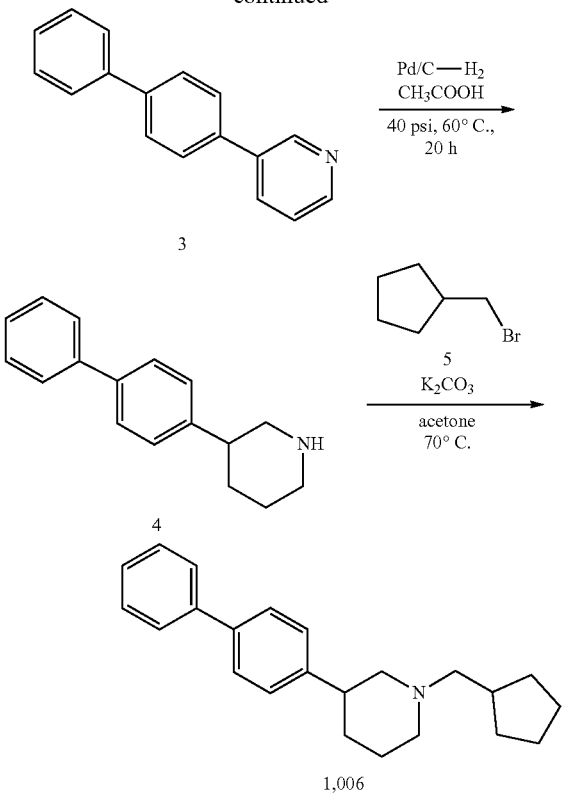

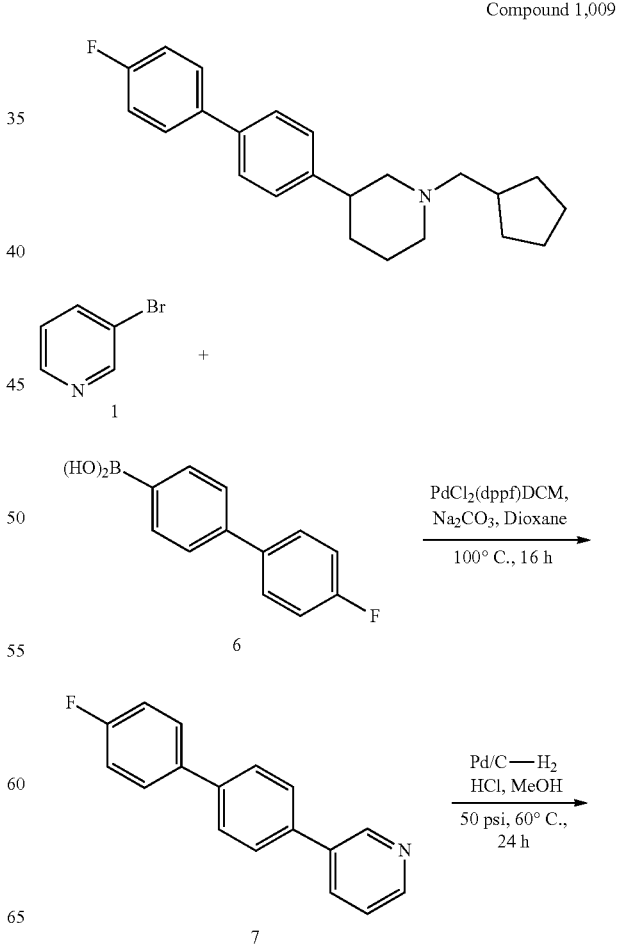

Step 1: Synthesis of 3-([1,1'-biphenyl]-4-yl)pyridine (3)

To a mixture of compound 1 (500 mg, 3.18 mmol) and compound 2 (761 mg, 3.82 mmol) in dioxane:water (9:1) (10 mL) was added Cs$_2$CO$_3$ (2.08 g, 6.36 mmol) and the resulting mixture was degassed with N$_2$ for 20 min. Pd(PPh$_3$)$_4$ (370 mg, 0.318 mmol) was added and the reaction mixture was heated to 100° C. for 12 h. After completion of the reaction, the reaction mixture was filtered through a Celite pad. The filtrate was concentrated and purified by silica gel column chromatography [gradient elution with 20% EtOAc in Hexane] to afford compound 3 (400 mg, 54%). $^1$H NMR (400 MHz, DMSO-d$_6$): δ 8.96 (s, 1H), 8.60-8.58 (dd, J=1.6 Hz, 1H), 8.15-8.13 (dd, J=0.8 Hz, 1H), 7.86-7.80 (m, 4H), 7.75-7.73 (dd, J=1.2 Hz, 2H), 7.52-7.50 (m, 3H), 7.49-7.40 (m, 1H).

Step 2: Synthesis of 3-([1,1'-biphenyl]-4-yl)piperidine (4)

To a stirred solution of compound 3 (400 mg, 1.73 mmol) in acetic acid (7 mL), was added 10% Pd/C (50% wet) (200 mg). The reaction mixture was stirred under hydrogen (40 psi) at 60° C. for 24 h. After completion of the reaction, the reaction mixture was filtered through a Celite pad and the filtrate was basified with a saturated NaHCO$_3$ solution and extracted with ethyl acetate (50 mL×3). The combined organic layers were dried over sodium sulfate and concentrated to afford compound 4 (300 mg, 70%). LC-MS (m/z): 238.4 [M+H]$^+$. $^1$H NMR (400 MHz, DMSO-d$_6$): δ 7.63-7.61 (m, 4H), 7.57-7.55 (d, J=8 Hz, 2H), 7.46-7.42 (d, J=16 Hz, 2H), 7.35-7.30 (m, 3H), 3.00-2.92 (m, 3H), 2.63-2.48 (m, 3H), 1.67-1.35 (m, 7H).

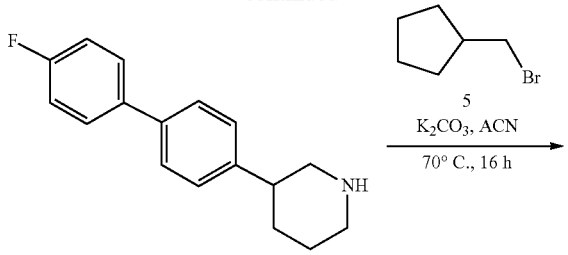
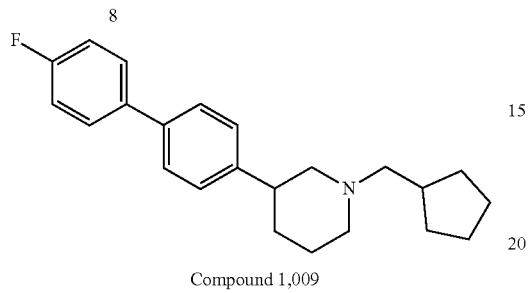

Step 1: Synthesis of 3-(4'-fluoro-[1,1'-biphenyl]-4-yl) pyridine (7)

To a stirred solution of compound 1 (1 g, 46.29 mmol), compound 6 (1.09 g, 69.44 mmol) in 1,4-dioxane and water (9:1) (10 mL) was added $Na_2CO_3$ (0.98 g, 92.59 mmol) and the resulting mixture was degassed with $N_2$ for 20 min. $PdCl_2(dppf) \cdot CH_2Cl_2$ complex (169 mg, 2.08 mmol) was added and the resulting reaction mixture was heated to 100° C. for 12 h. After completion of the reaction, the solution was filtered through a Celite pad. The filtrate was concentrated and purified by silica gel column chromatography [gradient elution with 10% EtOAc in Hexane] to afford compound 7 (1g, 61%). LCMS (m/z): 250.1 $[M+H]^+$.

Step 2: Synthesis of 3-(4'-fluoro-[1,1'-biphenyl]-4-yl) piperidine (8)

To a stirred solution of compound 7 (500 mg, 1.73 mmol) in concentrated HCl (7 mL) was added 10% Pd/C (50% wet) (200 mg) and the resulting suspension was stirred under a hydrogen atmosphere (50 psi) at 60° C. for 24 h. After completion of the reaction, the mixture was filtered through a Celite pad and the filtrate was concentrated to afford compound 8 (200 mg, 51%). LCMS (m/z): 256.2 $[M+H]^+$.
$^1H$ NMR (400 MHz, DMSO-$d_6$): δ 9.06 (s br, 1H), 7.69-7.28 (m, 4H), 3.04-2.90 (m, 4H), 3.21-2.82 (m, 4H), 2.07-1.59 (m, 4H), 1.42-1.03 (m, 1H).

Step 3: Synthesis of 1-(cyclopentylmethyl)-3-(4'-fluoro-[1,1'-biphenyl]-4-yl)piperidine Compound 1,009

To a stirred solution of compound 8 (200 mg, 0.83 mmol) in acetonitrile (7 mL) was added $K_2CO_3$ (370 mg, 2.49 mmol) and compound 5 (270 mg, 1.67 mmol). The reaction mixture was stirred at 70° C. for 16 h in a sealed tube. After completion of the reaction, the reaction mixture was filtered and the filtrate was concentrated to dryness. The residue was further purified by silica gel column chromatography [gradient elution with 5% MeOH in DCM] to afford compound 1,009, 1-(cyclopentylmethyl)-3-(4'-fluoro-[1,1'-biphenyl]-4-yl)piperidine (25 mg, 10%). LCMS (m/z): 338.3 $[M+H]^+$.
$^1H$ NMR (400 MHz, $CDCl_3$): δ 7.53-7.46 (m, 4H), 7.31 (d, J=8 Hz, 2H), 7.107 ((t, J=8.8 Hz, 2H),), 3.03-2.84 (m, 3H), 2.3 (d, J=7.2 Hz, 2H), 2.10-1.92 (m, 4H), 1.77-1.71 (m, 4H), 1.52-1.42 (m, 4H), 1.29-1.23 (m, 3H).

Preparation of Compound 1,010: 3-(4'-chloro-[1,1'-biphenyl]-4-yl)-1-(cyclopentylmethyl) piperidine

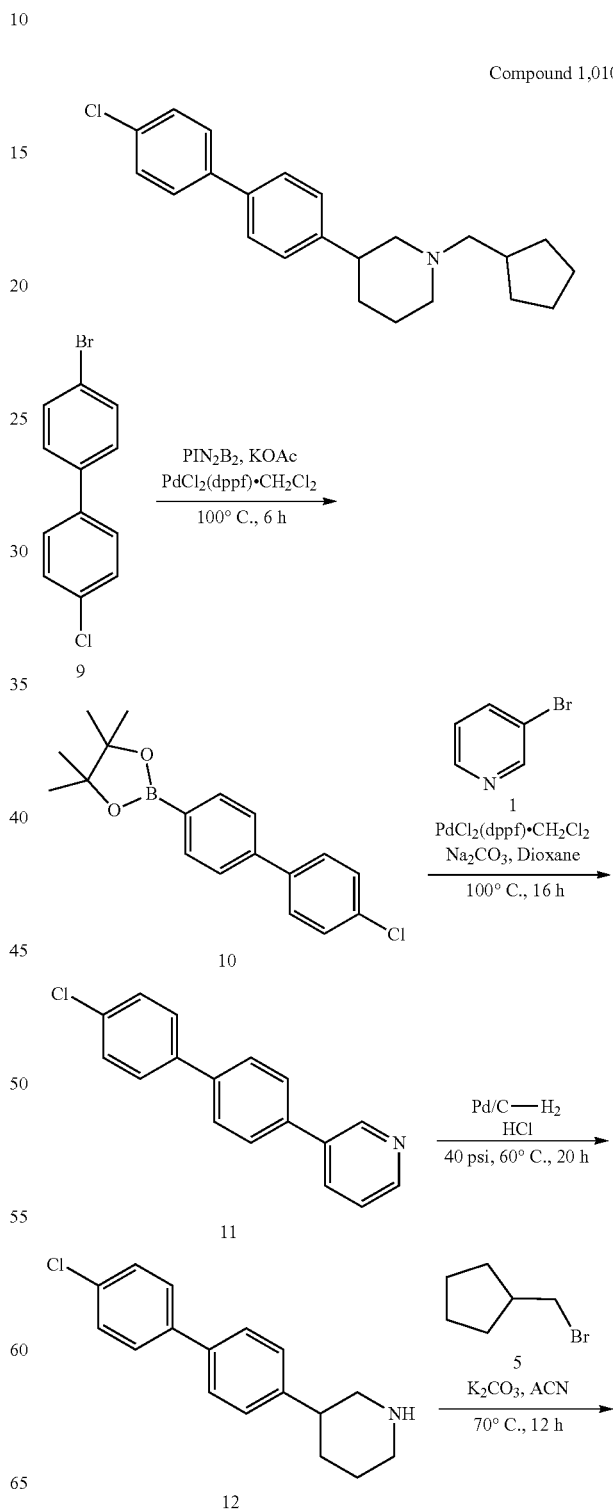

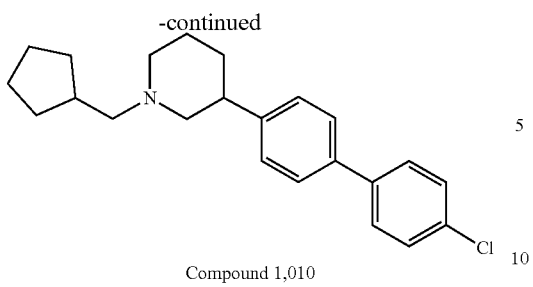

Compound 1,010

Step 1: Synthesis of 2-(4'-chloro-[1,1'-biphenyl]-4-yl)-4,4,5,5-tetramethyl-1,3,2-dioxaborolane (10)

To a mixture of compound 9 (2.0 g, 74.76 mmol) and (Pin)$_2$B$_2$ (3.7 g, 149.53 mmol) in dioxane-water (9:1) (25 mL) was added KOAc (1.46 g, 149.53 mmol) and the resulting mixture was degassed with N$_2$ for 20 min. PdCl$_2$(dppf).CH$_2$Cl$_2$ complex (246 mg, 3.36 mmol) was added and the reaction mixture was heated to 100° C. for 12 h. After completion of the reaction, the solution was filtered through a Celite pad and the filtrate was concentrated to afford compound 10 (2 g, crude).

Step 2: Synthesis of 3-(4'-chloro-[1,1'-biphenyl]-4-yl) pyridine (11)

To a mixture of compound 10 (2.0 g, 63.69 mmol) and compound 1 (1.5 g, 95.54 mmol) in dioxane: water (9:1) (25 mL) was added Na$_2$CO$_3$ (1.35 g, 127.38 mmol) and the resulting mixture was degassed with N$_2$ for 20 min. PdCl$_2$(dppf).CH$_2$Cl$_2$ complex (209 mg, 2.86 mmol) was added and the reaction mixture was heated to 100° C. for 12 h. After completion of the reaction, the solution was filtered through a Celite pad and the filtrate was concentrated to dryness and purified by silica gel column chromatography [gradient elution with 10% EtOAc in Hexane] to afford compound 11 (800 mg (50%). LCMS (m/z): 266.3 [M+H]$^+$. $^1$H NMR (400 MHz, CDCl$_3$): δ 8.90 (dd, J=2.3, 0.9 Hz, 1H), 8.61 (dd, J=4.8, 1.6 Hz, 1H), 7.95-7.9 (m, 1H), 7.67 (s, 4H), 7.60-7.54 (m, 2H), 7.45-7.39 (m, 3H), Step 3: Synthesis of 3-(4'-chloro-[1,1'-biphenyl]-4-yl) piperidine (12)

To a stirred solution of compound 11 (100 mg, 0.37 mmol) in MeOH (2 mL) and concentrated HCl (0.5 mL) was added PtO$_2$ (50% wet) (50 mg,) and the resulting suspension was stirred under hydrogen (50 psi) at 45° C. for 12 h. After completion of the reaction, the mixture was filtered through a Celite pad. The filtrate was basified with a saturated NaHCO$_3$ solution and extracted with ethyl acetate (3×10 mL). The combined organic layer was dried over anhydrous sodium sulfate, filtered and concentrated to afford compound 12 (60 mg, 60%). LCMS (m/z): 272.1 [M+H]$^+$.

Step 4: Synthesis of 3-(4'-chloro-[1,1'-biphenyl]-4-yl)-1-(cyclopentylmethyl) piperidine Compound 1,010

To a stirred solution of compound 12 (150 mg, 0.55 mmol) in acetonitrile (2 mL) was added K$_2$CO$_3$ (229 mg, 1.66 mmol) and compound 5 (180 mg, 1.10 mmol). The reaction mixture was stirred at 70° C. for 12h in sealed tube. After completion of the reaction, the mixture was filtered, and the filtrate was concentrated to dryness. The residue was purified by silica gel column chromatography to afford compound 1,010, 3-(4'-chloro-[1,1'-biphenyl]-4-yl)-1-(cyclopentylmethyl) piperidine (25 mg, 10%). LCMS (m/z): 354.3 [M+H]$^+$ $^1$H NMR (400 MHz, CDCl$_3$): δ 7.51-7.47 (m, 4H), 7.40-7.37 (m, 2H), 7.31 (d, J=8.0 Hz, 2H), 3.03-2.82 (m, 3H), 2.30 (d, J=1.2 Hz, 2H), 2.29-1.92 (m, 4H), 1.77-1.73 (m, 4H), 1.57-1.45 (m, 4H), 1.25-1.17 (m, 3H).

Preparation of Compound 1,011: 1-(cyclopentylmethyl)-3-(4'-(trifluoromethyl)-[1,1'-biphenyl]-4-yl) piperidine

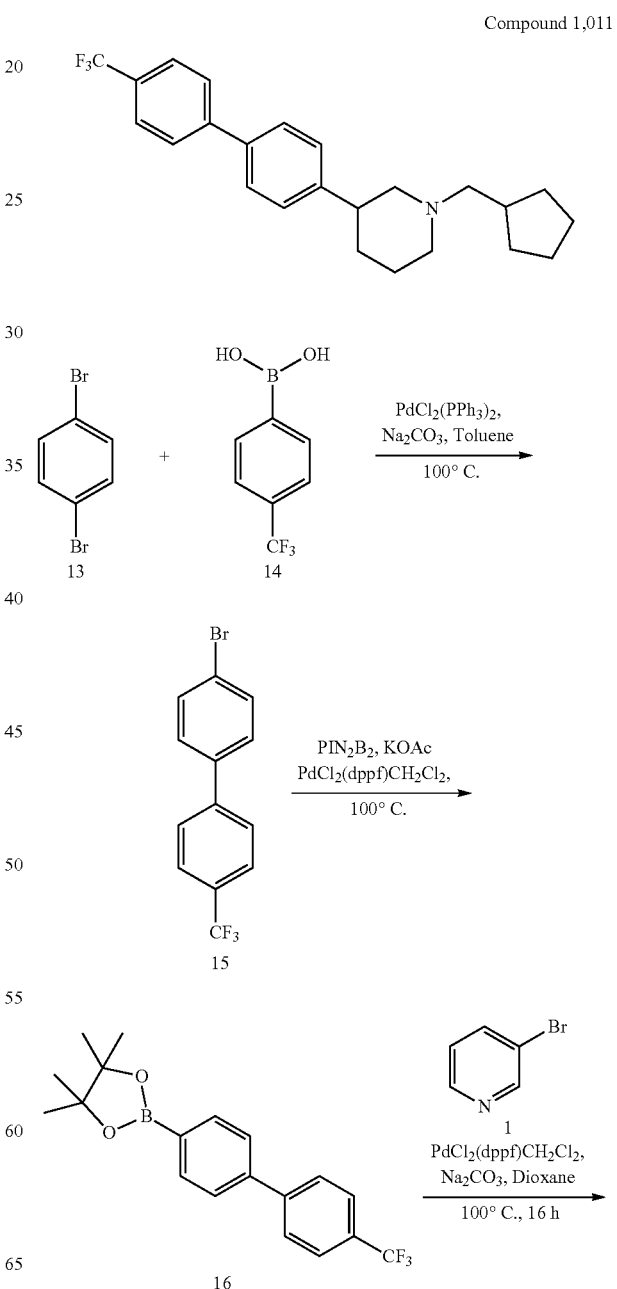

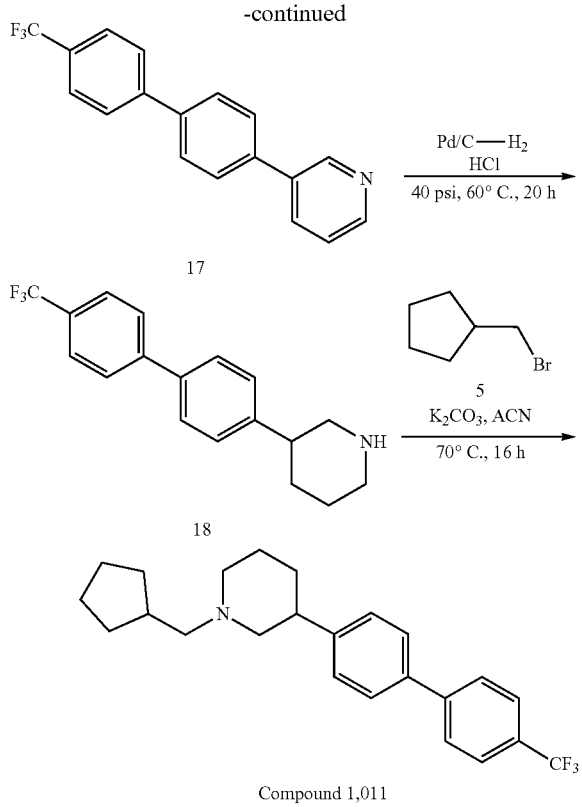

Step 1: Synthesis of 4-bromo-4'-(trifluoromethyl)-1,1'-biphenyl (15)

To a mixture of compound 13 (200 mg, 0.84 mmol) and compound 14 (241 mg, 1.27 mmol) in toluene:water (9:1) (6 mL) was added $Na_2CO_3$ (180 mg, 1.69 mmol) and the resulting mixture was degassed with $N_2$ for 20 min. $PdCl_2$(dppf).$CH_2Cl_2$ complex (59 mg, 0.08 mmol) was added and the reaction mixture was further heated to 100° C. for 12 h. After completion of the reaction, the mixture was filtered through a Celite pad, and the filtrate was concentrated to dryness. The crude residue was further purified by silica gel column chromatography to afford compound 15 (95 mg, 54%). $^1$HNMR (400 MHz, $CDCl_3$): δ 7.76-7.63 (m, 4H), 7.62-7.58 (m, 2H), 7.49-7.44 (m, 2H).

Step 2: Synthesis of 4,4,5,5-tetramethyl-2-(4'-(trifluoromethyl)-[1,1'-biphenyl]-4-yl)-1,3,2-dioxaborolane (16)

To a mixture of compound 15 (1.5 g, 5.00 mmol), $(pin)_2B_2$ (2.53 g, 10.0 mmol) in dioxane-water (9:1) (20 mL) was added KOAc (0.98 g, 10.0 mmol) and the resulting mixture was degassed with $N_2$ for 20 min. $PdCl_2$(dppf).$CH_2Cl_2$ complex (164 mg, 0.22 mmol) was added and the reaction mixture was heated to 100° C. for 12 h. After completion of the reaction, the mixture was filtered through a Celite pad and the filtrate was concentrated to afford compound 16 (1.5 g, crude).

Step 3: Synthesis of 3-(4'-(trifluoromethyl)-[1,1'-biphenyl]-4-yl) pyridine (17)

To a mixture of compound 16 (1.5 g, 43.10 mmol) and compound 1 (1.02 g, 64.65 mmol) in dioxane: water (9:1) (25 mL) was added $Na_2CO_3$ (0.91 g, 86.2 mmol) and the resulting mixture was degassed with $N_2$ for 20 min. $PdCl_2$(dppf).$CH_2Cl_2$ complex (136 mg, 0.19 mmol) was added and the resulting mixture was heated to 100° C. for 12 h. After completion of the reaction the solution was filtered through a Celite pad and the filtrate was concentrated to dryness under reduced pressure. The crude was purified by silica gel column chromatography [gradient elution with 10% EtOAc in Hexane] to afford compound 6 (650 mg, 52%). LCMS (m/z): 300.3 $[M+H]^+$ Step 4: Synthesis of 3-(4'-(trifluoromethyl)-[1,1'-biphenyl]-4-yl) piperidine (18)

To a stirred solution of Compound 17 (500 mg, 1.67 mmol) in MeOH (2 mL) and concentrated HCl (0.5 mL) was added Pd/C (50% wet) (250 mg,) and the resulting suspension was stirred under hydrogen (50 psi) at 45° C. for 24 h. After completion of the reaction, the reaction mixture was filtered through a Celite pad and the filtrate was basified with a saturated $NaHCO_3$ solution and subsequently extracted with ethyl acetate (50 mL×3). The combined organic layer was dried over anhydrous sodium sulfate and concentrated to afford compound 7 (300 mg, 60%). LCMS (m/z): 306.2 $[M+H]^+$ $^1$HNMR (400 MHz, $CDCl_3$): δ 7.6 (t, J=1.5 Hz, 4H), 7.54 (d, J=7.7 Hz, 2H), 7.32 (d, J=8.0 Hz, 2H), 3.51-3.32 (m, 2H), 2.97-2.93 (m, 1H), 2.81-2.75 (m, 2H), 2.12-2.16 (m, 5H).

Step 5: Synthesis of 1-(cyclopentylmethyl)-3-(4'-(trifluoromethyl)-[1,1'-biphenyl]-4-yl) piperidine. Compound 1,011

To a stirred solution of Compound 18 (220 mg, 0.72 mmol) in acetonitrile (2.5 mL) was added $K_2CO_3$ (298 mg, 2.16 mmol) and compound 5 (235 mg, 1.44 mmol). The reaction mixture was stirred at 70° C. for 12h in a sealed tube. After completion of the reaction, the mixture was filtered, and the filtrate was concentrated to dryness. The crude product was purified by silica gel column chromatography and further purified by preparative-HPLC to afford 1-(cyclopentylmethyl)-3-(4'-(trifluoromethyl)-[1,1'-biphenyl]-4-yl) piperidine, compound 1,011 (35 mg, 12%). LCMS (m/z): 338.2 [M+H]+. $^1$H NMR (400 MHz, dmso-d6): δ 7.87 (d, J=8.4 Hz, 2H), 7.79 (d, J=8.4 Hz, 2H), 7.04 (d, J=8.4 Hz, 1H), 7.57(d, J=8.4 Hz, 2H), 3.05-2.75 (m, 3H), 2.21 (d, J=7.2 Hz, 2H), 2.12-1.82 (m, 4H), 1.69-1.56 (m, 3H), 1.54-1.44 (m, 6H), 1.27-0.58 (m, 2H).

Preparation of Compound 1,012: 1-(cyclopentylmethyl)-3-(4'-(trifluoromethyl)-[1,1'-biphenyl]-4-yl) piperidine

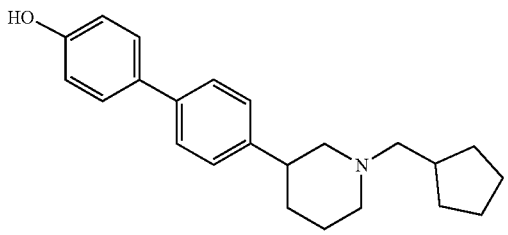

Compound 1,012

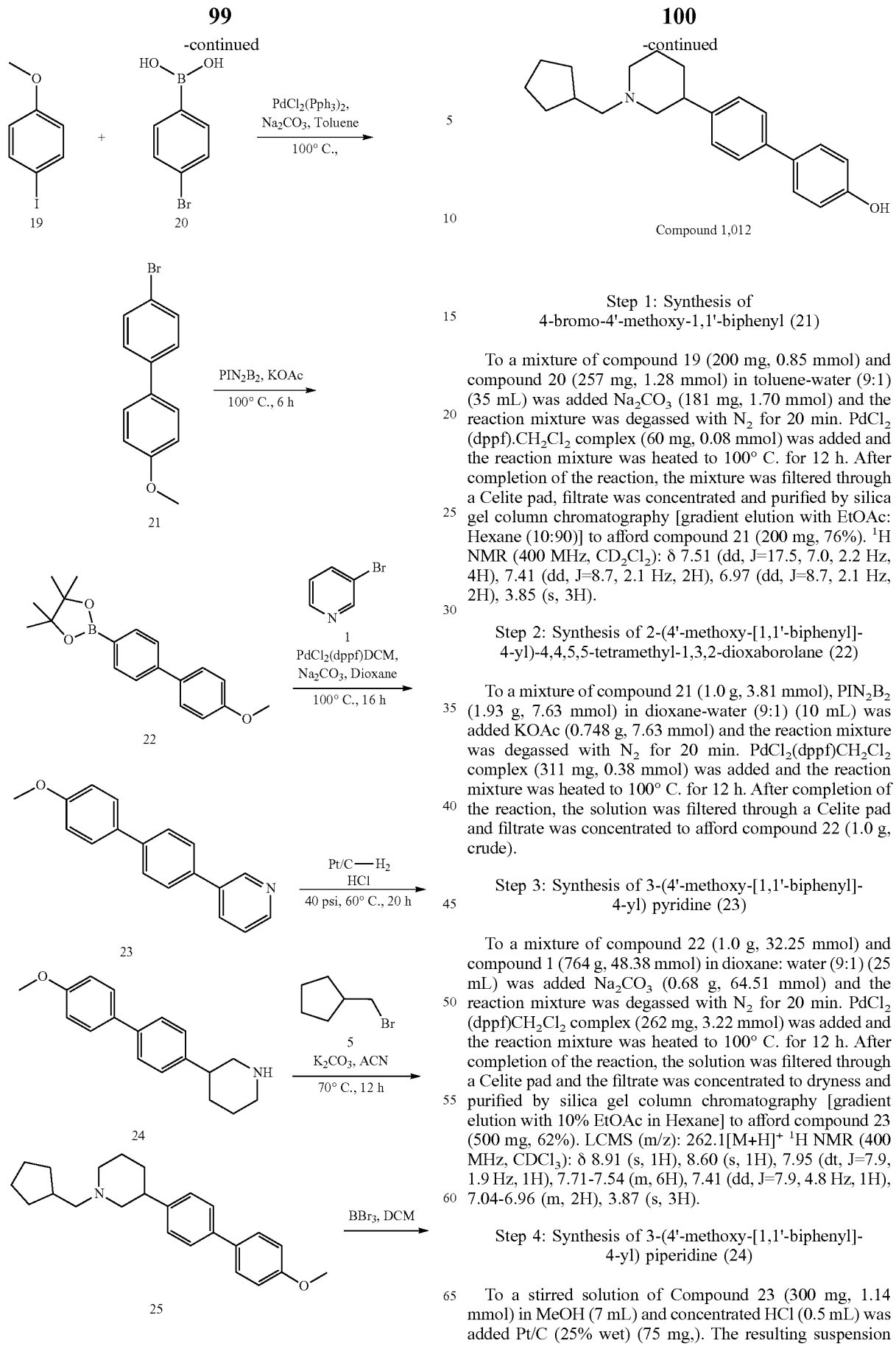

Compound 1,012

Step 1: Synthesis of 4-bromo-4'-methoxy-1,1'-biphenyl (21)

To a mixture of compound 19 (200 mg, 0.85 mmol) and compound 20 (257 mg, 1.28 mmol) in toluene-water (9:1) (35 mL) was added $Na_2CO_3$ (181 mg, 1.70 mmol) and the reaction mixture was degassed with $N_2$ for 20 min. $PdCl_2$(dppf).$CH_2Cl_2$ complex (60 mg, 0.08 mmol) was added and the reaction mixture was heated to 100° C. for 12 h. After completion of the reaction, the mixture was filtered through a Celite pad, filtrate was concentrated and purified by silica gel column chromatography [gradient elution with EtOAc: Hexane (10:90)] to afford compound 21 (200 mg, 76%). $^1$H NMR (400 MHz, $CD_2Cl_2$): δ 7.51 (dd, J=17.5, 7.0, 2.2 Hz, 4H), 7.41 (dd, J=8.7, 2.1 Hz, 2H), 6.97 (dd, J=8.7, 2.1 Hz, 2H), 3.85 (s, 3H).

Step 2: Synthesis of 2-(4'-methoxy-[1,1'-biphenyl]-4-yl)-4,4,5,5-tetramethyl-1,3,2-dioxaborolane (22)

To a mixture of compound 21 (1.0 g, 3.81 mmol), $PIN_2B_2$ (1.93 g, 7.63 mmol) in dioxane-water (9:1) (10 mL) was added KOAc (0.748 g, 7.63 mmol) and the reaction mixture was degassed with $N_2$ for 20 min. $PdCl_2$(dppf)$CH_2Cl_2$ complex (311 mg, 0.38 mmol) was added and the reaction mixture was heated to 100° C. for 12 h. After completion of the reaction, the solution was filtered through a Celite pad and filtrate was concentrated to afford compound 22 (1.0 g, crude).

Step 3: Synthesis of 3-(4'-methoxy-[1,1'-biphenyl]-4-yl) pyridine (23)

To a mixture of compound 22 (1.0 g, 32.25 mmol) and compound 1 (764 g, 48.38 mmol) in dioxane: water (9:1) (25 mL) was added $Na_2CO_3$ (0.68 g, 64.51 mmol) and the reaction mixture was degassed with $N_2$ for 20 min. $PdCl_2$(dppf)$CH_2Cl_2$ complex (262 mg, 3.22 mmol) was added and the reaction mixture was heated to 100° C. for 12 h. After completion of the reaction, the solution was filtered through a Celite pad and the filtrate was concentrated to dryness and purified by silica gel column chromatography [gradient elution with 10% EtOAc in Hexane] to afford compound 23 (500 mg, 62%). LCMS (m/z): 262.1[M+H]$^+$ $^1$H NMR (400 MHz, $CDCl_3$): δ 8.91 (s, 1H), 8.60 (s, 1H), 7.95 (dt, J=7.9, 1.9 Hz, 1H), 7.71-7.54 (m, 6H), 7.41 (dd, J=7.9, 4.8 Hz, 1H), 7.04-6.96 (m, 2H), 3.87 (s, 3H).

Step 4: Synthesis of 3-(4'-methoxy-[1,1'-biphenyl]-4-yl) piperidine (24)

To a stirred solution of Compound 23 (300 mg, 1.14 mmol) in MeOH (7 mL) and concentrated HCl (0.5 mL) was added Pt/C (25% wet) (75 mg,). The resulting suspension was stirred under hydrogen (50 psi) at 45° C. for 24h. After completion of the reaction, the mixture was filtered through a Celite pad and the filtrate was basified with saturated NaHCO₃ solution and extracted with ethyl acetate (50 mL×3). The combined organic layer was dried over sodium sulfate and concentrated to afford compound 24 (200 mg, 66%). LCMS (m/z): 268.2 [M+H]⁺ ¹HNMR (400 MHz, dmso-d6): δ 7.57-7.50 (m, 4H), 7.31-7.24 (m, 2H), 7.03-6.98 (m, 2H), 3.79 (s, 3H), 2.97 (t, J=13.9 Hz, 2H), 2.67-2.55 (m, 1H), 2.11-1.95 (m, 1H), 1.88 (d, J=12.4 Hz, 1H), 1.75-1.38 (m, 2H), 1.07 (s, 3H).

Step 5: Synthesis of 1-(cyclopentylmethyl)-3-(4'-methoxy-[1,1'-biphenyl]-4-yl) piperidine (25)

To a stirred solution of compound 24 (200 mg, 0.74 mmol) in acetonitrile (2.5 mL) was added K₂CO₃ (205 mg, 1.14 mmol) followed by compound 5 (121 mg, 0.74 mmol). The reaction mixture was stirred at 70° C. for 12 h in sealed tube. After completion of the reaction, the mixture was filtered and the filtrate was concentrated to dryness. The crude product was further purified by silica gel column chromatography to afford compound 25 (150 mg, 57%). LCMS (m/z): 350 [M+H]⁺

Step 6: Synthesis of 4'-(1-(cyclopentylmethyl) piperidin-3-yl)-[1,1'-biphenyl]-4-ol Compound 1,012

To a solution of compound 25 (150 mg, 0.42 mmol) in 2 mL of CH₂Cl₂ (2 mL) was added BBr₃ (0.5 mL) at −78° C. and the resulting solution stirred at −78° C. for 42 h. After completion of the reaction the mixture was neutralized with saturated NaHCO₃ solution and extracted with EtOAc (10 mL×2). The combined organic layer was dried over anhydrous sodium sulfate, filtered and concentrated to dryness under reduced pressure. The crude product was further purified by silica gel column chromatography and by PREP HPLC to afford compound 1,012, 4'-(1-(cyclopentylmethyl) piperidin-3-yl)[1,1'-biphenyl]-4-ol (35 mg, 15%). LCMS (m/z): 336.3 [M+H]⁺ ¹H NMR (400 MHz, DMSO-d₆): δ 9.50 (s, 1H), 7.50-7.40 (m, 4H), 7.28 (d, J=8.1 Hz, 2H), 6.814-6.83 (m, 2H), 2.87 (d, J=10.4 Hz, 2H), 2.76-2.67 (m, 1H), 2.2 (d, J=7.6 Hz, 2H), 2.07-1.89 (m, 3H),1.82-1.80 (m, 1H), 1.74-1.61 (m, 3H), 1.62-1.35 (m, 6H), 1.16-1.20 (m, 2H).

Preparation of Compound 1,001: 1-(cyclopropylmethyl)-3-(4'-fluoro-[1,1'-biphenyl]-4-yl) piperidine Compound 1,001

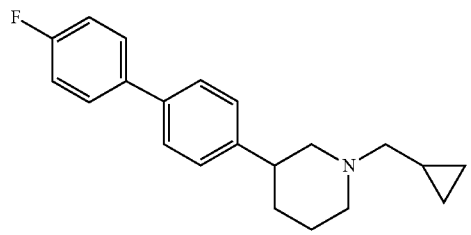

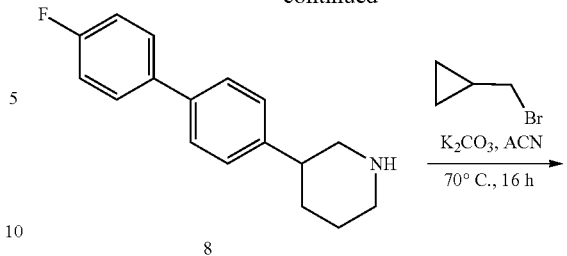

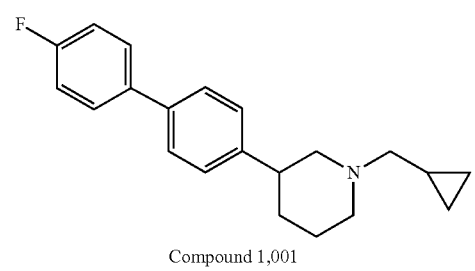

Compound 1,001

Step 1: Synthesis of 1-(cyclo propylmethyl)-3-(4'-fluoro-[1,1'-biphenyl]-4-yl) piperidine Compound 1,001

To a stirred solution of compound 8 (from compound 1,009 synthesis) (100 mg, 0.39 mmol) in acetonitrile (2 mL) was added K₂CO₃ (162 mg, 1.17 mmol) followed by (bromomethyl)cyclopropane (52 mg, 0.39 mmol). The reaction mixture was stirred at 70° C. for 16 h in sealed tube. After completion of the reaction, the mixture was filtered and the filtrate was concentrated to dryness under reduced pressure. The crude residue was further purified by silica gel column chromatography eluting with CH₂Cl₂ to give 1-(cyclo propylmethyl)-3-(4'-fluoro-[1,1'-biphenyl]-4-yl) piperidine, compound 1,001 (30 mg, 25%). LCMS (m/z): 310.1[M+H]⁺¹H NMR (400 MHz, CDCl₃): δ 7.54-7.46 (m, 4H), 7.32-7.30 (m, 2H), 7.10 (t, J=8.8 Hz, 2H), 3.20-3.13 (m, 2H), 2.95-2.92- (m, 1H), 2.31-2.28 (m, 2H), 2.06-1.95 (m, 2H), 1.82-1.78 (m, 2H), 1.53-1.46 (m, 1H), 1.25 (s, 2H), 0.92-0.88 (m, 1H), 0.52-0.49 (m, 2H), 0.1-0.08 (m, 1H).

Preparation of Compound 1,035: Synthesis of 1-benzyl-3-(4'-fluoro-[1,1'-biphenyl]-4-yl) piperidine Compound 1,035

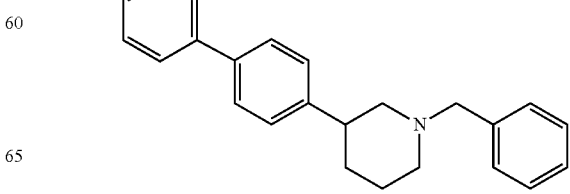

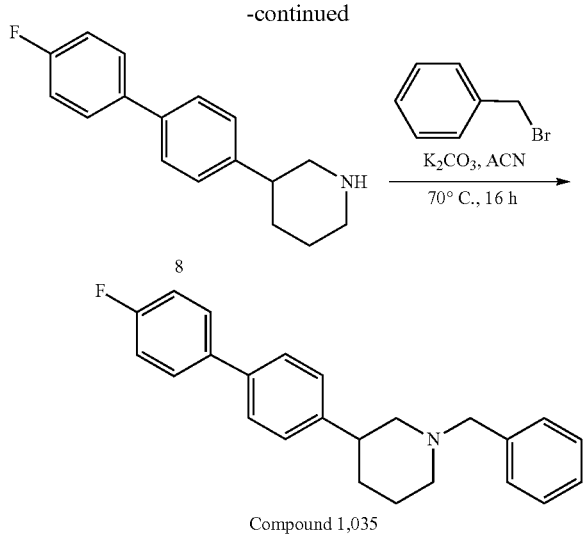

Synthesis of 1-benzyl-3-(4'-fluoro-[1,1'-biphenyl]-4-yl) piperidine, Compound 1,035

To a stirred solution of Compound 8 (from compound 1,009 synthesis) (200 mg, 0.83 mmol) in 10 mL of acetonitrile was added $K_2CO_3$ (324 mg, 2.35 mmol) followed by benzyl bromide (270 mg, 1.56 mmol). The reaction mixture was stirred at 70° C. for 16 h in sealed tube. After completion of the reaction, the mixture was filtered and the filtrate was concentrated to dryness. The crude residue was purified by silica gel column chromatography followed by preparative HPLC to afford compound 1,035, 1-benzyl-3-(4'-fluoro-[1,1'-biphenyl]-4-yl) piperidine (36 mg, 12%). LCMS (m/z): 346.2 [M+H]+ 1H NMR (400 MHz, $CDCl_3$): δ 7.32-7.43 (m, 4H), 7.38-7.21 (m, 7H), 7.13-7.06 (m, 2H), 3.55 (s,2H), 3.03-2.85 (m, 3H), 2.09-1.93 (m, 3H), 1.79-1.71 (m, 2H), 1.5-1.45 (m, 1H).

Preparation of Compound 1,041: 1-cyclopentyl-3-(4'-fluoro-3-methyl-[1,1'-biphenyl]-4-yl)piperidine

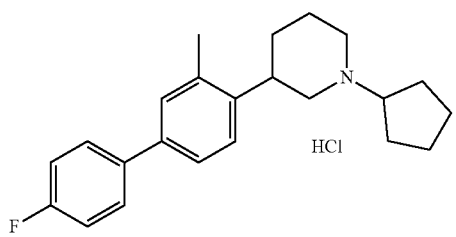

Compound 1,041

Step-1: Synthesis of 4-Bromo-4'-fluoro-3-methyl-1,1'-biphenyl

To a stirred solution of 1-bromo-4-iodo-2-methylbenzene (2 g, 6.73 mmol), (4-fluorophenyl)boronic acid (1.04 g, 7.43 mmol) in toluene: water (1:4) (10 mL) was added $Na_2CO_3$ (2.4 g, 23.07 mol) followed by $PdCl_2$(dppf). DCM (238 mg, 0.290 mmol). The reaction mixture was degassed with $N_2$ for 20 min. Then the mixture was heated to 90° C. for 12 h (Reaction progress was monitored by TLC), after completion of the reaction, it was filtered through a pad of Celite, the filtrate was concentrated and purified from column chromatography using 60-120 silica gel [gradient elution with 10% EtOAc in Hexane] to afford 1.5 g of the 4-bromo-4'-fluoro-3-methyl-1,1'-biphenyl as an off-white solid. 1H NMR (400 MHz, DMSO-d6): δ 7.54 (d, J=8.4 Hz, 1H), 7.49-7.44 (m, 2H), 7.36 (d, J=2 Hz, 1H), 7.20 (dd, J=12.8, 4.4 Hz, 1H), 7.17-7.06 (m, 2H), 2.43 (s, 3H).

Step-2: Synthesis of 3-(4'-fluoro-3-methyl-[1,1'-biphenyl]-4-yl) pyridine

To a stirred solution of 4-bromo-4'-fluoro-3-methyl-1,1'-biphenyl (1.5 g, 5.66 mmol) and pyridin-3-ylboronic acid (730 mg, 5.94 mmol) in toluene: water (1:4) (10 mL) was added $Na_2CO_3$ (2.09 g, 19.81 mmol) followed by $PdCl_2$ (dppf). DCM complex (230 mg, 0.281 mmol). The reaction mixture was degassed with $N_2$ for 20 min. Then the mixture was heated to 100° C. for 12 h (Reaction progress was monitored by TLC). After completion of the reaction, the mixture was filtered through a pad of Celite, the filtrate was concentrated and purified from column chromatography using 60-120 silica gel [gradient elution using 10% EtOAc in Hexane] to afford 1 g of 3-(4'-fluoro-3-methyl-[1,1'-biphenyl]-4-yl) pyridine as an off- white solid. 1H NMR (400 MHz, DMSO-$d_6$): δ 8.64-8.61 (m, 2H), 7.70-7.67 (m, 1H), 7.60-7.57 (m, 2H), 7.48-7.44 (m, 2H), 7.39-7.35 (m, 1H), 7.30-7.28 (m, 1H), 7.17-7.12 (m, 2H), 2.34 (s, 3H).

Step-3: Synthesis of 3-(4'-chloro-2-methyl-[1,1'-biphenyl]-4-yl) piperidine

To a stirred solution of 3-(4'-fluoro-3-methyl-[1,1'-biphenyl]-4-yl) pyridine (500 mg, 1.90 mmol) in MeOH (10 mL) was added 10% Pd/C (dry) (50 mg) and AcOH (2 mL). Then the mixture was stirred under $H_2$ atmosphere (60 psi) at 90° C. for 48 h (Reaction progress was monitored by LCMS). After completion of the reaction, the mixture was filtered through a pad of Celite. The filtrate was evaporated under reduced pressure to afford 3-(4'-chloro-2-methyl-[1,1'-biphenyl]-4-yl) piperidine as an off-white solid. 1H NMR (400 MHz, DMSO-$d_6$): δ 7.67 (t, J=8 Hz, 2H), 7.50-7.42 (m, 2H), 7.38-7.31 (m, 1H), 7.26 (t, J=8.4 Hz, 2H), 3.41-3.11 (m, 3H), 3.01-2.81 (m, 2H), 2.39 (s, 3H), 2.1-1.6 (m, 4H).

Step-4: Synthesis of 1-cyclopentyl-3-(4'-fluoro-3-methyl-[1,1'-biphenyl]-4-yl)piperidine To a stirred solution of 3-(4'-chloro-2-methyl-[1,1'-biphenyl]-4-yl) piperidine (160 mg, 0.594 mmol) and bromocyclopentane (211 mg, 0.842 mmol) in $CH_3CN$ (10 mL) was added $K_2CO_3$ (163 mg, 1.18 mmol) and heated the mixture to 70° C. in a sealed tube for 12 h. The reaction progress was monitored by LCMS, after completion of the reaction, the mixture was diluted with EtOAc and water. Both the layers were separated and the organic layer was separated and concentrated to dryness under reduced pressure. The obtained crude solid was purified from PREP-HPLC to afford Compound 1041 (TFA salt) as an off-white solid (the obtained solid was further treated with 4N dioxane.HCl and lyophilized to give Compound 1,041 as a HCl salt). 1H NMR (400 MHz, DMSO-$d_6$): δ 10.45 (brs, 1H), 7.72-7.64 (m, 2H), 7.51-7.47 (m, 2H), 7.35 (d, J=8.4 Hz, 1H), 7.31-7.25 (m, 2H), 3.59-3.43 (m, 2H), 3.41-3.35 (m, 1H), 3.31-3.20

(m, 1H), 3.11-2.93 (m, 2H), 2.40 (s, 3H), 2.11-1.95 (m, 4H), 1.88-1.63 (m, 6H), 1.59-1.48 (m, 2H).

The following method was used for the separation of the two enantiomers:

Column: CHIRALCEL OJ-H (250*4.6 mm*5.0µ)

Mobile: 0.1% DEA in HEXANE:IPA (80:20)

Flow: 1.0 mL/min

Preparation of Compound 1,043: 2-(1-cyclopentylpiperidin-3-yl)-5-(4-fluorophenyl)-3-methylpyridine

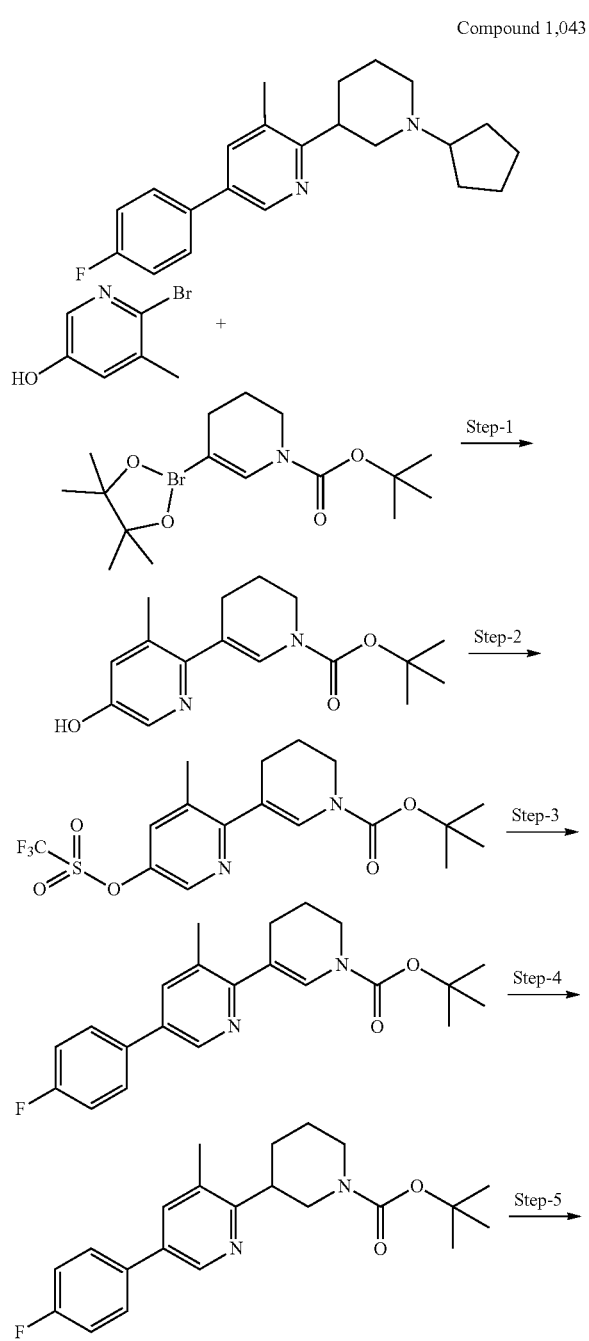

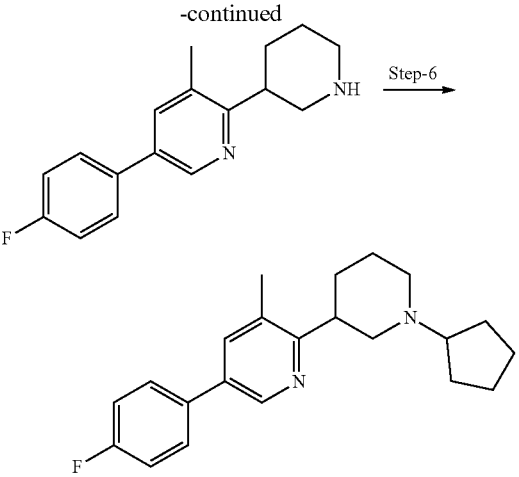

Step-1: Synthesis of tert-butyl 5-hydroxy-3-methyl-5',6'-dihydro-[2,3'-bipyridine]-1'(4'H)-carboxylate To a stirred solution of 6-bromo-5-methylpyridin-3-ol (1) (3 g, 16 mmol) in DMF (30 mL) was added tert-butyl 5-(4,4,5,5-tetramethyl-1,3,2-dioxaborolan-2-yl)-3,4-dihydropyridine-1(2H)-carboxylate (8.5 g 27 mmol) followed by a solution of 2M $Na_2CO_3$ (24 mL, 48 mmol) at 25° C. The resulting reaction mixture was degassed using nitrogen for 15 min. Then Pd(dppf)$Cl_2$. DCM (395 mg, 0.48 mmol) was added and the reaction mixture was heated to stir at 80° C. for 16h. After completion of reaction by TLC, the reaction mixture was filtered through a pad of Celite and the filtrate was concentrated under reduced pressure to dryness. The obtained residue was purified from silica gel column chromatography (100-200 mesh) using 40% ethyl acetate in hexane as an eluent giving tert-butyl 5-hydroxy-3-methyl-5',6'-dihydro-[2,3'-bipyridine]-1'(4'H)-carboxylate as an off-white solid 3.0 g (65%). $^1$H NMR (400 MHz, DMSO-d6): δ 9.64 (s, 1H), 7.92-791. (d, J=2.8 Hz 1H), 7.01-7.00 (d, J=2.8 Hz 1H), 6.97-6.84 (m, 1H), 3.52 (brs, 2H), 2.365-2.337 (t, J=5.2 Hz, 2H), 2.22 (s, 3H), 1.86-1.80 (m, 2H), 1.43 (s, 9H).

Step-2: Synthesis of tert-butyl 3-methyl-5-(((trifluoromethyl)sulfonyl)oxy)-5',6'-dihydro-[2,3'-bipyridine]-1'(4'H)-carboxylate To a stirred solution of tert-butyl 5-hydroxy-3-methyl-5',6'-dihydro-[2,3'-bipyridine]-1'(4'H)-carboxylate (3) (3 g, 10 mmol) in $CH_2Cl_2$ (40 mL) at −10° C. was added triethylamine (2.08 g, 20 mmol) followed by trifluoromethanesulfonic anhydride (3.77 g, 13 mmol) dropwise for 15 min. and the reaction mixture was left it to stir at room temperature for 16 h. After completion of reaction by TLC, the resulting mixture was cooled to 0° C. and treated with sat. sodium carbonate solution (5 mL) and extracted with $CH_2Cl_2$ (3*20 mL), washed with water (20 mL). The combined organic layer was dried over anhydrous $Na_2SO_4$, filtered and concentrated under reduced pressure to obtain tert-butyl 3-methyl-5-(((trifluoromethyl)sulfonyl) oxy)-5',6'-dihydro-[2,3'-bipyridine]-1'(4'H)-carboxylate (crude) as a pale brown solid (4.8 g). This was used in the next step without any further purification. $^1$H NMR (400 MHz, CDCl$_3$): δ 8.539-8.532 (d J=2.8 Hz, 1H), 7.889-7.883 (d J=2.4 Hz, 1H), 7.24-7.16 (m, 1H), 3.5 (brs, 2H), 3.06-3.05 (m, 2H), 2.43 (s 3H), 1.90-1.84 (m, 2H), 1.45 (s, 9H).

Step-3: Synthesis of tert-butyl 5-(4-fluorophenyl)-3-methyl-5',6'-dihydro-[2,3'-bipyridine]-1'(4'H)-carboxylate To a mixture of tert-butyl 3-methyl-5-(((trifluoromethyl) sulfonyl) oxy)-5',6'-dihydro-[2,3'-bipyridine]-1'(4'H)-carboxylate (4.8 g (Crude), 11 mmol) and (4-fluorophenyl) boronic acid (2.39 g, 17 mmol) in dioxane (50 mL) and water (2 mL) was added $K_3PO_4$ (9.68g, 34 mmol) and the reaction mixture was purged with nitrogen for 15 min. Then Pd(dppf)Cl$_2$. DCM (938 mg, 1.1 mol) was added and the reaction mixture was heated to stir at 80° C. for 16 h. After completion of reaction by TLC, the mixture was brought to room temperature and filtered through a pad of Celite. The collected filtrate was concentrated under pressure to dryness. The obtained residue was purified from silica gel column chromatography (100-200 mesh) using 6% ethyl acetate in hexane as an eluent giving tert-butyl 5-(4-fluorophenyl)-3-methyl-5',6'-dihydro-[2,3'-bipyridine]-1'(4'H)-carboxylate as an off white solid (2.8 g, overall yield 73.68% from two steps). $^1$H NMR (400 MHz, CDCl$_3$): δ 8.59 (s, 1H), 7.63 (s, 1H), 7.56-7.51 (m, 2H),7.17-7.10 (m, 3H), 3.67-3.65 (m, 2H), 2.53-2.43 (m, 2H), 2.40 (s 3H), 2.04-2.00 (m, 2H), 1.49 (s, 9H).

Step-4: Synthesis of tert-butyl 3-(5-(4-fluorophenyl)-3-methylpyridin-2-yl) piperidine-1-carboxylate To a stirred suspension of Palladium on carbon (50% wet) (1.4 g, 20% loading) in 30 mL of methanol was added tert-butyl 5-(4-fluorophenyl)-3-methyl-5',6'-dihydro-[2,3'-bipyridine]-1'(4'H)-carboxylate (2.8 g, 7 mol) and the reaction mixture was stirred under hydrogen atmosphere (60 psi) at room temperature. After being stirred for 72 h (completion of reaction by TLC), the mixture was filtered through a pad of Celite. The filtrate was concentrated under reduced pressure to dryness. The obtained residue was purified from silica gel column chromatography (100-200 mesh) using 6% ethyl acetate in hexane as an eluent to obtain tert-butyl 3-(5-(4-fluorophenyl)-3-methylpyridin-2-yl) piperidine-1-carboxylate as an off white solid (2.0 g, 71%). $^1$H NMR (400 MHz, CDCl$_3$): δ 8.57 (s, 1H), 7.58 (s, 1H), 7.57-7.49 (m, 2H), 7.17-7.11 (m, 2H), 4.19-4.09 (brs, 2H), 3.01 (brs, 2H), 2.79 (m, 1H), 2.43 (s 3H), 1.98-1.93 (m,2H), 1.82-1.78 (m, 1H), 1.64-1.60 (m 1H), 1.48 (s, 9H).

Step-5: Synthesis of 5-(4-fluorophenyl)-3-methyl-2-(piperidin-3-yl) pyridine To a stirred solution of tert-butyl 3-(5-(4-fluorophenyl)-3-methylpyridin-2-yl) piperidine-l-carboxylate (500 mg, 1.3 mmol) in dioxane (5 mL) at 0° C. was added 4M HCl in dioxane (5 mL) and the reaction mixture was left it to stir at room temperature for 4 h. After completion of the reaction by TLC, the mixture was concentrated under pressure to dryness. The obtained residue was triturated with a mixture of diethyl ether and pentane (1:1, 10 mL), filtered and dried to obtain 5-(4-fluorophenyl)-3-methyl-2-(piperidin-3-yl) pyridine as a white solid (300 mg, 83%). $^1$H NMR (400 MHz, CDCl$_3$): δ 9.41-9.38 (m, 2H), 8.75 (s, 1H), 8.25 (s, 1H), 7.86-7.82 (m, 2H), 7.39-7.34 (t, J=8.8 Hz, 2H), 3.65 (m, 1H), 3.44-3.31 (m, 3H), 2.92 (brs, 1H), 2.51 (s, 3H), 1.95-1.90 (m,4H).

Step-6: Synthesis of 2-(1-cyclopentylpiperidin-3-yl)-5-(4-fluorophenyl)-3-methylpyridine To a stirred solution of 5-(4-fluorophenyl)-3-methyl-2-(piperidin-3-yl) pyridine (300 mg, 1 mmol) in 15 mL of acetonitrile was added $K_2CO_3$ (460 mg, 3 mmol) followed by bromo cyclopentane (500 mg, 3 mmol) and the reaction mixture was heated to stir at 80° C. for 36 h. After completion of reaction by TLC, the reaction mixture was cooled to room temperature added water (5 mL). It was extracted with ethyl acetate (3*20 mL) and washed with water (20 mL). The combined organic layer was dried over anhydrous Na$_2$SO$_4$, filtered and concentrated under reduced pressure to dryness. The obtained residue was triturated with a mixture of diethyl ether and pentane (1:1, 10 mL), filtered and dried to obtain 2-(1-cyclopentylpiperidin-3-yl)-5-(4-fluorophenyl)-3-methylpyridine as an off white solid (300 mg, 83%). $^1$H NMR (400 MHz, CDCl$_3$): δ 8.58 (s, 1H), 7.57 (s, 1H), 7.57-7.49 (m, 2H), 7.16-7.12 (m, 2H), 3.30 (m, 1H), 3.12 (m, 2H), 2.6 (m, 1H), 2.41 (s 3H), 2.35 (m, 1H), 2.0 (m,1H), 1.91-1.83 (m,5H), 1.83-1.67 (m, 5H), 1.67-1.52 (m,4H).

The remaining compounds presented in Table 1, Table 2, Table 3, and Table 4 are prepared according to Scheme I or Scheme II, or by methods according to the Examples, or by methods known in the art.

Example 2: Biological Assays

The compounds of the present disclosure may be tested for binding to, inhibition of, and/or modulation of PCSK9 activity according to the following protocols.

Cell Culture

Cells, such as HepG2, HuH7, FL83B, or a cell line transfected with a short-hairpin PCSK9 knockdown sequence (e.g., HepG2/shPCSK9, HuH7/shPCSK9) can be cultured following routine procedures, such as those described by Benjannet et al., "Effects of the prosegment and pH on the activity of PCSK9: evidence for additional processing events" *J Biol Chem.* 285(52): 40965-40978 (2010), which is hereby incorporated by reference in its entirety.

LDLR Flow Cytometric Analysis

LDLR levels were measured using flow cytometry or fluorescence activated cell sorting (FACS) using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 were cultured in media composed of complete, high glucose DMEM (Invitrogen) with 10% fetal bovine serum (Life Technologies), supplemented with penicillin-streptomycin (Life Technologies). Cells were plated in a 24-well plate, at 125 k cells/well, and cultured at 37° C. for 12-24 h. Culture media was removed and replaced with fresh culture media or culture media plus a predetermined amount of recombinant PCSK9 (for example, a final PCSK9 concentration of 5 µg/mL; Cayman Chemical, Ann Arbor, MI, Catalog #20631). Wells evaluating test compounds were dosed with concentrations ranging from 0 nM to 100 µM.

Following an incubation period of 4-6 hours at 37° C., the media was removed and the cells rinsed by adding 0.5 ml of complete D-PBS (i.e., Dulbecco's phosphate buffered saline (D-PBS, Life Technologies) supplemented with 0.5% bovine serum albumin (BSA, Sigma) and 1 g/L glucose (Sigma)). The wash media was carefully aspirated, and cells released from the plate using 200 µL of TrypLE Express (Life Technologies) by incubating for 5-10 minutes at 37° C. The TyrpLE-Cell suspension was inactivated by adding 100 µL of Fetal Bovine Serum, transferred to a v-bottom plate, and centrifuged at 250× gravity for 5 minutes. Following centrifugation, the supernatant was aspirated and the cell pellet is resuspended in 100 µL of complete D-PBS, and centrifuged at 250× gravity for 5 minutes. Following centrifugation, the supernatant was aspirated and the cell pellet was resuspended in 100 µL of antibody staining solution (600 µL of anti-LDLr-PE in complete D-PBS) and incubated on ice, protected from light, for 30 minutes. The cells were then pelleted by centrifugation, resuspended in 100 µL of 4',6-Diamidino-2-phenylindole (DAPI, Cayman Chemical) or 7-aminoactinomycin D (7AAD, Life Technologies) staining solution to measure cell viability.

Cells were analyzed for both cell viability marker (dead cells) and LDLR in live cells using a flow cytometer per the manufacturer's operating manual. Cells incubated with small molecule compounds that are inhibitors of PCSK9 will be expected to show increased amounts of LDLR, relative to control (no compound) specimens, and cells incubated with small molecule compounds that are activators of PCSK9 will be expected to show decreased amounts of LDLR relative to control (no compound) specimens.

The percentage recovery in the LDLR assay at 10 µM concentration is provided as follows: +++: >80% recovery; ++: 40-80% recovery; +: 0-40% recovery. The results for selected compounds are presented in Table 5.

TABLE 5

| Compound # | LDLR percentage recovery (10 µM) |
|---|---|
| 1.001 | ++ |
| 1.002 | ++ |
| 1.003 | +++ |
| 1.005 | ++ |
| 1.006 | +++ |
| 1.009 | +++ |
| 1.010 | ++ |
| 1.011 | ++ |
| 1.035 | +++ |

The LDL-R EC50 is provided as follows: +++: <1 µM; ++: 1 µM-5 µM; +: >5 µM.

The LDL-R EC50 for selected compounds is presented in Table 6.

TABLE 6

| Compound # | LDLR EC50 |
|---|---|
| 1.001 | ++ |
| 1.003 | ++ |
| 1.005 | ++ |
| 1.006 | ++ |
| 1.009 | ++ |
| 1.010 | + |
| 1.011 | +++ |
| 1.035 | + |

Cellular DiI-LDL Uptake Analysis

Cellular DiI-LDL uptake can be measured using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24 h. Culture media is removed and replaced with fresh lipoprotein-depleted culture media supplemented with 5 µg/mL of DiI-LDL (Kalen Biomedical) or lipoprotein-depleted culture media supplemented with 5 µg/mL of DiI-LDL plus a predetermined concentration of recombinant PCSK9, for example a 10 nM final concentration of PCSK9. Lipoprotein-depleted culture media can be composed of DMEM (Invitrogen) with 10% lipoprotein-depleted fetal bovine serum (Kalen Biomedical) and supplemented with penicillin-streptomycin (Life Technologies). Cells are dosed with small molecule test compounds at doses ranging from 0 nM to 100 µM.

Following an incubation period of specified length, such as 16 hours, Hoechst 33342 (AnaSpec) stain is added to the cell media per manufacturer's instructions and incubated for a specified length (e.g., 30 minutes). The lipoprotein-depleted media is removed and cells rinsed three times with phosphate buffered saline. A final volume of phosphate buffered saline is added back to the wells. The DiI fluorescence is measured with a plate reader using an exciting wavelength of 550 nm and the resulting emission at 590 nm is measured. The Hoechst stain fluorescence is measured with a plate reader using an exciting wavelength of 355 nm and the resulting emission at 460 nm is measured.

Cells are analyzed by for both Hoechst stain (DNA content) and DiI-LDL fluorescence. Cells incubated with small molecule compounds that are inhibitors of PCSK9 will be expected to show increased amounts of DiI-LDL fluorescence, relative to control (no compound) specimens, and cells incubated with small molecule compounds that are activators of PCSK9 will be expected to show decreased amounts of DiI-LDL fluorescence relative to control (no compound) specimens.

LDL Uptake Cell-Based Assay Kit

LDL uptake and LDLR expression can also be measured in cells, such as HepG2 or HuH7 cells, using a commercial kit (Cayman Chemical, Catalog #10011125) and the accompanying protocols provided by the manufacturer.

Fluorescent-LDL Uptake Analysis by Flow Cytometric Analysis

Cells, such as HuH7, FL83B, or a cell line transfected with a short-hairpin PCSK9 knockdown sequence such as HuH7/shPCSK9 or FL83B/shPCSK9 were plated and cultured at 37° C. for 12-24 h. Culture media was removed and replaced with fresh lipoprotein-depleted culture media supplemented with 5 µg/mL of fluorescently labeled LDL or lipoprotein-depleted culture media supplemented with 5 µg/mL of fluorescently labeled LDL plus a concentration of recombinant PCSK9 (for example 5 μg/mL recombinant PCSK9; Cayman Chemical, Cat. #20631). Examples of fluorescently labeled LDL include: DiI-LDL (Kalen Biomedical), or LDL conjugated to Dylight (e.g., LDL-Dylight 488, or LDL-Dylight 550 (Cayman Chemical, Cat. #10011229)). Lipoprotein-depleted culture media was composed of DMEM (Invitrogen) with 10% lipoprotein-depleted fetal bovine serum (Kalen Biomedical) and supplemented with penicillin-streptomycin (Life Technologies). Cells were dosed with small molecule test compounds at doses ranging from 0 nM to 100 μM, following a protocol adapted from Benjannet et al., "Effects of the prosegment and pH on the activity of PCSK9: evidence for additional processing events" *J Biol Chem.* 285(52):40965-40978 (2010), which is incorporated by reference in its entirety.

Following an incubation period of specified length, such as 16 hours, the lipoprotein-depleted media was removed and cells rinsed three times with a rinse solution (Dulbecco's phosphate buffered saline (D-PBS, Life Technologies), supplemented with 0.5% bovine serum albumin (BSA, Sigma) and 1 g/L glucose (Sigma)). The fluid was then removed, and cells are released from the plate using TrypLE Express (Life Technologies) per manufacturer's recommended procedures, such as incubation for 5-10 minutes at 37° C. The TyrpLE-Cell suspension was then transferred to 15 mL conical tubes, volume was increased to 2 mL with D-PBS supplemented with 0.5% BSA, and 1 g/mL glucose, and the tubes were centrifuged at 250× gravity for 10 minutes. Following centrifugation, the supernatant was aspirated and the cell pellet was resuspended in 300 μL PBS and counterstained with 4',6-diamidino-2-phenylindole (DAPI, Cayman Chemical) as a cell viability marker, other cell viability markers such as 7-aminoactinomycin D (7AAD, Life Technologies) have also been described in the art.

Cells were analyzed by for both 7AAD (dead cells) and fluorescent LDL in live cells using a flow cytometer per the manufacturer's operating manual. Cells incubated with small molecule compounds that are inhibitors of PCSK9 will be expected to show increased amounts of LDL fluorescence, relative to control (no compound) specimens, and cells incubated with small molecule compounds that are activators of PCSK9 will be expected to show decreased amounts of LDL fluorescence relative to control (no compound) specimens.

The LDL-uptake EC50 is provided as follows: +++: <0.5 μM; ++: 0.5-1 μM; +: >1 μM. The LDL-uptake EC50 for selected compounds is presented in Table 7.

TABLE 7

| Compound # | LDL-uptake EC50 |
| --- | --- |
| 1.006 | ++ |
| 1.009 | +++ |
| 1.010 | +++ |
| 1.011 | +++ |
| 1.013 | + |
| 1.027 | + |
| 1.029 | ++ |
| 1.035 | ++ |
| 1.039 | ++ |
| 1.040 | ++ |
| 1.041 | ++ |

Biodesy Direct Binding Measurement

Direct binding can be measured using the commercially available Biodesy Delta System (BDS, http://www.biodesy.com/products/; accessed Aug. 1, 2018). The BDS is a laser-based approach that utilizes second harmonic generation from a labeled protein to detect ligand binding, the method of which is covered and described by U.S. Pat. Nos. 9,395,358 and 8,932,822, and has been commercialized by Biodesy Inc. (South San Francisco, Calif.). In this assay compound 1,001 demonstrated a ASHG >10%.

Microsomal Stability Analysis

Microsomal stability was determined as follows:
The assay was carried out in 96-well microtiter plates at 37° C. Reaction mixtures (25 μL) contained a final concentration of 1 μM test compound, 0.5 mg/mL liver microsomes protein, and 1 mM NADPH and/or 1 mM UDPGA (with alamethicin) in 100 mM potassium phosphate, pH 7.4 buffer with 3 mM $MgCl_2$. At each of the time points (for example, 0, 15, 30, and 60 minutes), 150 μL of quench solution (100% acetonitrile with 0.1% formic acid) with internal standard was transferred to each well. Besides the zero minute controls, mixtures containing the same components except the NADPH can also be prepared as the negative control. Verapamil was included as a positive control to verify assay performance. Plates were sealed, vortexed, and centrifuged at 4° C. for 15 minutes at 4000 rpm. The supernatant was transferred to fresh plates for LC/MS/MS analysis. The extent of metabolism was calculated as the disappearance of the test compound, compared to the 0-min time incubation. Initial rates were calculated for the compound concentration and used to determine t1/2 values.

A summary of measured microsomal stability is presented in Table 8:

TABLE 8

| Compound # | Microsomal Stability $t_{1/2}$ min (mouse, rat, human) |
| --- | --- |
| 1.001 | 25, 10, >120 |
| 1.006 | 28, 13, 22 |
| 1.009 | 67, 13, 86 |
| 1.010 | 76, 15, >120 |
| 1.011 | 61, 17, >120 |

Example 3: In Vivo PK and Efficacy

All aspects of this work including housing, experimentation, and animal disposal were performed in general accordance with the "Guide for the Care and Use of Laboratory Animals: Eighth Edition" (National Academies Press, Washington, D.C., 2011).

A representative compound (Compound 1041) was tested for oral bioavailability and efficacy in mice. Male C57BL/6 mice were purchased from Taconic Biosciences (Rensselaer, New York) and housed under standard conditions with the exception of being provided a high fat diet (#TD.90221, Envigo, Madison, Wis.) and water ad libitum. Following 4 weeks of diet acclimation the animals were then dosed with compound or vehicle as control specimens. Compound readily dissolved at 1.5 mg/ml in a 1% Tween-80 aqueous solution with 10-15 minutes sonication. This solution was used at the 1.5 mg/ml concentration for oral (PO) dosing or further diluted with sterile saline for intravenous (IV) dosing.

Test animals received a single dose at 3 mg/kg by IV or 15 mg/kg by PO while control animals received an equal volume of vehicle control by IV or PO, respectively. Plasma samples were collected at 0.25, 5, 1, 2, 3, 6, 8, 24, and 48 hours while liver specimens were collected at 8, 24, and 48 hours and drug concentration were measured by LC-MS/MS per standard protocols.

In brief, blood was immediately centrifuged, and the resulting plasma was frozen and stored at −80° C. until analysis. Livers from each animal was harvested, weighed, frozen and stored at −80° C. until analysis. Compound concentrations were determined by a liquid chromatography-mass tandem spectrometry (LC-MS/MS) per routine method (Quintana Discovery, Hayward, Calif.) following the standard protocol. To summarize, liver samples were homogenized in two volumes of ice-cold water, then 20 uL of each plasma or liver homogenate sample were extracted using 100 uL of acetonitrile containing an internal standard of terfenadine. The mixture was agitated for 15 minutes and then centrifuged at 4000 rpm for 15 minutes. A 50 uL aliquot of the supernatant was mixed with 100 uL of water for the injection to the LC-MS/MS and extracts were measured using positive electrospray ionization. Pharmacokinetic parameters for the compound were generated by non-compartmental analysis with Phoenix™ WinNonlin® software (Pharsight Corporation, St. Louis, Mo.). Comparing the 3 mg/kg IV and 15 mg/kg PO, the results indicated that the representative compound had an oral bioavailability (F %) of 44%. The IV administration at 3 mg/kg had a measured compound half-life in plasma of 4.8 hrs and the 15 mg/kg by PO administration had a measured compound half-life of 9.8 hours in plasma.

Serum lipid levels were measured using commercially available veterinary health testing services provided by IDEXX BioAnalytics (North Grafton, Mass.). Blood specimens were collected from the animals and the resulting serum was frozen and stored at −80° C. until analysis. Specimens were measured using the commercial service's standard procedures for the Rodent Lipid Panel (Test Code #6290). Lipid results showed that a single 3 mg/kg IV dose resulted in a 19% reduction in LDL relative to the IV vehicle control group as measured 48 hours after dosing (t-test, p<0.05), while the 15 mg/kg PO dose resulted in a 32% reduction in LDL relative to the PO vehicle control group as measured 48 hours after dosing (t-test, p<0.05). When compound was administered daily by PO at 15 mg/kg, LDL showed a 32% reduction at 48 hours (dosed at t=0 and again at t=24 hours) and a 50% reduction in LDL at 72 hours (dosed at t=0, t=24, and t=48 hours). Together these data provide direct experimental examples indicating that the representative compound is orally bioavailable and efficacious at lowering LDL cholesterol levels in vivo in a mammalian test subject.

To assess animal health following compound exposure, a liver panel (Test Code #60405) was tested by IDEXX BioAnalytics (North Grafton, Mass.). Results of the liver panel for the animals exposed to three separate daily 15 mg/kg PO doses of compound showed no overt toxicity at 72 hours in the panel when compared against the PO vehicle control animals. Also of note, AST and ALT levels in the liver panel were elevated in the PO vehicle, which is attributed to the high fat diet used in the study (Envigo, #TD.90221). In contrast to the vehicle control group, the 72-hour group treated daily with 15 mg/kg PO showed a 72.1% reduction in AST levels and a 77.7% reduction in ALT levels and indicates improving liver function following repeated treatment with the compound. These data provides direct experimental evidence that compounds are reversing liver damage induced by a high fat diet and could thus be useful as a treatment for liver disease or liver dysfunction, including conditions such as non-alcoholic fatty liver disease.

Thus, it should be understood that although the present disclosure has been specifically disclosed by exemplary embodiments and optional features, modification, improvement and variation of the disclosed embodiments may be implemented by those skilled in the art, and that such modifications, improvements and variations are considered to be within the scope of the present disclosure and claims. The materials, methods, and examples provided here are representative of preferred embodiments, are exemplary, and are not intended as limitations on the scope of the disclosure nor as limitations on the scope of the appended claims.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed:

1. A compound of Formula I:

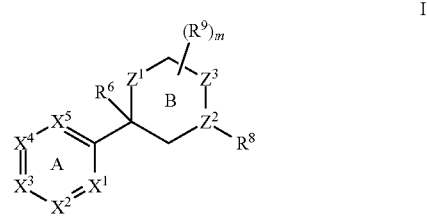

or a pharmaceutically acceptable salt, prodrug, deuterated analog, stereoisomer, or mixture of stereoisomers thereof, wherein:

Ring A is a six-membered aromatic ring; $X^1$, $X^4$ and $X^5$ are independently CH or $CR^1$, $X^2$ is CH or $CR^2$, and $X^3$ is $CR^3$, provided that at least one of $X^2$ and $X^3$ is other than CH;

Ring B is a six-membered non-aromatic ring; $Z^1$ is $CH_2$, $CHR^9$, $CR^9R^9$, or S; $Z^2$ is N; and $Z^3$ is $CHR^7$ or $CR^7R^9$;

each of $R^1$ and $R^9$ are independently $C_1$-$C_6$ alkyl, heterocyclyl, heteroaryl, halo, OH, $C_1$-$C_6$ alkoxy, $C_1$-$C_6$ haloalkyl, $C_1$-$C_6$ hydroxyalkyl, CN, or $NH_2$;

m is 0, 1, 2, 3 or 4, and is not inclusive of $R^9$ groups at $Z^1$ or $Z^3$;

$R^3$ is $C_3$-$C_6$ cycloalkyl, phenyl, heteroaryl, or heterocyclyl;

$R^2$ is H, $C_1$-$C_6$ alkyl, halo, OH, $C_1$-$C_6$ alkoxy, $C_1$-$C_6$ haloalkyl, $C_1$-$C_6$ hydroxyalkyl, CN, $NH_2$, $C_3$-$C_6$ cycloalkyl, phenyl, heteroaryl, or heterocyclyl, wherein each of the $C_3$-$C_6$ cycloalkyl, phenyl, heteroaryl, or heterocyclyl of $R^2$ and $R^3$ is monocyclic and further wherein each of which is optionally substituted with one to five $R^4$;

each $R^4$ is independently selected from $C_1$-$C_6$ alkyl, halo, OH, $C_1$-$C_6$ alkoxy, $C_1$-$C_6$ haloalkyl, $C_1$-$C_6$ hydroxyalkyl, and CN;

$R^6$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^7$ is H, halo, $C_1$-$C_6$ alkyl, $C_1$-$C_6$ alkoxy, $C_1$-$C_6$ hydroxyalkyl, $C_1$-$C_6$ haloalkyl, OH, CN, or $NH_2$;

$R^8$ is $C_3$-$C_6$ alkyl, $C_1$-$C_6$ heteroalkyl, $C_3$-$C_6$ cycloalkyl, heterocyclyl, aryl, heteroaryl, $C_3$-$C_6$ cycloalkyl-$C_1$-$C_6$ alkyl, heteroaryl-$C_1$-$C_6$ alkyl, or heterocyclyl-$C_1$-$C_6$ alkyl; each of which is optionally substituted with one to four substituents independently selected from $C_1$-$C_6$ alkyl, $C_1$-$C_6$ alkoxy, $C_1$-$C_6$ hydroxyalkyl, $C_1$-$C_6$ haloalkyl, halo, $=NR^{11}$, CN, $NH_2$ and OH; or $R^8$ and $R^7$ together with the atoms to which they are attached form Ring C, which is a $C_3$-$C_6$ cycloalkyl or heterocyclyl ring fused with Ring B, wherein Ring C is optionally substituted with one to four $R^{12}$;

$R^{11}$ is H or $C_1$-$C_6$ alkyl;

each $R^{12}$ is independently selected from the group consisting of $C_1$-$C_6$ alkyl, halo, OH, $C_1$-$C_6$ alkoxy, $C_1$-$C_6$ hydroxyalkyl, $C_1$-$C_6$ haloalkyl, $NH_2$ and CN; or two $R^{12}$ together with the atoms to which they are attached form Ring D, which is $C_3$-$C_6$ cycloalkyl or heterocyclyl fused with Ring C; or two $R^{12}$ on a same carbon atom form =O or $=NR^{11}$.

2. The compound of claim 1, wherein $Z^3$ is $CHR^7$.

3. The compound of claim 1 of Formula III:

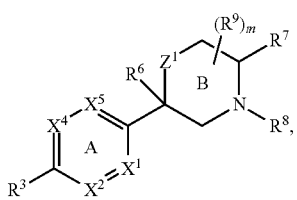

III or a pharmaceutically acceptable salt, prodrug, deuterated analog, stereoisomer, or mixture of stereoisomers thereof, wherein:

$R^3$ is $C_3$-$C_6$ cycloalkyl, phenyl, 5-or 6-membered heteroaryl, or 5-or 6-membered heterocyclyl, wherein each of the $C_3$-$C_6$ cycloalkyl, phenyl, 5-or 6-membered heteroaryl, or 3-to 6-membered heterocyclyl is monocyclic and further wherein each of which is optionally substituted with one to five $R^4$, and each $R_4$ is independently selected from $C_1$-$C_6$ alkyl, halo, OH, $C_1$-$C_6$ alkoxy, $C_1$-$C_6$ hydroxyalkyl, $C_1$-$C_6$ haloalkyl, and CN.

4. The compound of claim 1 of Formula V:

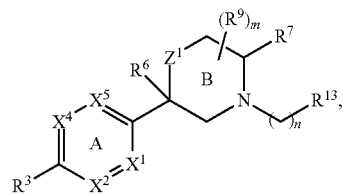

V or a pharmaceutically acceptable salt, prodrug, deuterated analog, stereoisomer, or mixture of stereoisomers thereof, wherein:

$R^3$ is $C_3$-$C_6$ cycloalkyl, phenyl, 5-or 6-membered heteroaryl, or 3-to 6-membered heterocyclyl, wherein each of the $C_3$-$C_6$ cycloalkyl, phenyl, 5-or 6-membered heteroaryl, or 3-to 6-membered heterocyclyl is monocyclic and further wherein each of which is optionally substituted with one to five $R^4$, each $R^4$ is independently selected from $C_1$-$C_6$ alkyl, halo, OH, $C_1$-$C_6$ alkoxy, $C_1$-$C_6$ haloalkyl, $C_1$-$C_6$ hydroxyalkyl, and CN;

n is 0, 1 or 2;

$R^7$ is H, halo, $C_1$-$C_6$ alkyl, $C_1$-$C_6$ alkoxy, $C_1$-$C_6$ haloalkyl, OH, CN, or $NH_2$; and $R^{13}$ is $C_3$-$C_6$ cycloalkyl, 5-or 6-membered heteroaryl, or 3-to 6-membered heterocyclyl, wherein the $C_3$-$C_6$ cycloalkyl, 5-or 6-membered heteroaryl, or 3-to 6-membered heterocyclyl is optionally substituted with one or two substituents independently selected from $C_1$-$C_6$ alkyl, $C_1$-$C_6$ alkoxy, $C_1$-$C_6$ hydroxyalkyl, $C_1$-$C_6$ haloalkyl, halo, $=NR_{11}$, CN, $NH_2$ and OH.

5. A pharmaceutical composition comprising a pharmaceutically acceptable excipient and a compound of claim 1, or a pharmaceutically acceptable salt, prodrug, deuterated analog, stereoisomer, or mixture of stereoisomers thereof.

6. A pharmaceutical composition comprising a pharmaceutically acceptable excipient, a compound of claim 1, and one or more additional pharmaceutical drugs.

7. A method of treating a disease or condition mediated, at least in part, by PCSK9, the method comprising administering to a patient in need thereof an effective amount of a compound of claim 1 or a pharmaceutical composition thereof wherein the disease or condition is a cardiovascular disease, a metabolic disease, liver disease, or hypercholesterolemia.

* * * * *